United States Patent
Nureki et al.

(10) Patent No.: US 11,530,396 B2
(45) Date of Patent: Dec. 20, 2022

(54) MODIFIED CAS9 PROTEIN, AND USE THEREOF

(71) Applicants: THE UNIVERSITY OF TOKYO, Bunkyo-ku (JP); MODALIS THERAPEUTICS CORPORATION, Chuo-ku (JP)

(72) Inventors: Osamu Nureki, Bunkyo-ku (JP); Hiroshi Nishimasu, Bunkyo-ku (JP); Hisato Hirano, Bunkyo-ku (JP); Shohei Kajimoto, Bunkyo-ku (JP); Tetsuya Yamagata, Cambridge, MA (US); Yuanbo Qin, Cambridge, MA (US); Keith M. Connolly, Cambridge, MA (US); Iain Thompson, Cambridge, MA (US)

(73) Assignees: THE UNIVERSITY OF TOKYO, Bunkyo-ku (JP); MODALIS THERAPEUTICS CORPORATION, Chuo-ku (JP)

( * ) Notice: Subject to any disclaimer, the term of this patent is extended or adjusted under 35 U.S.C. 154(b) by 292 days.

(21) Appl. No.: 16/644,378

(22) PCT Filed: Sep. 5, 2018

(86) PCT No.: PCT/JP2018/032948
§ 371 (c)(1),
(2) Date: Mar. 4, 2020

(87) PCT Pub. No.: WO2019/049913
PCT Pub. Date: Mar. 14, 2019

(65) Prior Publication Data
US 2021/0163907 A1 Jun. 3, 2021

Related U.S. Application Data

(60) Provisional application No. 62/554,227, filed on Sep. 5, 2017, provisional application No. 62/668,968, filed on May 9, 2018, provisional application No. 62/724,981, filed on Aug. 30, 2018.

(51) Int. Cl.
| | |
|---|---|
| *C12N 9/22* | (2006.01) |
| *A61K 47/54* | (2017.01) |
| *C12N 15/11* | (2006.01) |
| *C12N 15/90* | (2006.01) |
| *C12N 15/113* | (2010.01) |

(52) U.S. Cl.
CPC .............. *C12N 9/22* (2013.01); *A61K 47/549* (2017.08); *C12N 15/11* (2013.01); *C12N 15/902* (2013.01); *C12N 15/907* (2013.01); C12N 2310/20 (2017.05); C12N 2310/3513 (2013.01); C12N 2800/80 (2013.01)

(58) Field of Classification Search
None
See application file for complete search history.

(56) References Cited

U.S. PATENT DOCUMENTS

| | | |
|---|---|---|
| 9,512,446 B1 | 12/2016 | Joung et al. |
| 9,637,739 B2 | 5/2017 | Šikšnys et al. |
| 10,844,378 B2 | 11/2020 | Šikšnys et al. |
| 2015/0045546 A1 | 2/2015 | Šikšnys et al. |
| 2015/0050699 A1 | 2/2015 | Šikšnys et al. |
| 2015/0240261 A1 | 8/2015 | Šikšnys et al. |
| 2015/0291961 A1 | 10/2015 | Šikšnys et al. |
| 2016/0312198 A1 | 10/2016 | Joung et al. |
| 2017/0121693 A1 | 5/2017 | Liu et al. |
| 2018/0187195 A1 | 7/2018 | Šikšnys et al. |
| 2018/0312824 A1 | 11/2018 | Zhang et al. |
| 2019/0085329 A1 | 3/2019 | Šikšnys et al. |

FOREIGN PATENT DOCUMENTS

| | | |
|---|---|---|
| JP | 2015-510778 A | 4/2015 |
| WO | WO 2014/093661 A1 | 6/2014 |
| WO | WO 2016/141224 A1 | 9/2016 |
| WO | WO 2016/205759 A1 | 12/2016 |
| WO | WO 2017/010543 A1 | 1/2017 |
| WO | WO 2017/040348 A1 | 3/2017 |
| WO | WO 2017/070633 A2 | 4/2017 |

OTHER PUBLICATIONS

International Search Report and Written Opinion dated Dec. 4, 2018 in PCT/JP2018/032948, 9 pages.
Extended European Search Report dated May 12, 2021 in corresponding European Patent Application No. 18853529.8, 9 pages.
Nishimasu, Hiroshi et al., "Crystal Structure of *Staphylococcus aureus* Cas9", Cell, vol. 162, No. 5, XP055304450, Aug. 27, 2015, pp. 1113-1126.
Kleinstiver, Benjamin et al., "Engineered CRISPR-Cas 9 nucleases with altered PAM specificities", Nature, vol. 523, No. 7561, 2015, pp. 481-485.
Nureki, Osamu et al., "Structure-based development of CRISPR genome-editing tool", Experimental medicine, 2016, vol. 34, No. 20, pp. 3276-3286.
Nureki, Osamu, "Structure-based development of a CRISPR-Cas9 genome editing tool", Bioscience & industry, vol. 75, No. 2, Mar. 2017, pp. 104-113.

(Continued)

*Primary Examiner* — Suzanne M Noakes
*Assistant Examiner* — Jae W Lee
(74) *Attorney, Agent, or Firm* — Oblon, McClelland, Maier & Neustadt, L.L.P.

(57) ABSTRACT

A mutant SaCas9 protein such as a protein having an amino acid sequence resulting from mutations of glutamic acid at the 782-position to lysine (E782K), leucine at the 800-position to arginine (L800R), asparagine at the 968-position to arginine (N968R), asparagine at the 985-position to alanine (N985A), arginine at the 991-position to alanine (R991A), alanine at the 1021-position to serine (A1021S), threonine at the 927-position to lysine (T927K), lysine at the 929-position to asparagine (K929N), and isoleucine at the 1017-position to phenylalanine (I1017F) in SEQ ID NO: 2 has relaxed restriction on target sequence while maintaining binding ability to guide RNA, and is useful as a tool for gene editing.

25 Claims, 17 Drawing Sheets

Specification includes a Sequence Listing.

(56) References Cited

OTHER PUBLICATIONS

Ran, F.A., et al., "Double Nicking by RNA-Guided CRISPR Cas9 for Enhanced Genome Editing Specificity", Cell, vol. 154, No. 6, 2013, pp. 1380-1389.

Ran, F.A., et al., "In vivo genome editing using *Staphylococcus aureus* Cas9", Nature, vol. 520, No. 7546, 2015, pp. 186-191.

Fig. 6-1

WT-dSaCas9-KRAB
NLS-WT-dSaCas9(D10A, N580A)-NLS-KRAB-P2A-Puro fusion protein sequence:

NLS     dsaCas9 (original)     KRAB-P2A-Puro

MAPKKKRKVGIHGVPAAKRNYILGLAIGITSVGYGIIDYETRDVIDAGVRLFKEANVENNEGRRSKR
GARRLKRRRRHRIQRVKKLLFDYNLLTDHSELSGINPYEARVKGLSQKLSEEEFSAALLHLAKRRGVH
NVNEVEEDTGNELSTKEQISRNSKALEEKYVAELQLERLKKDGEVRGSINRFKTSDYVKEAKQLLKV
QKAYHQLDQSFIDTYIDLLETRRTYYEGPGEGSPFGWKDIKEWYEMLMGHCTYFPEELRSVKYAYN
ADLYNALNDLNNLVITRDENEKLEYYEKFQIIENVFKQKKKPTLKQIAKEILVNEEDIKGYRVTSTGKP
EFTNLKVYHDIKDITARKEIIENAELLDQIAKILTIYQSSEDIQEELTNLNSELTQEEIEQISNLKGYTGTH
NLSLKAINLILDELWHTNDNQIAIFNRLKLVPKKVDLSQQKEIPTTLVDDFILSPVVKRSFIQSIKVINAI
IKKYGLPNDIIIELAREKNSKDAQKMINEMQKRNRQTNERIEEIIRTTGKENAKYLIEKIKLHDMQEG
KCLYSLEAIPLEDLLNNPFNYEVDHIIPRSVSFDNSFNNKVLVKQEEASKKGNRTPFQYLSSSDSKISY
ETFKKHILNLAKGKGRISKTKKEYLLEERDINRFSVQKDFINRNLVDTRYATRGLMNLLRSYFRVNNL
DVKVKSINGGFTSFLRRKWKFKKERNKGYKHHAEDALIIANADFIFKEWKKLDKAKKVMENQMFE
EKQAESMPEIETEQEYKEIFITPHQIKHIKDFKDYKYSHRVDKKPNRELINDTLYSTRKDDKGNTLIVN
NLNGLYDKDNDKLKKLINKSPEKLLMYHHDPQTYQKLKLIMEQYGDEKNPLYKYYEETGNYLTKYS
KKDNGPVIKKIKYYGNKLNAHLDITDDYPNSRNKVVKLSLKPYRFDVYLDNGVYKFVTVKNLDVIKK
ENYYEVNSKCYEEAKKLKKISNQAEFIASFYNNDLIKINGELYRVIGVNNDLLNRIEVNMIDITYREYL
ENMNDKRPPRIIKTIASKTQSIKKYSTDILGNLYEVKSKKHPQIIKKGKRPAATKKAGQAKKKKGSM
DAKSLTAWSRTLVTFKDVFVDFTREEWKLLDTAQQIVYRNVMLENYKNLVSLGYQLTKPDVILRLE
KGEEPGSGATNFSLLKQAGDVEENPGPTEYKPTVRLATRDDVPRAVRTLAAAFADYPATRHTVDP
DRHIERVTELQELFLTRVGLDIGKVWVADDGAAVAVWTTPESVEAGAVFAEIGPRMAELSGSRLA
AQQQMEGLLAPHRPKEPAWFLATVGVSPDHQGKGLGSAVVLPGVEAAERAGVPAFLETSAPRN
LPFYERLGFTVTADVEVPEGPRTWCMTRKPGA

Fig. 6-2

WT-dSaCas9-KRAB
NLS-WT-dSaCas9(D10A, N580A)-NLS-KRAB-P2A-Puro DNA sequence:

NLS | dsaCas9 (original) | KRAB-P2A-Puro

```
ATGGCCCCAAAGAAGAAGCGGAAGGTCGGTATCCACGGAGTCCCAGCAGCCAAGCGGAACTACATCCTGGGCCTGGCCATCG
GCATCACCAGCGTGGGCTACGGCATCATCGACTACGAGACACGGGACGTGATCGATGCCGGCGTGCGGCTGTTCAAAGAGGCC
AACGTGGAAAACAACGAGGGCAGGCGGAGCAAGAGAGGCGCCAGAAGGCTGAAGCGGCGGAGGCGGCATAGAATCCAGAG
AGTGAAGAAGCTGCTGTTCGACTACAACCTGCTGACCGACCACAGCGAGCTGAGCGGCATCAACCCCTACGAGGCCAGAGTGA
AGGGCCTGAGCCAGAAGCTGAGCGAGGAAGAGTTCTCTGCCGCCCTGCTGCACCTGGCCAAGAGAAGAGGCGTGCACAACGT
GAACGAGGTGGAAGAGGACACCGGCAACGAGCTGTCCACCAAAGAGCAGATCAGCCGGAACAGCAAGGCCCTGGAAGAGAA
ATACGTGGCCGAACTGCAGCTGGAACGGCTGAAGAAAGACGGCGAAGTGCGGGGCAGCATCAACAGATTCAAGACCAGCGAC
TACGTGAAAGAAGCCAAACAGCTGCTGAAGGTGCAGAAGGCCTACCACCAGCTGGACCAGAGCTTCATCGACACCTACATCGA
CCTGCTGGAAACCCGGCGGACCTACTATGAGGGACCTGGCGAGGGCAGCCCCTTCGGCTGGAAGGACATCAAAGAATGGTAC
GAGATGCTGATGGGCCACTGCACCTACTTCCCCGAGGAACTGCGGAGCGTGAAGTACGCCTACAACGCCGACCTGTACAACGC
CCTGAACGACCTGAACAATCTCGTGATCACCAGGGACGAGAACGAGAAGCTGGAATATTACGAGAAGTTCCAGATCATCGAGA
ACGTGTTCAAGCAGAAGAAGAAGCCCACCCTGAAGCAGATCGCCAAAGAAATCCTCGTGAACGAAGAGGATATTAAGGGCTAC
AGAGTGACCAGCACCGGCAAGCCCGAGTTCACCAACCTGAAGGTGTACCACGACATCAAGGACATTACCGCCCGGAAAGAGAT
TATTGAGAACGCCGAGCTGCTGGATCAGATTGCCAAGATCCTGACCATCTACCAGAGCAGCGAGGACATCCAGGAAGAACTGA
CCAATCTGAACTCCGAGCTGACCCAGGAAGAGATCGAGCAGATCTCTAATCTGAAGGGCTATACCGGCACCCACAACCTGAGCC
TGAAGGCCATCAACCTGATCCTGGACGAGCTGTGGCACACCAACGACAACCAGATCGCTATCTTCAACCGGCTGAAGCTGGTGC
CCAAGAAGGTGGACCTGTCCCAGCAGAAAGAGATCCCCACCACCCTGGTGGACGACTTCATCCTGAGCCCCGTCGTGAAGAGA
AGCTTCATCCAGAGCATCAAAGTGATCAACGCCATCATCAAGAAGTACGGCCTGCCCAACGACATCATTATCGAGCTGGCCCGC
GAGAAGAACTCCAAGGACGCCCAGAAAATGATCAACGAGATGCAGAAGCGGAACCGGCAGACCAACGAGCGGATCGAGGAA
ATCATCCGGACCACCGGCAAAGAGAACGCCAAGTACCTGATCGAGAAGATCAAGCTGCACGACATGCAGGAAGGCAAGTGCCT
GTACAGCCTGGAAGCCATCCCTCTGGAAGATCTGCTGAACAACCCCTTCAACTATGAGGTGGACCACATCATCCCCAGAAGCGT
GTCCTTCGACAACAGCTTCAACAACAAGGTGCTCGTGAAGCAGGAAGAAGCCAGCAAGAAGGGCAACCGGACCCCATTCCAGT
ACCTGAGCAGCAGCGACAGCAAGATCAGCTACGAAACCTTCAAGAAGCACATCCTGAATCTGGCCAAGGGCAAGGGCAGAATC
AGCAAGACCAAGAAAGAGTATCTGCTGGAAGAACGGGACATCAACAGGTTCTCCGTGCAGAAAGACTTCATCAACCGGAACCT
GGTGGATACCAGATACGCCACCAGAGGCCTGATGAACCTGCTGCGGAGCTACTTCAGAGTGAACAACCTGGACGTGAAAGTGA
AGTCCATCAATGGCGGCTTCACCAGCTTTCTGCGGCGGAAGTGGAAGTTTAAGAAAGAGCGGAACAAGGGGTACAAGCACCAC
GCCGAGGACGCCCTGATCATTGCCAACGCCGATTTCATCTTCAAAGAGTGGAAGAAACTGGACAAGGCCAAAAAAGTGATGGA
AAACCAGATGTTCGAGGAAAAGCAGGCCGAGAGCATGCCCGAGATCGAAACCGAGCAGGAGTACAAAGAGATCTTCATCACC
CCCCACCAGATCAAGCACATTAAGGACTTCAAGGACTACAAGTACAGCCACCGGGTGGACAAGAAGCCTAATAGAGAGCTGAT
TAACGACACCCTGTACTCCACCCGGAAGGACGACAAGGGCAACACCCTGATCGTGAACAATCTGAACGGCCTGTACGACAAGG
ACAATGACAAGCTGAAAAAGCTGATCAACAAGAGCCCCGAAAAGCTGCTGATGTACCACCACGACCCCCAGACCTACCAGAAA
CTGAAGCTGATTATGGAACAGTACGGCGACGAGAAGAATCCCCTGTACAAGTACTACGAGGAAACCGGGAACTACCTGACCAA
GTACTCCAAAAAGGACAACGGCCCCGTGATCAAGAAGATTAAGTATTACGGCAACAAACTGAACGCCCATCTGGACATCACCG
ACGACTACCCCAACAGCAGAAACAAGGTCGTGAAGCTGTCCCTGAAGCCCTACAGATTCGACGTGTACCTGGACAATGGCGTGT
ACAAGTTCGTGACCGTGAAGAATCTGGATGTGATCAAAAAAGAAAACTACTACGAAGTGAATAGCAAGTGCTATGAGGAAGCT
AAGAAGCTGAAGAAGATCAGCAACCAGGCCGAGTTTATCGCCTCCTTCTACAACAACGATCTGATCAAGATCAACGGCGAGCTG
TATAGAGTGATCGGCGTGAACAACGACCTGCTGAACCGGATCGAAGTGAACATGATCGACATCACCTACCGCGAGTACCTGGA
AAACATGAACGACAAGAGGCCCCCAGGATCATTAAGACAATCGCCTCCAAGACCCAGAGCATTAAGAAGTACAGCACAGACA
TTCTGGGCAACCTGTATGAAGTGAAATCTAAGAAGCACCCTCAGATCATCAAAAAGGGCAAAAGGCCGGCGGCCACGAAAAA
GGCCGGCCAGGCAAAAAGAAAAAGGGATCCATGGATGCTAAGTCACTAACTGCCTGGTCCCGGACACTGGTGACCTTCAAG
GATGTATTTGTGGACTTCACCAGGGAGGAGTGGAAGCTGCTGGACACTGCTCAGCAGATCGTGTACAGAAATGTGATGCTGGA
GAACTATAAGAACCTGGTTTCCTTGGGTTATCAGCTTACTAAGCCAGATGTGATCCTCCGGTTGGAGAAGGGAGAAGAGCCCG
GAAGCGGTGCTACTAACTTCAGCCTGCTGAAGCAGGCTGGAGACGTGGAGGAGAACCCTGGACCTACCGAGTACAAGCCCACG
GTGCGCCTCGCCACCCGCGACGACGTCCCCAGGGCCGTACGCACCCTCGCCGCCGCGTTCGCCGACTACCCCGCCACGCGCCAG
ACCGTCGATCCGGACCGCCACATCGAGCGGGTCACCGAGCTGCAAGAACTCTTCCTCACGCGCGTCGGGCTCGACATCGGCAA
GGTGTGGGTCGCGGACGACGGCGCCGCGGTGGCGGTCTGGACCACCGCGGAGAGCGTCGAAGCGGGGCGGTGTTCGCCGA
GATCGGCCCGCGCATGGCCGAGTTGAGCGGTTCCCGGCTGGCCGCGCAGCAACAGATGGAAGGCCTCCTGGCGCCGCACCGG
CCCAAGGAGCCCGCGTGGTTCCTGGCCACCGTCGGAGTCTCGCCCGACCACCAGGGCAAGGTCTGGGCAGCGCCGTCGTGCT
CCCCGGAGTGGAGGCGGCCGAGCGCGCCGGGGTGCCCGCCTTCCTGGAAACCTCCGCGCCCCGCAACCTCCCCTTCTACGAGC
GGCTCGGCTTCACCGTCACCGCCGACGTCGAGGTGCCCGAAGGACCGCGCACCTGGTGCATGACCCGCAAGCCCGGTGCCTGA
```

Fig. 7-1

PF(v15)-dSaCas9-KRAB
NLS-PF(v15)-dSaCas9(D10A, N580A)-NLS-KRAB-P2A-Puro fusion protein sequence:

NLS        dsaCas9 (v15)            KRAB-P2A-Puro
MAPKKKRKVGIHGVPAAKRNYILGLAIGITSVGYGIIDYETRDVIDAGVRLFKEANVENNEGRRSKR
GARRLKRRRRHRIQRVKKLLFDYNLLTDHSELSGINPYEARVKGLSQKLSEEEFSAALLHLAKRRGVH
NVNEVEEDTGNELSTKEQISRNSKALEEKYVAELQLERLKKDGEVRGSINRFKTSDYVKEAKQLLKV
QKAYHQLDQSFIDTYIDLLETRRTYYEGPGEGSPFGWKDIKEWYEMLMGHCTYFPEELRSVKYAYN
ADLYNALNDLNNLVITRDENEKLEYYEKFQIIENVFKQKKKPTLKQIAKEILVNEEDIKGYRVTSTGKP
EFTNLKVYHDIKDITARKEIIENAELLDQIAKILTIYQSSEDIQEELTNLNSELTQEEIEQISNLKGYTGTH
NLSLKAINLILDELWHTNDNQIAIFNRLKLVPKKVDLSQQKEIPTTLVDDFILSPVVKRSFIQSIKVINAI
IKKYGLPNDIIIELAREKNSKDAQKMINEMQKRNRQTNERIEEIIRTTGKENAKYLIEKIKLHDMQEG
KCLYSLEAIPLEDLLNNPFNYEVDHIIPRSVSFDNSFNNKVLVKQEEASKKGNRTPFQYLSSSDSKISY
ETFKKHILNLAKGKGRISKTKKEYLLEERDINRFSVQKDFINRNLVDTRYATRGLMNLLRSYFRVNNL
DVKVKSINGGFTSFLRRKWKFKKERNKGYKHHAEDALIIANADFIFKEWKKLDKAKKVMENQMFE
EKQAESMPEIETEQEYKEIFITPHQIKHIKDFKDYKYSHRVDKKPNRKLINDTLYSTRKDDKGNTRIV
NNLNGLYDKDNDKLKKLINKSPEKLLMYHHDPQTYQKLKLIMEQYGDEKNPLYKYYEETGNYLTKY
SKKDNGPVIKKIKYYGNKLNRHLDITDDYPNSRNKVVKLSLKPYRFDVYLDNGVYKFVTVKNLDVIK
KENYYEVNSKCYEEAKKLKKISNQAEFIASFYRNDLIKINGELYRVIGVAADHLNAIEVNMIDITYREY
LENMNDKRPPRIIKTISSKTQSIKKYSTDILGNLYEVKSKKHPQIIKKGKRPAATKKAGQAKKKKGSM
DAKSLTAWSRTLVTFKDVFVDFTREEWKLLDTAQQIVYRNVMLENYKNLVSLGYQLTKPDVILRLF
KGEEPGSGATNFSLLKQAGDVEENPGPTEYKPTVRLATRDDVPRAVRTLAAAFADYPATRHTVDP
DRHIERVTELQELFLTRVGLDIGKVWVADDGAAVAVWTTPESVEAGAVFAEIGPRMAELSGSRLA
AQQQMFGLLAPHRPKEPAWFLATVGVSPDHQGKGLGSAVVLPGVEAAERAGVPAFLETSAPRN
LPFYERLGFTVTADVEVPEGPRTWCMTRKPGA

Fig. 7-2

PF(v15)-dSaCas9-KRAB

NLS-PF(v15)-dSaCas9(D10A, N580A)-NLS-KRAB-P2A-Puro DNA sequence:

```
NLS      dsaCas9 (v15)              KRAB-P2A-Puro
ATGGCCCCAAAGAAGAAGCGGAAGGTCGGTATCCACGGAGTCCCAGCAGCCAAGCGGAACTACATCCTGGGCCTGGCCATCG
GCATCACCAGCGTGGGCTACGGCATCATCGACTACGAGACACGGGACGTGATCGATGCCGGCGTGCGGCTGTTCAAAGAGGCC
AACGTGGAAAACAACGAGGGCAGGCGGAGCAAGAGAGGCGCCAGAAGGCTGAAGCGGCGGAGGCGGCATAGAATCCAGAG
AGTGAAGAAGCTGCTGTTCGACTACAACCTGCTGACCGACCACAGCGAGCTGAGCGGCATCAACCCCTACGAGGCAGAGTGA
AGGGCCTGAGCCAGAAGCTGAGCGAGGAAGAGTTCTCTGCCGCCCTGCTGCACCTGGCCAAGAGAAGAGGCGTGCACAACGT
GAACGAGGTGGAAGAGGACACCGGCAACGAGCTGTCCACCAAAGAGCAGATCAGCCGGAACAGCAAGGCCCTGGAAGAGAA
ATACGTGGCCGAACTGCAGCTGGAACGGCTGAAGAAAGACGGCGAAGTGCGGGGCAGCATCAACAGATTCAAGACCAGCGAC
TACGTGAAAGAAGCCAAACAGCTGCTGAAGGTGCAGAAGGCCTACCACCAGCTGGACCAGAGCTTCATCGACACCTACATCGA
CCTGCTGGAAACCCGGCGGACCTACTATGAGGGACCTGGCGAGGGCAGCCCCTTCGGCTGGAAGGACATCAAAGAATGGTAC
GAGATGCTGATGGGCCACTGCACCTACTTCCCCGAGGAACTGCGGAGCGTGAAGTACGCCTACAACGCCGACCTGTACAACGC
CCTGAACGACCTGAACAATCTCGTGATCACCAGGGACGAGAACGAGAAGCTGGAATATTACGAGAAGTTCCAGATCATCGAGA
ACGTGTTCAAGCAGAAGAAGAAGCCCACCCTGAAGCAGATCGCCAAAGAAATCCTCGTGAACGAAGAGGATATTAAGGGCTAC
AGAGTGACCAGCACCGGCAAGCCCGAGTTCACCAACCTGAAGGTGTACCACGACATCAAGGACATTACCGCCCGGAAAGAGAT
TATTGAGAACGCCGAGCTGCTGGATCAGATTGCCAAGATCCTGACCATCTACCAGAGCAGCGAGGACATCCAGGAAGAACTGA
CCAATCTGAACTCCGAGCTGACCCAGGAAGAGATCGAGCAGATCTCTAATCTGAAGGGCTATACCGGCACCCACAACCTGAGCC
TGAAGGCCATCAACCTGATCCTGGACGAGCTGTGGCACACCAACGACAACCAGATCGCTATCTTCAACCGGCTGAAGCTGGTGC
CCAAGAAGGTGGACCTGTCCCAGCAGAAAGAGATCCCCACCACCCTGGTGGACGACTTCATCCTGAGCCCCGTCGTGAAGAGA
AGCTTCATCCAGAGCATCAAAGTGATCAACGCCATCATCAAGAAGTACGGCCTGCCCAACGACATCATTATCGAGCTGGCCCGC
GAGAAGAACTCCAAGGACGCCCAGAAAATGATCAACGAGATGCAGAAGCGGAACCGGCAGACCAACGAGCGGATCGAGGAA
ATCATCCGGACCACCGGCAAAGAGAACGCCAAGTACCTGATCGAGAAGATCAAGCTGCACGACATGCAGGAAGGCAAGTGCCT
GTACAGCCTGGAAGCCATCCCTCTGGAAGATCTGCTGAACAACCCCTTCAACTATGAGGTGGACCACATCATCCCCAGAAGCGT
GTCCTTCGACAACAGCTTCAACAACAAGGTGCTCGTGAAGCAGGAAGAAGCCAGCAAGAAGGGCAACCGGACCCCATTCCAGT
ACCTGAGCAGCAGCGACAGCAAGATCAGCTACGAAACCTTCAAGAAGCACATCCTGAATCTGGCCAAGGGCAAGGGCAGAATC
AGCAAGACCAAGAAAGAGTATCTGCTGGAAGAACGGGACATCAACAGGTTCTCCGTGCAGAAAGACTTCATCAACCGGAACCT
GGTGGATACCAGATACGCCACCAGAGGCCTGATGAACCTGCTGCGGAGCTACTTCAGAGTGAACAACCTGGACGTGAAAGTGA
AGTCCATCAATGGCGGCTTCACCAGCTTTCTGCGGCGGAAGTGGAAGTTTAAGAAAGAGCGGAACAAGGGGTACAAGCACCAC
GCCGAGGACGCCCTGATCATTGCCAACGCCGATTTCATCTTCAAAGAGTGGAAGAAACTGGACAAGGCCAAAAAAGTGATGGA
AAACCAGATGTTCGAGGAAAAGCAGGCCGAGAGCATGCCCGAGATCGAAACCGAGCAGGAGTACAAAGAGATCTTCATCACC
CCCCACCAGATCAAGCACATTAAGGACTTCAAGGACTACAAGTACAGCCACCGGGTGGACAAGAAGCCTAATAGAAAGCTGAT
TAACGACACCCTGTACTCCACCCGGAAGGACGACAAGGGCAACACCCGGATCGTGAACAATCTGAACGGCCTGTACGACAAGG
ACAATGACAAGCTGAAAAAGCTGATCAACAAGAGCCCCGAAAAGCTGCTGATGTACCACCACGACCCCCAGACCTACCAGAA
CTGAAGCTGATTATGGAACAGTACGGCGACGAGAAGAATCCCCTGTACAAGTACTACGAGGAAACCGGGAACTACCTGACCAA
GTACTCCAAAAAGGACAACGGCCCCGTGATCAAGAAGATTAAGTATTACGGCAACAAACTGAACAGACATCTGGACATCACCG
ACGACTACCCCAACAGCGAAAACAAGGTCGTGAAGCTGTCCCTGAAGCCCTACAGATTCGACGTGTACCTGGACAATGGCGTGT
ACAAGTTCGTGACCGTGAAGAATCTGGATGTGATCAAAAAAGAAAACTACTACGAAGTGAATAGCAAGTGCTATGAGGAAGCT
AAGAAGCTGAAGAAGATCAGCAACCAGGCCGAGTTTATCGCCTCCTTCTACAGAAACGATCTGATCAAGATCAACGGCGAGCT
GTATAGAGTGATCGGCGTGGCGGCCGACCACCTGAACGCCATCGAAGTGAACATGATCGACATCACCTACCGCGAGTACCTGG
AAAACATGAACGACAAGAGGCCCCCCAGGATCATTAAGACAATCAGCTCCAAGACCCAGAGCATTAAGAAGTACAGCACAGAC
ATTCTGGGCAACCTGTATGAAGTGAAATCTAAGAAGCACCCTCAGATCATCAAAAAGGGCAAAAGGCCGGCGGCCACGAAAAA
GGCCGGCCAGGCAAAAAAGAAAAAGGGATCCATGGATGCTAAGTCACTAACTGCCTGGTCCCGGACACTGGTGACCTTCAAG
GATGTATTTGTGGACTTCACCAGGGAGGAGTGGAAGCTGCTGGACACTGCTCAGCAGATCGTGTACAGAAATGTGATGCTGGA
GAACTATAAGAACCTGGTTTCCTTGGGTTATCAGCTTACTAAGCCAGATGTGATCCTCCGGTTGGAGAAGGGAGAAGAGCCCG
GAAGCGGTGCTACTAACTTCAGCCTGCTGAAGCAGGCTGGAGACGTGGAGGAGAACCCTGGACCTACCGGAGTACAAGCCACG
GTGCGCCTCGCCACCCGCGACGACGTCCCCAGGGCCGTACGCACCCTCGCCGCCGCCGTTCGCCGACTACCCCGCCACGCGCCAC
ACCGTCGATCCGGACCGCCACATCGAGCGGGTCACCGAGCTGCAAGAACTCTTCCTCACGCGCGTCGGGCTCGACATCGGCAA
GGTGTGGGTCGCCGGACGACGGGCCGGTGGCGGTCTGGACCACGCCGGAGAGCGTCGAAGCGGGGCGGTGTTCGCCGA
GATCGGCCGCGCATGGCCGAGTTGAGCGGTTCCCGGCTGGCCGCGCAGCAACAGATGGAAGGCCTCCTGGCGCCGCACCGG
CCCAAGGAGCCCGCGTGGTTCCTGGCCACCGTCGGAGTCTCGCCCGACCACCAGGGCAAGGGTCTGGGCAGCGCCGTCGTGCT
CCCCGGAGTGGAGGCGGCCGAGCGCGCCGGGGTGCCCGCCTTCCTGGAAACCTCGCGCGCCCGCAACCTCCCCTTCTACGAGC
GGCTCGGCTTCACCGTCACCGCCGACGTCGAGGTGCCCGAAGGACCGCGCACCTGGTGCATGACCCGCAAGCCCGGTGCCTGA
```

Fig. 8-1

PF(v51)-dSaCas9-KRAB
NLS-PF(v51)-dSaCas9(D10A, N580A)-NLS-KRAB-P2A-Puro fusion protein sequence:

NLS — dsaCas9 (v51) — KRAB-P2A-Puro

MAPKKKRKVGIHGVPAAKRNYILGLAIGITSVGYGIIDYETRDVIDAGVRLFKEANVENNEGRRSKR
GARRLKRRRRHRIQRVKKLLFDYNLLTDHSELSGINPYEARVKGLSQKLSEEEFSAALLHLAKRRGVH
NVNEVEEDTGNELSTKEQISRNSKALEEKYVAELQLERLKKDGEVRGSINRFKTSDYVKEAKQLLKV
QKAYHQLDQSFIDTYIDLLETRRTYYEGPGEGSPFGWKDIKEWYEMLMGHCTYFPEELRSVKYAYN
ADLYNALNDLNNLVITRDENEKLEYYEKFQIIENVFKQKKKPTLKQIAKEILVNEEDIKGYRVTSTGKP
EFTNLKVYHDIKDITARKEIIENAELLDQIAKILTIYQSSEDIQEELTNLNSELTQEEIEQISNLKGYTGTH
NLSLKAINLILDELWHTNDNQIAIFNRLKLVPKKVDLSQQKEIPTTLVDDFILSPVVKRSFIQSIKVINAI
IKKYGLPNDIIIELAREKNSKDAQKMINEMQKRNRQTNERIEEIIRTTGKENAKYLIEKIKLHDMQEG
KCLYSLEAIPLEDLLNNPFNYEVDHIIPRSVSFDNSFNNKVLVKQEEASKKGNRTPFQYLSSSDSKISY
ETFKKHILNLAKGKGRISKTKKEYLLEERDINRFSVQKDFINRNLVDTRYATRGLMNLLRSYFRVNNL
DVKVKSINGGFTSFLRRKWKFKKERNKGYKHHAEDALIIANADFIFKEWKKLDKAKKVMENQMFE
EKQAESMPEIETEQEYKEIFITPHQIKHIKDFKDYKYSHRVDKKPNRKLINDTLYSTRKDDKGNTRIV
NNLNGLYDKDNDKLKKLINKSPEKLLMYHHDPQTYQKLKLIMEQYGDEKNPLYKYYEETGNYLTKY
SKKDNGPVIKKIKYYGNKLNAHLDITDDYPNSRNKVVKLSLKPYRFDVYLDNGVYKFVKVNNLDVIK
KENYYEVNSKCYEEAKKLKKISNQAEFIASFYRNDLIKINGELYRVIGVANDLLNAIEVNMIDITYREYL
ENMNDKRPPRIFKTISSKTQSIKKYSTDILGNLYEVKSKKHPQIIKKGKRPAATKKAGQAKKKKGSM
DAKSLTAWSRTLVTFKDVFVDFTREEWKLLDTAQQIVYRNVMLENYKNLVSLGYQLTKPDVILRLE
KGEEPGSGATNFSLLKQAGDVEENPGPTEYKPTVRLATRDDVPRAVRTLAAAFADYPATRHTVDP
DRHIERVTELQELFLTRVGLDIGKVWVADDGAAVAVWTTPESVEAGAVFAEIGPRMAELSGSRLA
AQQQMEGLLAPHRPKEPAWFLATVGVSPDHQGKGLGSAVVLPGVEAAERAGVPAFLETSAPRN
LPFYERLGFTVTADVEVPEGPRTWCMTRKPGA

Fig. 8-2

PF(v51)-dSaCas9-KRAB
NLS-PF(v51)-dSaCas9(D10A, N580A)-NLS-KRAB-P2A-Puro DNA sequence:

```
NLS        dsaCas9 (v51)              KRAB-P2A-Puro
ATGGCCCCAAAGAAGAAGCGGAAGGTCGGTATCCACGGAGTCCCAGCAGCCAAGCGGAACTACATCCTGGGCCTGGCCATCG
GCATCACCAGCGTGGGCTACGGCATCATCGACTACGAGACACGGGACGTGATCGATGCCGGCGTGCGGCTGTTCAAAGAGGCC
AACGTGGAAAACAACGAGGGCAGGCGGAGCAAGAGAGGCGCCAGAAGGCTGAAGCGGCGGAGGCGGCATAGAATCCAGAG
AGTGAAGAAGCTGCTGTTCGACTACAACCTGCTGACCGACCACAGCGAGCTGAGCGGCATCAACCCCTACGAGGCCAGAGTGA
AGGGCCTGAGCCAGAAGCTGAGCGAGGAAGAGTTCTCTGCCGCCCTGCTGCACCTGGCCAAGAGAAGAGGCGTGCACAACGT
GAACGAGGTGGAAGAGGACACCGGCAACGAGCTGTCCACCAAAGAGCAGATCAGCCGGAACAGCAAGGCCCTGGAAGAGAA
ATACGTGGCCGAACTGCAGCTGGAACGGCTGAAGAAAGACGGCGAAGTGCGGGGCAGCATCAACAGATTCAAGACCAGCGAC
TACGTGAAAGAAGCCAAACAGCTGCTGAAGGTGCAGAAGGCCTACCACCAGCTGGACCAGAGCTTCATCGACACCTACATCGA
CCTGCTGGAAACCCGGCGGACCTACTATGAGGGACCTGGCGAGGGCAGCCCCTTCGGCTGGAAGGACATCAAAGAATGGTAC
GAGATGCTGATGGGCCACTGCACCTACTTCCCCGAGGAACTGCGGAGCGTGAAGTACGCCTACAACGCCGACCTGTACAACGC
CCTGAACGACCTGAACAATCTCGTGATCACCAGGGACGAGAACGAGAAGCTGGAATATTACGAGAAGTTCCAGATCATCGAGA
ACGTGTTCAAGCAGAAGAAGAAGCCCACCCTGAAGCAGATCGCCAAAGAAATCCTCGTGAACGAAGAGGATATTAAGGGCTAC
AGAGTGACCAGCACCGGCAAGCCCGAGTTCACCAACCTGAAGGTGTACCACGACATCAAGGACATTACCGCCCGGAAAGAGAT
TATTGAGAACGCCGAGCTGCTGGATCAGATTGCCAAGATCCTGACCATCTACCAGAGCAGCGAGGACATCCAGGAAGAACTGA
CCAATCTGAACTCCGAGCTGACCCAGGAAGAGATCGAGCAGATCTCTAATCTGAAGGGCTATACCGGCACCCACAACCTGAGCC
TGAAGGCCATCAACCTGATCCTGGACGAGCTGTGGCACACCAACGACAACCAGATCGCTATCTTCAACCGGCTGAAGCTGGTGC
CCAAGAAGGTGGACCTGTCCCAGCAGAAAGAGATCCCCACCACCCTGGTGGACGACTTCATCCTGAGCCCCGTCGTGAAGAGA
AGCTTCATCCAGAGCATCAAAGTGATCAACGCCATCATCAAGAAGTACGGCCTGCCCAACGACATCATTATCGAGCTGGCCCGC
GAGAAGAACTCCAAGGACGCCCAGAAAATGATCAACGAGATGCAGAAGCGGAACCGGCAGACCAACGAGCGGATCGAGGAA
ATCATCCGGACCACCGGCAAAGAGAACGCCAAGTACCTGATCGAGAAGATCAAGCTGCACGACATGCAGGAAGGCAAGTGCCT
GTACAGCCTGGAAGCCATCCCTCTGGAAGATCTGCTGAACAACCCCTTCAACTATGAGGTGGACCACATCATCCCCAGAAGCGT
GTCCTTCGACAACAGCTTCAACAACAAGGTGCTCGTGAAGCAGGAAGAAGCCAGCAAGAAGGGCAACCGGACCCCATTCCAGT
ACCTGAGCAGCAGCGACAGCAAGATCAGCTACGAAACCTTCAAGAAGCACATCCTGAATCTGGCCAAGGGCAAGGGCAGAATC
AGCAAGACCAAGAAAGAGTATCTGCTGGAAGAACGGGACATCAACAGGTTCTCCGTGCAGAAAGACTTCATCAACCGGAACCT
GGTGGATACCAGATACGCCACCAGAGGCCTGATGAACCTGCTGCGGAGCTACTTCAGAGTGAACAACCTGGACGTGAAAGTGA
AGTCCATCAATGGCGGCTTCACCAGCTTTCTGCGGCGGAAGTGGAAGTTTAAGAAAGAGCGGAACAAGGGGTACAAGCACCAC
GCCGAGGACGCCCTGATCATTGCCAACGCCGATTTCATCTTCAAAGAGTGGAAGAAACTGGACAAGGCCAAAAAAGTGATGGA
AAACCAGATGTTCGAGGAAAAGCAGGCCGAGAGCATGCCCGAGATCGAAACCGAGCAGGAGTACAAAGAGATCTTCATCACC
CCCCACCAGATCAAGCACATTAAGGACTTCAAGGACTACAAGTACAGCCACCGGGTGGACAAGAAGCCTAATAGAAAACTGAT
TAACGACACCCTGTACTCCACCCGGAAGGACGACAAGGGCAACACCCGGATCGTGAACAATCTGAACGGCCTGTACGACAAGG
ACAATGACAAGCTGAAAAAGCTGATCAACAAGAGCCCCGAAAAGCTGCTGATGTACCACCACGACCCCCAGACCTACCAGAAA
CTGAAGCTGATTATGGAACAGTACGGCGACGAGAAGAATCCCCTGTACAAGTACTACGAGGAAACCGGGAACTACCTGACCAA
GTACTCCAAAAAGGACAACGGCCCCGTGATCAAGAAGATTAAGTATTACGGCAACAAACTGAACGCCCATCTGGACATCACCG
ACGACTACCCCAACAGCAGAAACAAGGTCGTGAAGCTGTCCCTGAAGCCCTACAGATTCGACGTGTACCTGGACAATGGCGTGT
ACAAGTTCGTGAAGGTGAATAATCTGGATGTGATCAAAAAAGAAAACTACTACGAAGTGAATAGCAAGTGCTATGAGGAAGCT
AAGAAGCTGAAGAAGATCAGCAACCAGGCCGAGTTTATCGCCTCCTTCTACAGAAACGATCTGATCAAGATCAACGGCGAGCT
GTATAGAGTGATCGGCGTGGCCAACGACCTGCTGAACGCCATCGAAGTGAACATGATCGACATCACCTACCGCGAGTACCTGG
AAAACATGAACGACAAGAGGCCCCCCAGGATCTTCAAGACAATCTCCTCCAAGACCCAGAGCATTAAGAAGTACAGCACAGAC
ATTCTGGGCAACCTGTATGAAGTGAAATCTAAGAAGCACCCTCAGATCATCAAAAAGGGCAAAAGGCCGGCGGCCACGAAAAA
GGCCGGCCAGGCAAAAAAGAAAAAGGGATCCATGGATGCTAAGTCACTAACTGCCTGGTCCCGGACACTGGTGACCTTCAAG
GATGTATTTGTGGACTTCACCAGGGAGGAGTGGAAGCTGCTGGACACTGCTCAGCAGATCGTGTACAGAAATGTGATGCTGGA
GAACTATAAGAACCTGGTTTCCTTGGGTTATCAGCTTACTAAGCCAGATGTGATCCTCCGGTTGGAGAAGGGAGAAGAGCCCG
GAAGCGGTGCTACTAACTTCAGCCTGCTGAAGCAGGCTGGAGACGTGGAGGAGAACCCTGGACCTACCGAGTACAAGCCCACG
GTGCGCCTCGCCGACGGCGACGTCCCCAGGGCCGTACGCACCCTGCCGCCGCGTTCGCCGACTACCCCGCCACGCCGCCAC
ACCGTCGATCCGGACCGCCACATCGAGCGGGTCACCGAGCTGCAAGAACTCTTCCTCACGCGCGTCGGGCTCGACATCGGCAA
GGTGTGGGTCGCGGACGACGGCGCCGCGGTGGCGGTCTGGACCACGCCGGAGAGCGTCGAAGCGGGGGCGGTGTTCGCCGA
GATCGGCCCGCGCATGGCCGAGTTGAGCGGTTCCCGGCTGGCCGCGCAGCAACAGATGGAAGGCCTCCTGGCGCCGGACCGG
CCCAAGGAGCCGCGTGGTTCCTGGCCACCGTCGGAGTCTCGCCCGACCACCAGGGCAAGGGTCTGGGCAGCGCCGTCGTGCT
CCCCGGAGTGGAGGCGGCCGAGCGCGCCGGGGTGCCCGCCTTCCTGGAAACCTCCGCGCCCCGCAACCTCCCCTTCTACGAGC
GGCTCGGCTTCACCGTCACCGCCGACGTCGAGGTGCCCGAAGGACCGCGCACCTGGTGCATGACCCGCAAGCCCGGTGCCTGA
```

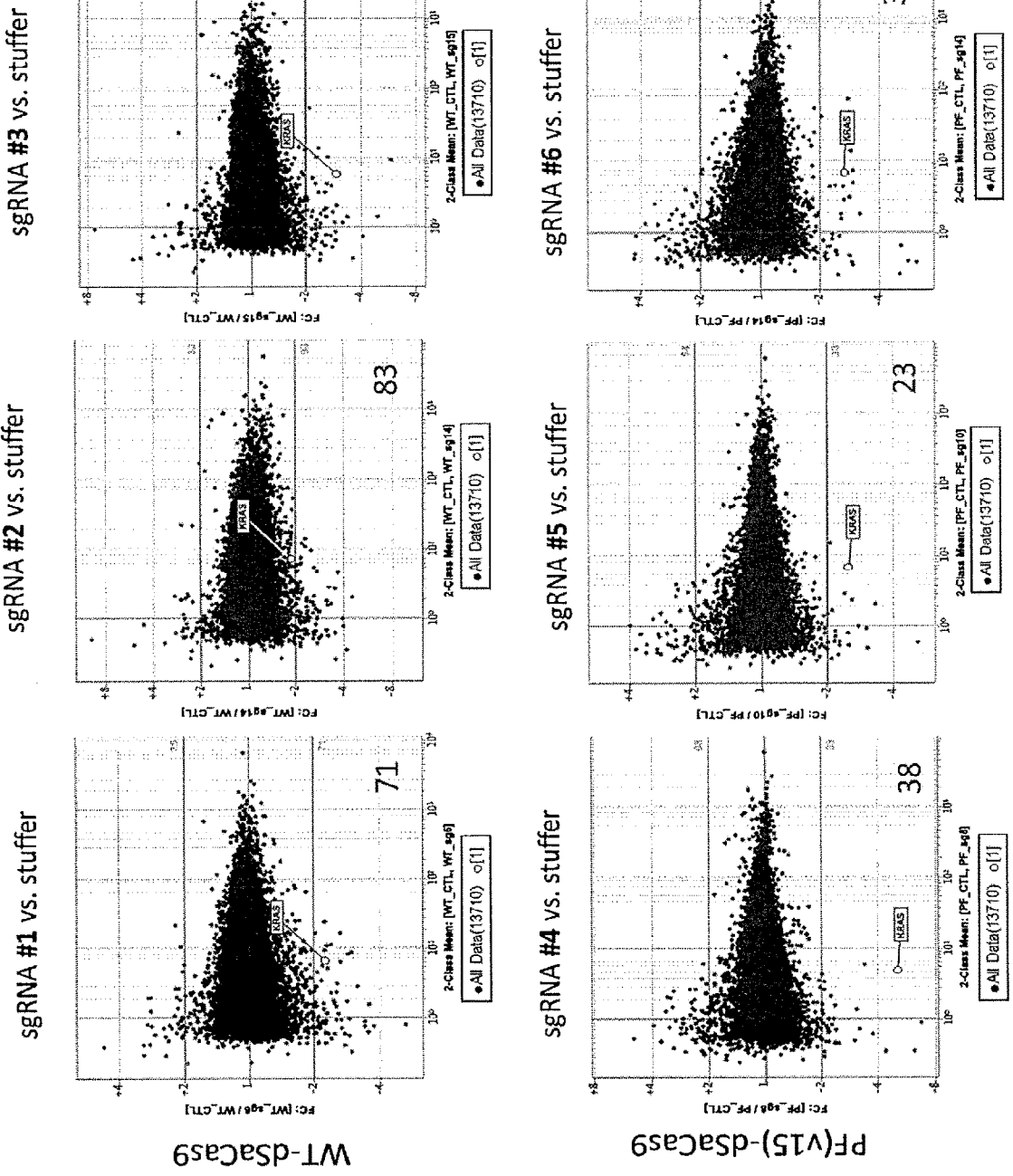

```
SEQUENCE LISTING

<160> NUMBER OF SEQ ID NOS: 52

<210> SEQ ID NO 1
<211> LENGTH: 3162
<212> TYPE: DNA
<213> ORGANISM: Staphylococcus aureus
<220> FEATURE:
<221> NAME/KEY: CDS
<222> LOCATION: (1)..(3162)

<400> SEQUENCE: 1 atg aaa agg aac tac att ctg ggg ctg gac atc ggg att aca agc gtg      48
Met Lys Arg Asn Tyr Ile Leu Gly Leu Asp Ile Gly Ile Thr Ser Val
1               5                   10                  15 ggg tat ggg att att gac tat gaa aca agg gac gtg atc gac gca ggc      96
Gly Tyr Gly Ile Ile Asp Tyr Glu Thr Arg Asp Val Ile Asp Ala Gly
            20                  25                  30 gtc aga ctg ttc aag gag gcc aac gtg gaa aac aat gag gga cgg aga     144
Val Arg Leu Phe Lys Glu Ala Asn Val Glu Asn Asn Glu Gly Arg Arg
        35                  40                  45 agc aag agg gga gcc agg cgc ctg aaa cga cgg aga agg cac aga atc     192
Ser Lys Arg Gly Ala Arg Arg Leu Lys Arg Arg Arg His Arg Ile
    50                  55                  60 cag agg gtg aag aaa ctg ctg ttc gat tac aac ctg ctg acc gac cat     240
Gln Arg Val Lys Lys Leu Leu Phe Asp Tyr Asn Leu Leu Thr Asp His
65                  70                  75                  80 tct gag ctg agt gga att aat cct tat gaa gcc agg gtg aaa ggc ctg     288
Ser Glu Leu Ser Gly Ile Asn Pro Tyr Glu Ala Arg Val Lys Gly Leu
                85                  90                  95 agt cag aag ctg tca gag gaa gag ttt tcc gca gct ctg ctg cac ctg     336
Ser Gln Lys Leu Ser Glu Glu Glu Phe Ser Ala Ala Leu Leu His Leu
            100                 105                 110 gct aag cgc cga gga gtg cat aac gtc aat gag gtg gaa gag gac acc     384
Ala Lys Arg Arg Gly Val His Asn Val Asn Glu Val Glu Glu Asp Thr
        115                 120                 125 ggc aac gag ctg tct aca aag gaa cag atc tca cgc aat agc aaa gct     432
Gly Asn Glu Leu Ser Thr Lys Glu Gln Ile Ser Arg Asn Ser Lys Ala
    130                 135                 140 ctg gaa gag aag tat gtc gca gag ctg cag ctg gaa cgg ctg aag aaa     480
Leu Glu Glu Lys Tyr Val Ala Glu Leu Gln Leu Glu Arg Leu Lys Lys
145                 150                 155                 160 gat ggc gag gtg aga ggg tca att aat agg ttc aag aca agc gac tac     528
Asp Gly Glu Val Arg Gly Ser Ile Asn Arg Phe Lys Thr Ser Asp Tyr
                165                 170                 175 gtc aaa gaa gcc aag cag ctg ctg aaa gtg cag aag gct tac cac cag     576
```

```
Val Lys Glu Ala Lys Gln Leu Leu Lys Val Gln Lys Ala Tyr His Gln
            180                 185                 190 ctg gat cag agc ttc atc gat act tat atc gac ctg ctg gag act cgg     624
Leu Asp Gln Ser Phe Ile Asp Thr Tyr Ile Asp Leu Leu Glu Thr Arg
        195                 200                 205 aga acc tac tat gag gga cca gga gaa ggg agc ccc ttc gga tgg aaa     672
Arg Thr Tyr Tyr Glu Gly Pro Gly Glu Gly Ser Pro Phe Gly Trp Lys
210                 215                 220 gac atc aag gaa tgg tac gag atg ctg atg gga cat tgc acc tat ttt     720
Asp Ile Lys Glu Trp Tyr Glu Met Leu Met Gly His Cys Thr Tyr Phe
225                 230                 235                 240 cca gaa gag ctg aga agc gtc aag tac gct tat aac gca gat ctg tac     768
Pro Glu Glu Leu Arg Ser Val Lys Tyr Ala Tyr Asn Ala Asp Leu Tyr
                245                 250                 255 aac gcc ctg aat gac ctg aac aac ctg gtc atc acc agg gat gaa aac     816
Asn Ala Leu Asn Asp Leu Asn Asn Leu Val Ile Thr Arg Asp Glu Asn
                260                 265                 270 gag aaa ctg gaa tac tat gag aag ttc cag atc atc gaa aac gtg ttt     864
Glu Lys Leu Glu Tyr Tyr Glu Lys Phe Gln Ile Ile Glu Asn Val Phe
            275                 280                 285 aag cag aag aaa aag cct aca ctg aaa cag att gct aag gag atc ctg     912
Lys Gln Lys Lys Lys Pro Thr Leu Lys Gln Ile Ala Lys Glu Ile Leu
        290                 295                 300 gtc aac gaa gag gac atc aag ggc tac cgg gtg aca agc act gga aaa     960
Val Asn Glu Glu Asp Ile Lys Gly Tyr Arg Val Thr Ser Thr Gly Lys
305                 310                 315                 320 cca gag ttc acc aat ctg aaa gtg tat cac gat att aag gac atc aca    1008
Pro Glu Phe Thr Asn Leu Lys Val Tyr His Asp Ile Lys Asp Ile Thr
                325                 330                 335 gca cgg aaa gaa atc att gag aac gcc gaa ctg ctg gat cag att gct    1056
Ala Arg Lys Glu Ile Ile Glu Asn Ala Glu Leu Leu Asp Gln Ile Ala
                340                 345                 350 aag atc ctg act atc tac cag agc tcc gag gac atc cag gaa gag ctg    1104
Lys Ile Leu Thr Ile Tyr Gln Ser Ser Glu Asp Ile Gln Glu Glu Leu
            355                 360                 365 act aac ctg aac agc gag ctg acc cag gaa gag atc gaa cag att agt    1152
Thr Asn Leu Asn Ser Glu Leu Thr Gln Glu Glu Ile Glu Gln Ile Ser
        370                 375                 380 aat ctg aag ggg tac acc gga aca cac aac ctg tcc ctg aaa gct atc    1200
Asn Leu Lys Gly Tyr Thr Gly Thr His Asn Leu Ser Leu Lys Ala Ile
385                 390                 395                 400 aat ctg att ctg gat gag ctg tgg cat aca aac gac aat cag att gca    1248
Asn Leu Ile Leu Asp Glu Leu Trp His Thr Asn Asp Asn Gln Ile Ala
                405                 410                 415 atc ttt aac cgg ctg aag ctg gtc cca aaa aag gtg gac ctg agt cag    1296
Ile Phe Asn Arg Leu Lys Leu Val Pro Lys Lys Val Asp Leu Ser Gln
                420                 425                 430 cag aaa gag atc cca acc aca ctg gtg gac gat ttc att ctg tca ccc    1344
Gln Lys Glu Ile Pro Thr Thr Leu Val Asp Asp Phe Ile Leu Ser Pro
            435                 440                 445 gtg gtc aag cgg agc ttc atc cag agc atc aaa gtg atc aac gcc atc    1392
Val Val Lys Arg Ser Phe Ile Gln Ser Ile Lys Val Ile Asn Ala Ile
        450                 455                 460 atc aag aag tac ggc ctg ccc aat gat atc att atc gag ctg gct agg    1440
Ile Lys Lys Tyr Gly Leu Pro Asn Asp Ile Ile Ile Glu Leu Ala Arg
465                 470                 475                 480 gag aag aac agc aag gac gca cag aag atg atc aat gag atg cag aaa    1488
Glu Lys Asn Ser Lys Asp Ala Gln Lys Met Ile Asn Glu Met Gln Lys
                485                 490                 495
```

-continued

| | | |
|---|---|---|
| cga aac cgg cag acc aat gaa cgc att gaa gag att atc cga act acc<br>Arg Asn Arg Gln Thr Asn Glu Arg Ile Glu Glu Ile Ile Arg Thr Thr<br>500 505 510 | 1536 | |
| ggg aaa gag aac gca aag tac ctg att gaa aaa atc aag ctg cac gat<br>Gly Lys Glu Asn Ala Lys Tyr Leu Ile Glu Lys Ile Lys Leu His Asp<br>515 520 525 | 1584 | |
| atg cag gag gga aag tgt ctg tat tct ctg gag gcc atc ccc ctg gag<br>Met Gln Glu Gly Lys Cys Leu Tyr Ser Leu Glu Ala Ile Pro Leu Glu<br>530 535 540 | 1632 | |
| gac ctg ctg aac aat cca ttc aac tac gag gtc gat cat att atc ccc<br>Asp Leu Leu Asn Asn Pro Phe Asn Tyr Glu Val Asp His Ile Ile Pro<br>545 550 555 560 | 1680 | |
| aga agc gtg tcc ttc gac aat tcc ttt aac aac aag gtg ctg gtc aag<br>Arg Ser Val Ser Phe Asp Asn Ser Phe Asn Asn Lys Val Leu Val Lys<br>565 570 575 | 1728 | |
| cag gaa gag aac tct aaa aag ggc aat agg act cct ttc cag tac ctg<br>Gln Glu Glu Asn Ser Lys Lys Gly Asn Arg Thr Pro Phe Gln Tyr Leu<br>580 585 590 | 1776 | |
| tct agt tca gat tcc aag atc tct tac gaa acc ttt aaa aag cac att<br>Ser Ser Ser Asp Ser Lys Ile Ser Tyr Glu Thr Phe Lys Lys His Ile<br>595 600 605 | 1824 | |
| ctg aat ctg gcc aaa gga aag ggc cgc atc agc aag acc aaa aag gag<br>Leu Asn Leu Ala Lys Gly Lys Gly Arg Ile Ser Lys Thr Lys Lys Glu<br>610 615 620 | 1872 | |
| tac ctg ctg gaa gag cgg gac atc aac aga ttc tcc gtc cag aag gat<br>Tyr Leu Leu Glu Glu Arg Asp Ile Asn Arg Phe Ser Val Gln Lys Asp<br>625 630 635 640 | 1920 | |
| ttt att aac cgg aat ctg gtg gac aca aga tac gct act cgc ggc ctg<br>Phe Ile Asn Arg Asn Leu Val Asp Thr Arg Tyr Ala Thr Arg Gly Leu<br>645 650 655 | 1968 | |
| atg aat ctg ctg cga tcc tat ttc cgg gtg aac aat ctg gat gtg aaa<br>Met Asn Leu Leu Arg Ser Tyr Phe Arg Val Asn Asn Leu Asp Val Lys<br>660 665 670 | 2016 | |
| gtc aag tcc atc aac ggc ggg ttc aca tct ttt ctg agg cgc aaa tgg<br>Val Lys Ser Ile Asn Gly Gly Phe Thr Ser Phe Leu Arg Arg Lys Trp<br>675 680 685 | 2064 | |
| aag ttt aaa aag gag cgc aac aaa ggg tac aag cac cat gcc gaa gat<br>Lys Phe Lys Lys Glu Arg Asn Lys Gly Tyr Lys His His Ala Glu Asp<br>690 695 700 | 2112 | |
| gct ctg att atc gca aat gcc gac ttc atc ttt aag gag tgg aaa aag<br>Ala Leu Ile Ile Ala Asn Ala Asp Phe Ile Phe Lys Glu Trp Lys Lys<br>705 710 715 720 | 2160 | |
| ctg gac aaa gcc aag aaa gtg atg gag aac cag atg ttc gaa gag aag<br>Leu Asp Lys Ala Lys Lys Val Met Glu Asn Gln Met Phe Glu Glu Lys<br>725 730 735 | 2208 | |
| cag gcc gaa tct atg ccc gaa atc gag aca gaa cag gag tac aag gag<br>Gln Ala Glu Ser Met Pro Glu Ile Glu Thr Glu Gln Glu Tyr Lys Glu<br>740 745 750 | 2256 | |
| att ttc atc act cct cac cag atc aag cat atc aag gat ttc aag gac<br>Ile Phe Ile Thr Pro His Gln Ile Lys His Ile Lys Asp Phe Lys Asp<br>755 760 765 | 2304 | |
| tac aag tac tct cac cgg gtg gat aaa aag ccc aac aga gag ctg atc<br>Tyr Lys Tyr Ser His Arg Val Asp Lys Lys Pro Asn Arg Glu Leu Ile<br>770 775 780 | 2352 | |
| aat gac acc ctg tat agt aca aga aaa gac gat aag ggg aat acc ctg<br>Asn Asp Thr Leu Tyr Ser Thr Arg Lys Asp Asp Lys Gly Asn Thr Leu<br>785 790 795 800 | 2400 | |
| att gtg aac aat ctg aac gga ctg tac gac aaa gat aat gac aag ctg<br>Ile Val Asn Asn Leu Asn Gly Leu Tyr Asp Lys Asp Asn Asp Lys Leu<br>805 810 815 | 2448 | |

-continued

```
aaa aag ctg atc aac aaa agt ccc gag aag ctg ctg atg tac cac cat    2496
Lys Lys Leu Ile Asn Lys Ser Pro Glu Lys Leu Leu Met Tyr His His
            820                 825                 830 gat cct cag aca tat cag aaa ctg aag ctg att atg gag cag tac ggc    2544
Asp Pro Gln Thr Tyr Gln Lys Leu Lys Leu Ile Met Glu Gln Tyr Gly
        835                 840                 845 gac gag aag aac cca ctg tat aag tac tat gaa gag act ggg aac tac    2592
Asp Glu Lys Asn Pro Leu Tyr Lys Tyr Tyr Glu Glu Thr Gly Asn Tyr
    850                 855                 860 ctg acc aag tat agc aaa aag gat aat ggc ccc gtc atc aag aag atc    2640
Leu Thr Lys Tyr Ser Lys Lys Asp Asn Gly Pro Val Ile Lys Lys Ile
865                 870                 875                 880 aag tac tat ggg aac aag ctg aat gcc cat ctg gac atc aca gac gat    2688
Lys Tyr Tyr Gly Asn Lys Leu Asn Ala His Leu Asp Ile Thr Asp Asp
                885                 890                 895 tac cct aac agt cgc aac aag gtg gtc aag ctg tca ctg aag cca tac    2736
Tyr Pro Asn Ser Arg Asn Lys Val Val Lys Leu Ser Leu Lys Pro Tyr
            900                 905                 910 aga ttc gat gtc tat ctg gac aac ggc gtg tat aaa ttt gtg act gtc    2784
Arg Phe Asp Val Tyr Leu Asp Asn Gly Val Tyr Lys Phe Val Thr Val
        915                 920                 925 aag aat ctg gat gtc atc aaa aag gag aac tac tat gaa gtg aat agc    2832
Lys Asn Leu Asp Val Ile Lys Lys Glu Asn Tyr Tyr Glu Val Asn Ser
    930                 935                 940 aag tgc tac gaa gag gct aaa aag ctg aaa aag att agc aac cag gca    2880
Lys Cys Tyr Glu Glu Ala Lys Lys Leu Lys Lys Ile Ser Asn Gln Ala
945                 950                 955                 960 gag ttc atc gcc tcc ttt tac aac aac gac ctg att aag atc aat ggc    2928
Glu Phe Ile Ala Ser Phe Tyr Asn Asn Asp Leu Ile Lys Ile Asn Gly
                965                 970                 975 gaa ctg tat agg gtc atc ggg gtg aac aat gat ctg ctg aac cgc att    2976
Glu Leu Tyr Arg Val Ile Gly Val Asn Asn Asp Leu Leu Asn Arg Ile
            980                 985                 990 gaa gtg aat atg att gac atc act tac cga gag tat ctg gaa aac atg    3024
Glu Val Asn Met Ile Asp Ile Thr Tyr Arg Glu Tyr Leu Glu Asn Met
        995                 1000                1005 aat gat aag cgc ccc cct cga att atc aaa aca att gcc tct aag       3069
Asn Asp Lys Arg Pro Pro Arg Ile Ile Lys Thr Ile Ala Ser Lys
    1010                1015                1020 act cag agt atc aaa aag tac tca acc gac att ctg gga aac ctg       3114
Thr Gln Ser Ile Lys Lys Tyr Ser Thr Asp Ile Leu Gly Asn Leu
    1025                1030                1035 tat gag gtg aag agc aaa aag cac cct cag att atc aaa aag ggc       3159
Tyr Glu Val Lys Ser Lys Lys His Pro Gln Ile Ile Lys Lys Gly
    1040                1045                1050 taa                                                                3162
```

<210> SEQ ID NO 2
<211> LENGTH: 1053
<212> TYPE: PRT
<213> ORGANISM: Staphylococcus aureus

<400> SEQUENCE: 2

```
Met Lys Arg Asn Tyr Ile Leu Gly Leu Asp Ile Gly Ile Thr Ser Val
1               5                   10                  15

Gly Tyr Gly Ile Ile Asp Tyr Glu Thr Arg Asp Val Ile Asp Ala Gly
            20                  25                  30

Val Arg Leu Phe Lys Glu Ala Asn Val Glu Asn Asn Glu Gly Arg Arg
        35                  40                  45
```

```
Ser Lys Arg Gly Ala Arg Arg Leu Lys Arg Arg Arg His Arg Ile
    50                  55                  60

Gln Arg Val Lys Lys Leu Leu Phe Asp Tyr Asn Leu Leu Thr Asp His
 65                  70                  75                  80

Ser Glu Leu Ser Gly Ile Asn Pro Tyr Glu Ala Arg Val Lys Gly Leu
                 85                  90                  95

Ser Gln Lys Leu Ser Glu Glu Phe Ser Ala Ala Leu Leu His Leu
            100                 105                 110

Ala Lys Arg Arg Gly Val His Asn Val Asn Glu Val Glu Glu Asp Thr
        115                 120                 125

Gly Asn Glu Leu Ser Thr Lys Glu Gln Ile Ser Arg Asn Ser Lys Ala
    130                 135                 140

Leu Glu Glu Lys Tyr Val Ala Glu Leu Gln Leu Glu Arg Leu Lys Lys
145                 150                 155                 160

Asp Gly Glu Val Arg Gly Ser Ile Asn Arg Phe Lys Thr Ser Asp Tyr
                    165                 170                 175

Val Lys Glu Ala Lys Gln Leu Leu Lys Val Gln Lys Ala Tyr His Gln
                180                 185                 190

Leu Asp Gln Ser Phe Ile Asp Thr Tyr Ile Asp Leu Leu Glu Thr Arg
            195                 200                 205

Arg Thr Tyr Tyr Glu Gly Pro Gly Glu Gly Ser Pro Phe Gly Trp Lys
    210                 215                 220

Asp Ile Lys Glu Trp Tyr Glu Met Leu Met Gly His Cys Thr Tyr Phe
225                 230                 235                 240

Pro Glu Glu Leu Arg Ser Val Lys Tyr Ala Tyr Asn Ala Asp Leu Tyr
                    245                 250                 255

Asn Ala Leu Asn Asp Leu Asn Asn Leu Val Ile Thr Arg Asp Glu Asn
                260                 265                 270

Glu Lys Leu Glu Tyr Tyr Glu Lys Phe Gln Ile Ile Glu Asn Val Phe
            275                 280                 285

Lys Gln Lys Lys Lys Pro Thr Leu Lys Gln Ile Ala Lys Glu Ile Leu
    290                 295                 300

Val Asn Glu Glu Asp Ile Lys Gly Tyr Arg Val Thr Ser Thr Gly Lys
305                 310                 315                 320

Pro Glu Phe Thr Asn Leu Lys Val Tyr His Asp Ile Lys Asp Ile Thr
                    325                 330                 335

Ala Arg Lys Glu Ile Ile Glu Asn Ala Glu Leu Leu Asp Gln Ile Ala
                340                 345                 350

Lys Ile Leu Thr Ile Tyr Gln Ser Ser Glu Asp Ile Gln Glu Glu Leu
            355                 360                 365

Thr Asn Leu Asn Ser Glu Leu Thr Gln Glu Glu Ile Glu Gln Ile Ser
    370                 375                 380

Asn Leu Lys Gly Tyr Thr Gly Thr His Asn Leu Ser Leu Lys Ala Ile
385                 390                 395                 400

Asn Leu Ile Leu Asp Glu Leu Trp His Thr Asn Asp Asn Gln Ile Ala
                    405                 410                 415

Ile Phe Asn Arg Leu Lys Leu Val Pro Lys Lys Val Asp Leu Ser Gln
                420                 425                 430

Gln Lys Glu Ile Pro Thr Thr Leu Val Asp Asp Phe Ile Leu Ser Pro
            435                 440                 445

Val Val Lys Arg Ser Phe Ile Gln Ser Ile Lys Val Ile Asn Ala Ile
    450                 455                 460
```

-continued

```
Ile Lys Lys Tyr Gly Leu Pro Asn Asp Ile Ile Glu Leu Ala Arg
465                 470                 475                 480

Glu Lys Asn Ser Lys Asp Ala Gln Lys Met Ile Asn Glu Met Gln Lys
            485                 490                 495

Arg Asn Arg Gln Thr Asn Glu Arg Ile Glu Glu Ile Arg Thr Thr
            500                 505                 510

Gly Lys Glu Asn Ala Lys Tyr Leu Ile Glu Lys Ile Lys Leu His Asp
            515                 520                 525

Met Gln Glu Gly Lys Cys Leu Tyr Ser Leu Glu Ala Ile Pro Leu Glu
            530                 535                 540

Asp Leu Leu Asn Asn Pro Phe Asn Tyr Glu Val Asp His Ile Ile Pro
545                 550                 555                 560

Arg Ser Val Ser Phe Asp Asn Ser Phe Asn Asn Lys Val Leu Val Lys
                565                 570                 575

Gln Glu Glu Asn Ser Lys Lys Gly Asn Arg Thr Pro Phe Gln Tyr Leu
            580                 585                 590

Ser Ser Ser Asp Ser Lys Ile Ser Tyr Glu Thr Phe Lys Lys His Ile
            595                 600                 605

Leu Asn Leu Ala Lys Gly Lys Gly Arg Ile Ser Lys Thr Lys Lys Glu
610                 615                 620

Tyr Leu Leu Glu Glu Arg Asp Ile Asn Arg Phe Ser Val Gln Lys Asp
625                 630                 635                 640

Phe Ile Asn Arg Asn Leu Val Asp Thr Arg Tyr Ala Thr Arg Gly Leu
                645                 650                 655

Met Asn Leu Leu Arg Ser Tyr Phe Arg Val Asn Asn Leu Asp Val Lys
            660                 665                 670

Val Lys Ser Ile Asn Gly Gly Phe Thr Ser Phe Leu Arg Arg Lys Trp
            675                 680                 685

Lys Phe Lys Lys Glu Arg Asn Lys Gly Tyr Lys His His Ala Glu Asp
            690                 695                 700

Ala Leu Ile Ile Ala Asn Ala Asp Phe Ile Phe Lys Glu Trp Lys Lys
705                 710                 715                 720

Leu Asp Lys Ala Lys Lys Val Met Glu Asn Gln Met Phe Glu Glu Lys
            725                 730                 735

Gln Ala Glu Ser Met Pro Glu Ile Glu Thr Glu Gln Glu Tyr Lys Glu
            740                 745                 750

Ile Phe Ile Thr Pro His Gln Ile Lys His Ile Lys Asp Phe Lys Asp
            755                 760                 765

Tyr Lys Tyr Ser His Arg Val Asp Lys Lys Pro Asn Arg Glu Leu Ile
770                 775                 780

Asn Asp Thr Leu Tyr Ser Thr Arg Lys Asp Asp Lys Gly Asn Thr Leu
785                 790                 795                 800

Ile Val Asn Asn Leu Asn Gly Leu Tyr Asp Lys Asp Asn Asp Lys Leu
                805                 810                 815

Lys Lys Leu Ile Asn Lys Ser Pro Glu Lys Leu Leu Met Tyr His His
            820                 825                 830

Asp Pro Gln Thr Tyr Gln Lys Leu Lys Leu Ile Met Glu Gln Tyr Gly
            835                 840                 845

Asp Glu Lys Asn Pro Leu Tyr Lys Tyr Tyr Glu Glu Thr Gly Asn Tyr
            850                 855                 860

Leu Thr Lys Tyr Ser Lys Lys Asp Asn Gly Pro Val Ile Lys Lys Ile
865                 870                 875                 880

Lys Tyr Tyr Gly Asn Lys Leu Asn Ala His Leu Asp Ile Thr Asp Asp
```

```
                     885              890              895
Tyr Pro Asn Ser Arg Asn Lys Val Val Lys Leu Ser Leu Lys Pro Tyr
                900              905              910

Arg Phe Asp Val Tyr Leu Asp Asn Gly Val Tyr Lys Phe Val Thr Val
                915              920              925

Lys Asn Leu Asp Val Ile Lys Lys Glu Asn Tyr Tyr Glu Val Asn Ser
                930              935              940

Lys Cys Tyr Glu Glu Ala Lys Lys Leu Lys Lys Ile Ser Asn Gln Ala
945              950              955              960

Glu Phe Ile Ala Ser Phe Tyr Asn Asn Asp Leu Ile Lys Ile Asn Gly
                965              970              975

Glu Leu Tyr Arg Val Ile Gly Val Asn Asn Asp Leu Leu Asn Arg Ile
                980              985              990

Glu Val Asn Met Ile Asp Ile Thr  Tyr Arg Glu Tyr Leu  Glu Asn Met
                995              1000             1005

Asn Asp  Lys Arg Pro Pro Arg  Ile Ile Lys Thr  Ile  Ala Ser Lys
         1010             1015              1020

Thr Gln  Ser Ile Lys Lys Tyr  Ser Thr Asp Ile  Leu  Gly Asn Leu
         1025             1030              1035

Tyr Glu  Val Lys Ser Lys Lys  His Pro Gln Ile  Ile  Lys Lys Gly
         1040             1045              1050

<210> SEQ ID NO 3
<211> LENGTH: 97
<212> TYPE: DNA
<213> ORGANISM: Artificial Sequence
<220> FEATURE:
<223> OTHER INFORMATION: guide sequence

<400> SEQUENCE: 3
ggaaattagg tgcgctgggg gttttagtac tctggaaaca gaatctacta aaacaaggca      60
aaatgccgtg tttatctcgt caacttgttg gcgagat                                97

<210> SEQ ID NO 4
<211> LENGTH: 3191
<212> TYPE: DNA
<213> ORGANISM: Artificial Sequence
<220> FEATURE:
<223> OTHER INFORMATION: targent sequence

<400> SEQUENCE: 4
agcgcccaat acgcaaaccg cctctccccg cgcgttggcc gattcattaa tgcagctggc      60
acgacaggtt tcccgactgg aaagcgggca gtgagcgcaa cgcaattaat gtgagttagc     120
tcactcatta ggcaccccag gctttacact ttatgcttcc ggctcgtatg ttgtgtggaa     180
ttgtgagcgg ataacaattt cacacaggaa acagctatga ccatgattac gccaagcttg     240
catgcctgca ggtcgactct agaggatccc cgggtaccga gctcgaattc actggccgtc     300
gttttacaac gtcgtgactg ggaaaaccct ggcgttaccc aacttaatcg ccttgcagca     360
catccccctt tcgccagctg gcgtaatagc gaagaggccc gcaccgatcg cccttcccaa     420
cagttgcgca gcctgaatgg cgaatggcgc ctgatgcggt attttctcct tacgcatctg     480
tgcggtattt cacaccgcat acgtcaaagc aaccatagta cgcgccctgt agcggcgcat     540
taagcgcggc gggtgtggtg gttacgcgca gcgtgaccgc tacacttgcc agcgccctag     600
cgcccgctcc tttcgctttc ttcccttcct ttctcgccac gttcgccggc tttccccgtc     660
aagctctaaa tcggggggctc cctttagggt tccgatttag tgctttacgg cacctcgacc     720
```

```
ccaaaaaact tgatttgggt gatggttcac gtagtgggcc atcgccctga tagacggttt    780
ttcgcccttt gacgttggag tccacgttct ttaatagtgg actcttgttc caaactggaa    840
caacactcaa ccctatctcg ggctattctt ttgatttata agggattttg ccgatttcgg    900
cctattggtt aaaaaatgag ctgatttaac aaaaatttaa cgcgaatttt aacaaaatat    960
taacgtttac aattttatgg tgcactctca gtacaatctg ctctgatgcc gcatagttaa   1020
gccagccccg acaccgcca acacccgctg acgcgcctg acgggcttgt ctgctcccgg   1080
catccgctta cagacaagct gtgaccgtct ccgggagctg catgtgtcag aggttttcac   1140
cgtcatcacc gaaacgcgcg agacgaaagg gcctcgtgat acgcctattt ttataggtta   1200
atgtcatgat aataatggtt tcttagacgt caggtggcac ttttcgggga atgtgcgcg   1260 gaacccctat ttgtttattt ttctaaatac ggaaattagg tgcgcttggc ttgaattgga   1320
ttcaaatatg tatccgctca tgagacaata accctgataa atgcttcaat aatattgaaa   1380
aaggaagagt atgagtattc aacatttccg tgtcgccctt attcccttt ttgcggcatt   1440 ttgccttcct gttttgctc acccagaaac gctggtgaaa gtaaagatg ctgaagatca   1500 gttgggtgca cgagtgggtt acatcgaact ggatctcaac agcggtaaga tccttgagag   1560
ttttcgcccc gaagaacgtt ttccaatgat gagcactttt aaagttctgc tatgtggcgc   1620
ggtattatcc cgtattgacg ccgggcaaga gcaactcggt cgccgcatac actattctca   1680
gaatgacttg gttgagtact caccagtcac agaaaagcat cttacggatg gcatgacagt   1740
aagagaatta tgcagtgctg ccataaccat gagtgataac actgcggcca acttacttct   1800
gacaacgatc ggaggaccga aggagctaac cgcttttttg cacaacatgg gggatcatgt   1860
aactcgcctt gatcgttggg aaccggagct gaatgaagcc ataccaaacg acgagcgtga   1920
caccacgatg cctgtagcaa tggcaacaac gttgcgcaaa ctattaactg gcgaactact   1980
tactctagct tcccggcaac aattaataga ctggatggag gcggataaag ttgcaggacc   2040
acttctgcgc tcggcccttc cggctggctg gtttattgct gataaatctg gagccggtga   2100
gcgtgggtct cgcggtatca ttgcagcact ggggccagat ggtaagccct cccgtatcgt   2160
agttatctac acgacgggga gtcaggcaac tatggatgaa cgaaatagac agatcgctga   2220
gataggtgcc tcactgatta gcattggta actgtcagac caagtttact catatatact   2280
ttagattgat ttaaaacttc atttttaatt taaaaggatc taggtgaaga tccttttga   2340 taatctcatg accaaaatcc cttaacgtga gttttcgttc cactgagcgt cagacccgt   2400 agaaaagatc aaaggatctt cttgagatcc tttttttctg cgcgtaatct gctgcttgca   2460
aacaaaaaaa ccaccgctac cagcggtggt ttgtttgccg gatcaagagc taccaactct   2520
ttttccgaag gtaactggct tcagcagagc gcagatacca aatactgtcc ttctagtgta   2580
gccgtagtta ggccaccact tcaagaactc tgtagcaccg cctacatacc tcgctctgct   2640
aatcctgtta ccagtggctg ctgccagtgg cgataagtcg tgtcttaccg ggttggactc   2700
aagacgatag ttaccggata aggcgcagcg gtcgggctga acggggggtt cgtgcacaca   2760
gcccagcttg gagcgaacga cctacaccga actgagatac ctacagcgtg agctatgaga   2820
aagcgccacg cttcccgaag ggagaaaggc ggacaggtat ccggtaagcg gcagggtcgg   2880
aacaggagag cgcacgaggg agcttccagg gggaaacgcc tggtatcttt atagtcctgt   2940
cgggtttcgc cacctctgac ttgagcgtcg atttttgtga tgctcgtcag ggggcggag   3000 cctatggaaa aacgccagca acgcggcctt tttacggttc ctggccttt gctggccttt   3060
```

```
tgctcacatg ttctttcctg cgttatcccc tgattctgtg gataaccgta ttaccgcctt   3120
tgagtgagct gataccgctc gccgcagccg aacgaccgag cgcagcgagt cagtgagcga   3180
ggaagcggaa g                                                         3191

<210> SEQ ID NO 5
<211> LENGTH: 21
<212> TYPE: DNA
<213> ORGANISM: Artificial Sequence
<220> FEATURE:
<223> OTHER INFORMATION: spacer sequence

<400> SEQUENCE: 5
aaaaataacc ttagtctatc a                                              21

<210> SEQ ID NO 6
<211> LENGTH: 21
<212> TYPE: DNA
<213> ORGANISM: Artificial Sequence
<220> FEATURE:
<223> OTHER INFORMATION: spacer sequence

<400> SEQUENCE: 6
ttgtatcctg taatgctctc a                                              21

<210> SEQ ID NO 7
<211> LENGTH: 21
<212> TYPE: DNA
<213> ORGANISM: Artificial Sequence
<220> FEATURE:
<223> OTHER INFORMATION: spacer sequence

<400> SEQUENCE: 7
acctggttca tcatcactaa t                                              21

<210> SEQ ID NO 8
<211> LENGTH: 21
<212> TYPE: DNA
<213> ORGANISM: Artificial Sequence
<220> FEATURE:
<223> OTHER INFORMATION: spacer sequence

<400> SEQUENCE: 8
ctaatcatta tgctgaggat t                                              21

<210> SEQ ID NO 9
<211> LENGTH: 21
<212> TYPE: DNA
<213> ORGANISM: Artificial Sequence
<220> FEATURE:
<223> OTHER INFORMATION: spacer sequence

<400> SEQUENCE: 9
gctgatgttt gaaattaaca c                                              21

<210> SEQ ID NO 10
<211> LENGTH: 21
<212> TYPE: DNA
<213> ORGANISM: Artificial Sequence
<220> FEATURE:
<223> OTHER INFORMATION: spacer sequence

<400> SEQUENCE: 10
ttaacatctt aatccaatca a                                              21
```

```
<210> SEQ ID NO 11
<211> LENGTH: 21
<212> TYPE: DNA
<213> ORGANISM: Artificial Sequence
<220> FEATURE:
<223> OTHER INFORMATION: spacer sequence

<400> SEQUENCE: 11
taatctgaaa aagaaatata g                                              21

<210> SEQ ID NO 12
<211> LENGTH: 21
<212> TYPE: DNA
<213> ORGANISM: Artificial Sequence
<220> FEATURE:
<223> OTHER INFORMATION: spacer sequence

<400> SEQUENCE: 12
tatgctgagg atttggaaag g                                              21

<210> SEQ ID NO 13
<211> LENGTH: 21
<212> TYPE: DNA
<213> ORGANISM: Artificial Sequence
<220> FEATURE:
<223> OTHER INFORMATION: spacer sequence

<400> SEQUENCE: 13
ggtaagtaag atcttaaaat g                                              21

<210> SEQ ID NO 14
<211> LENGTH: 21
<212> TYPE: DNA
<213> ORGANISM: Artificial Sequence
<220> FEATURE:
<223> OTHER INFORMATION: spacer sequence

<400> SEQUENCE: 14
aagtactcag aacagctgct g                                              21

<210> SEQ ID NO 15
<211> LENGTH: 21
<212> TYPE: DNA
<213> ORGANISM: Artificial Sequence
<220> FEATURE:
<223> OTHER INFORMATION: spacer sequence

<400> SEQUENCE: 15
tgcataccta atcattatgc t                                              21

<210> SEQ ID NO 16
<211> LENGTH: 21
<212> TYPE: DNA
<213> ORGANISM: Artificial Sequence
<220> FEATURE:
<223> OTHER INFORMATION: spacer sequence

<400> SEQUENCE: 16
tcattatgct gaggatttgg a                                              21

<210> SEQ ID NO 17
<211> LENGTH: 21
<212> TYPE: DNA
<213> ORGANISM: Artificial Sequence
<220> FEATURE:
<223> OTHER INFORMATION: spacer sequence
```

<400> SEQUENCE: 17
cctgtccata attagtccat g                                      21

<210> SEQ ID NO 18
<211> LENGTH: 21
<212> TYPE: DNA
<213> ORGANISM: Artificial Sequence
<220> FEATURE:
<223> OTHER INFORMATION: spacer sequence

<400> SEQUENCE: 18
tgcttgtccc tctgtcaatg g                                      21

<210> SEQ ID NO 19
<211> LENGTH: 21
<212> TYPE: DNA
<213> ORGANISM: Artificial Sequence
<220> FEATURE:
<223> OTHER INFORMATION: spacer sequence

<400> SEQUENCE: 19
ggagtggcca gagtccagct t                                      21

<210> SEQ ID NO 20
<211> LENGTH: 21
<212> TYPE: DNA
<213> ORGANISM: Artificial Sequence
<220> FEATURE:
<223> OTHER INFORMATION: spacer sequence

<400> SEQUENCE: 20
ggcttctcag gaatgacacc c                                      21

<210> SEQ ID NO 21
<211> LENGTH: 21
<212> TYPE: DNA
<213> ORGANISM: Artificial Sequence
<220> FEATURE:
<223> OTHER INFORMATION: spacer sequence

<400> SEQUENCE: 21
ggccggggtg tcattcctga g                                      21

<210> SEQ ID NO 22
<211> LENGTH: 21
<212> TYPE: DNA
<213> ORGANISM: Artificial Sequence
<220> FEATURE:
<223> OTHER INFORMATION: spacer sequence

<400> SEQUENCE: 22
gagaaccacc cagggtccag g                                      21

<210> SEQ ID NO 23
<211> LENGTH: 21
<212> TYPE: DNA
<213> ORGANISM: Artificial Sequence
<220> FEATURE:
<223> OTHER INFORMATION: spacer sequence

<400> SEQUENCE: 23
gactcagggc cagatgcagg g                                      21

<210> SEQ ID NO 24
<211> LENGTH: 21

```
<212> TYPE: DNA
<213> ORGANISM: Artificial Sequence
<220> FEATURE:
<223> OTHER INFORMATION: spacer sequence

<400> SEQUENCE: 24
agagtccagc ttgggcccac g                                              21

<210> SEQ ID NO 25
<211> LENGTH: 21
<212> TYPE: DNA
<213> ORGANISM: Artificial Sequence
<220> FEATURE:
<223> OTHER INFORMATION: spacer sequence

<400> SEQUENCE: 25
tggccactcc ctggccaggc t                                              21

<210> SEQ ID NO 26
<211> LENGTH: 21
<212> TYPE: DNA
<213> ORGANISM: Artificial Sequence
<220> FEATURE:
<223> OTHER INFORMATION: spacer sequence

<400> SEQUENCE: 26
tggccccaca gggcttgaag c                                              21

<210> SEQ ID NO 27
<211> LENGTH: 21
<212> TYPE: DNA
<213> ORGANISM: Artificial Sequence
<220> FEATURE:
<223> OTHER INFORMATION: spacer sequence

<400> SEQUENCE: 27
acagtcatag caggctccag g                                              21

<210> SEQ ID NO 28
<211> LENGTH: 21
<212> TYPE: DNA
<213> ORGANISM: Artificial Sequence
<220> FEATURE:
<223> OTHER INFORMATION: spacer sequence

<400> SEQUENCE: 28
ggcctcccca aagcctggcc a                                              21

<210> SEQ ID NO 29
<211> LENGTH: 21
<212> TYPE: DNA
<213> ORGANISM: Artificial Sequence
<220> FEATURE:
<223> OTHER INFORMATION: spacer sequence

<400> SEQUENCE: 29
tggccaggct ttggggaggc c                                              21

<210> SEQ ID NO 30
<211> LENGTH: 21
<212> TYPE: DNA
<213> ORGANISM: Artificial Sequence
<220> FEATURE:
<223> OTHER INFORMATION: spacer sequence

<400> SEQUENCE: 30
```

```
gccagcccac ttgggcttct c                                              21

<210> SEQ ID NO 31
<211> LENGTH: 20
<212> TYPE: DNA
<213> ORGANISM: Artificial Sequence
<220> FEATURE:
<223> OTHER INFORMATION: HPRT PCR primer (Forward)

<400> SEQUENCE: 31
tacacgtgtg aaccaacccg                                                20

<210> SEQ ID NO 32
<211> LENGTH: 22
<212> TYPE: DNA
<213> ORGANISM: Artificial Sequence
<220> FEATURE:
<223> OTHER INFORMATION: HPRT PCR primer (Reverse)

<400> SEQUENCE: 32
gtaaggccct cctcttttat tt                                             22

<210> SEQ ID NO 33
<211> LENGTH: 22
<212> TYPE: DNA
<213> ORGANISM: Artificial Sequence
<220> FEATURE:
<223> OTHER INFORMATION: EMX1 region A PCR primer (Forward)

<400> SEQUENCE: 33
agtttctcat ctgtgcccct cc                                             22

<210> SEQ ID NO 34
<211> LENGTH: 22
<212> TYPE: DNA
<213> ORGANISM: Artificial Sequence
<220> FEATURE:
<223> OTHER INFORMATION: EMX1 region A PCR primer (Reverse)

<400> SEQUENCE: 34
ctgaacgcgt ttgctctacc ag                                             22

<210> SEQ ID NO 35
<211> LENGTH: 20
<212> TYPE: DNA
<213> ORGANISM: Artificial Sequence
<220> FEATURE:
<223> OTHER INFORMATION: EMX1 region B PCR primer (Forward)

<400> SEQUENCE: 35
tttcacttgg gtgccctagg                                                20

<210> SEQ ID NO 36
<211> LENGTH: 19
<212> TYPE: DNA
<213> ORGANISM: Artificial Sequence
<220> FEATURE:
<223> OTHER INFORMATION: EMX1 region B PCR primer (Reverse)

<400> SEQUENCE: 36
ccctcttgcc agaacttcc                                                 19

<210> SEQ ID NO 37
<211> LENGTH: 4140
<212> TYPE: DNA
<213> ORGANISM: Artificial Sequence
```

<220> FEATURE:
<223> OTHER INFORMATION: NLS-WT-dSaCas9(D10A,N580A)-NLS-KRAB-P2A-Puro
fusion protein
<220> FEATURE:
<221> NAME/KEY: CDS
<222> LOCATION: (1)..(4140)

<400> SEQUENCE: 37

```
atg gcc cca aag aag aag cgg aag gtc ggt atc cac gga gtc cca gca      48
Met Ala Pro Lys Lys Lys Arg Lys Val Gly Ile His Gly Val Pro Ala
1               5                   10                  15 gcc aag cgg aac tac atc ctg ggc ctg gcc atc ggc atc acc agc gtg      96
Ala Lys Arg Asn Tyr Ile Leu Gly Leu Ala Ile Gly Ile Thr Ser Val
            20                  25                  30 ggc tac ggc atc atc gac tac gag aca cgg gac gtg atc gat gcc ggc     144
Gly Tyr Gly Ile Ile Asp Tyr Glu Thr Arg Asp Val Ile Asp Ala Gly
        35                  40                  45 gtg cgg ctg ttc aaa gag gcc aac gtg gaa aac aac gag ggc agg cgg     192
Val Arg Leu Phe Lys Glu Ala Asn Val Glu Asn Asn Glu Gly Arg Arg
    50                  55                  60 agc aag aga ggc gcc aga agg ctg aag cgg agg agg cat aga atc         240
Ser Lys Arg Gly Ala Arg Arg Leu Lys Arg Arg Arg His Arg Ile
65                  70                  75                  80 cag aga gtg aag aag ctg ctg ttc gac tac aac ctg ctg acc gac cac     288
Gln Arg Val Lys Lys Leu Leu Phe Asp Tyr Asn Leu Leu Thr Asp His
                85                  90                  95 agc gag ctg agc ggc atc aac ccc tac gag gcc aga gtg aag ggc ctg     336
Ser Glu Leu Ser Gly Ile Asn Pro Tyr Glu Ala Arg Val Lys Gly Leu
            100                 105                 110 agc cag aag ctg agc gag gaa gag ttc tct gcc gcc ctg ctg cac ctg     384
Ser Gln Lys Leu Ser Glu Glu Glu Phe Ser Ala Ala Leu Leu His Leu
        115                 120                 125 gcc aag aga aga ggc gtg cac aac gtg aac gag gtg gaa gag gac acc     432
Ala Lys Arg Arg Gly Val His Asn Val Asn Glu Val Glu Glu Asp Thr
    130                 135                 140 ggc aac gag ctg tcc acc aaa gag cag atc agc cgg aac agc aag gcc     480
Gly Asn Glu Leu Ser Thr Lys Glu Gln Ile Ser Arg Asn Ser Lys Ala
145                 150                 155                 160 ctg gaa gag aaa tac gtg gcc gaa ctg cag ctg gaa cgg ctg aag aaa     528
Leu Glu Glu Lys Tyr Val Ala Glu Leu Gln Leu Glu Arg Leu Lys Lys
                165                 170                 175 gac ggc gaa gtg cgg ggc agc atc aac aga ttc aag acc agc gac tac     576
Asp Gly Glu Val Arg Gly Ser Ile Asn Arg Phe Lys Thr Ser Asp Tyr
            180                 185                 190 gtg aaa gaa gcc aaa cag ctg ctg aag gtg cag aag gcc tac cac cag     624
Val Lys Glu Ala Lys Gln Leu Leu Lys Val Gln Lys Ala Tyr His Gln
        195                 200                 205 ctg gac cag agc ttc atc gac acc tac atc gac ctg ctg gaa acc cgg     672
Leu Asp Gln Ser Phe Ile Asp Thr Tyr Ile Asp Leu Leu Glu Thr Arg
    210                 215                 220 cgg acc tac tat gag gga cct ggc gag ggc agc ccc ttc ggc tgg aag     720
Arg Thr Tyr Tyr Glu Gly Pro Gly Glu Gly Ser Pro Phe Gly Trp Lys
225                 230                 235                 240 gac atc aaa gaa tgg tac gag atg ctg atg ggc cac tgc acc tac ttc     768
Asp Ile Lys Glu Trp Tyr Glu Met Leu Met Gly His Cys Thr Tyr Phe
                245                 250                 255 ccc gag gaa ctg cgg agc gtg aag tac gcc tac aac gcc gac ctg tac     816
Pro Glu Glu Leu Arg Ser Val Lys Tyr Ala Tyr Asn Ala Asp Leu Tyr
            260                 265                 270 aac gcc ctg aac gac ctg aac aat ctc gtg atc acc agg gac gag aac     864
Asn Ala Leu Asn Asp Leu Asn Asn Leu Val Ile Thr Arg Asp Glu Asn
```

-continued

|  |  |  |  |  |  |  |  |  |  |  |  |  |  |  |  |  |
|---|---|---|---|---|---|---|---|---|---|---|---|---|---|---|---|---|
|  |  | 275 |  |  |  | 280 |  |  |  | 285 |  |  |  |  |  |  |

```
gag aag ctg gaa tat tac gag aag ttc cag atc atc gag aac gtg ttc      912
Glu Lys Leu Glu Tyr Tyr Glu Lys Phe Gln Ile Ile Glu Asn Val Phe
290                 295                 300 aag cag aag aag aag ccc acc ctg aag cag atc gcc aaa gaa atc ctc      960
Lys Gln Lys Lys Lys Pro Thr Leu Lys Gln Ile Ala Lys Glu Ile Leu
305                 310                 315                 320 gtg aac gaa gag gat att aag ggc tac aga gtg acc agc acc ggc aag     1008
Val Asn Glu Glu Asp Ile Lys Gly Tyr Arg Val Thr Ser Thr Gly Lys
        325                 330                 335 ccc gag ttc acc aac ctg aag gtg tac cac gac atc aag gac att acc     1056
Pro Glu Phe Thr Asn Leu Lys Val Tyr His Asp Ile Lys Asp Ile Thr
    340                 345                 350 gcc cgg aaa gag att att gag aac gcc gag ctg ctg gat cag att gcc     1104
Ala Arg Lys Glu Ile Ile Glu Asn Ala Glu Leu Leu Asp Gln Ile Ala
355                 360                 365 aag atc ctg acc atc tac cag agc agc gag gac atc cag gaa gaa ctg     1152
Lys Ile Leu Thr Ile Tyr Gln Ser Ser Glu Asp Ile Gln Glu Glu Leu
370                 375                 380 acc aat ctg aac tcc gag ctg acc cag gaa gag atc gag cag atc tct     1200
Thr Asn Leu Asn Ser Glu Leu Thr Gln Glu Glu Ile Glu Gln Ile Ser
385                 390                 395                 400 aat ctg aag ggc tat acc ggc acc cac aac ctg agc ctg aag gcc atc     1248
Asn Leu Lys Gly Tyr Thr Gly Thr His Asn Leu Ser Leu Lys Ala Ile
        405                 410                 415 aac ctg atc ctg gac gag ctg tgg cac acc aac gac aac cag atc gct     1296
Asn Leu Ile Leu Asp Glu Leu Trp His Thr Asn Asp Asn Gln Ile Ala
    420                 425                 430 atc ttc aac cgg ctg aag ctg gtg ccc aag aag gtg gac ctg tcc cag     1344
Ile Phe Asn Arg Leu Lys Leu Val Pro Lys Lys Val Asp Leu Ser Gln
435                 440                 445 cag aaa gag atc ccc acc acc ctg gtg gac gac ttc atc ctg agc ccc     1392
Gln Lys Glu Ile Pro Thr Thr Leu Val Asp Asp Phe Ile Leu Ser Pro
450                 455                 460 gtc gtg aag aga agc ttc atc cag agc atc aaa gtg atc aac gcc atc     1440
Val Val Lys Arg Ser Phe Ile Gln Ser Ile Lys Val Ile Asn Ala Ile
465                 470                 475                 480 atc aag aag tac ggc ctg ccc aac gac atc att atc gag ctg gcc cgc     1488
Ile Lys Lys Tyr Gly Leu Pro Asn Asp Ile Ile Ile Glu Leu Ala Arg
        485                 490                 495 gag aag aac tcc aag gac gcc cag aaa atg atc aac gag atg cag aag     1536
Glu Lys Asn Ser Lys Asp Ala Gln Lys Met Ile Asn Glu Met Gln Lys
    500                 505                 510 cgg aac cgg cag acc aac gag cgg atc gag gaa atc atc cgg acc acc     1584
Arg Asn Arg Gln Thr Asn Glu Arg Ile Glu Glu Ile Ile Arg Thr Thr
515                 520                 525 ggc aaa gag aac gcc aag tac ctg atc gag aag atc aag ctg cac gac     1632
Gly Lys Glu Asn Ala Lys Tyr Leu Ile Glu Lys Ile Lys Leu His Asp
530                 535                 540 atg cag gaa ggc aag tgc ctg tac agc ctg gaa gcc atc cct ctg gaa     1680
Met Gln Glu Gly Lys Cys Leu Tyr Ser Leu Glu Ala Ile Pro Leu Glu
545                 550                 555                 560 gat ctg ctg aac aac ccc ttc aac tat gag gtg gac cac atc atc ccc     1728
Asp Leu Leu Asn Asn Pro Phe Asn Tyr Glu Val Asp His Ile Ile Pro
        565                 570                 575 aga agc gtg tcc ttc gac aac agc ttc aac aac aag gtg ctc gtg aag     1776
Arg Ser Val Ser Phe Asp Asn Ser Phe Asn Asn Lys Val Leu Val Lys
    580                 585                 590 cag gaa gaa gcc agc aag aag ggc aac cgg acc cca ttc cag tac ctg     1824
```

|     |     |     |     |     |     |     |     |     |     |     |     |      |
| --- | --- | --- | --- | --- | --- | --- | --- | --- | --- | --- | --- | ---- |
| Gln | Glu | Glu | Ala | Ser | Lys | Lys | Gly | Asn | Arg | Thr | Pro | Phe | Gln | Tyr | Leu |
|     |     |     | 595 |     |     |     | 600 |     |     |     | 605 |

| agc | agc | agc | gac | agc | aag | atc | agc | tac | gaa | acc | ttc | aag | aag | cac | atc | 1872 |
| Ser | Ser | Ser | Asp | Ser | Lys | Ile | Ser | Tyr | Glu | Thr | Phe | Lys | Lys | His | Ile |
| 610 |     |     |     |     | 615 |     |     |     |     | 620 |

| ctg | aat | ctg | gcc | aag | ggc | aag | ggc | aga | atc | agc | aag | acc | aag | aaa | gag | 1920 |
| Leu | Asn | Leu | Ala | Lys | Gly | Lys | Gly | Arg | Ile | Ser | Lys | Thr | Lys | Lys | Glu |
| 625 |     |     |     |     | 630 |     |     |     |     | 635 |     |     |     |     | 640 |

| tat | ctg | ctg | gaa | gaa | cgg | gac | atc | aac | agg | ttc | tcc | gtg | cag | aaa | gac | 1968 |
| Tyr | Leu | Leu | Glu | Glu | Arg | Asp | Ile | Asn | Arg | Phe | Ser | Val | Gln | Lys | Asp |
|     |     |     |     | 645 |     |     |     |     | 650 |     |     |     |     | 655 |

| ttc | atc | aac | cgg | aac | ctg | gtg | gat | acc | aga | tac | gcc | acc | aga | ggc | ctg | 2016 |
| Phe | Ile | Asn | Arg | Asn | Leu | Val | Asp | Thr | Arg | Tyr | Ala | Thr | Arg | Gly | Leu |
|     |     |     | 660 |     |     |     |     | 665 |     |     |     |     | 670 |

| atg | aac | ctg | ctg | cgg | agc | tac | ttc | aga | gtg | aac | aac | ctg | gac | gtg | aaa | 2064 |
| Met | Asn | Leu | Leu | Arg | Ser | Tyr | Phe | Arg | Val | Asn | Asn | Leu | Asp | Val | Lys |
|     |     | 675 |     |     |     |     | 680 |     |     |     |     | 685 |

| gtg | aag | tcc | atc | aat | ggc | ggc | ttc | acc | agc | ttt | ctg | cgg | cgg | aag | tgg | 2112 |
| Val | Lys | Ser | Ile | Asn | Gly | Gly | Phe | Thr | Ser | Phe | Leu | Arg | Arg | Lys | Trp |
|     | 690 |     |     |     |     | 695 |     |     |     |     | 700 |

| aag | ttt | aag | aaa | gag | cgg | aac | aag | ggg | tac | aag | cac | cac | gcc | gag | gac | 2160 |
| Lys | Phe | Lys | Lys | Glu | Arg | Asn | Lys | Gly | Tyr | Lys | His | His | Ala | Glu | Asp |
| 705 |     |     |     |     | 710 |     |     |     |     | 715 |     |     |     |     | 720 |

| gcc | ctg | atc | att | gcc | aac | gcc | gat | ttc | atc | ttc | aaa | gag | tgg | aag | aaa | 2208 |
| Ala | Leu | Ile | Ile | Ala | Asn | Ala | Asp | Phe | Ile | Phe | Lys | Glu | Trp | Lys | Lys |
|     |     |     |     | 725 |     |     |     |     | 730 |     |     |     |     | 735 |

| ctg | gac | aag | gcc | aaa | aaa | gtg | atg | gaa | aac | cag | atg | ttc | gag | gaa | aag | 2256 |
| Leu | Asp | Lys | Ala | Lys | Lys | Val | Met | Glu | Asn | Gln | Met | Phe | Glu | Glu | Lys |
|     |     |     | 740 |     |     |     |     | 745 |     |     |     |     | 750 |

| cag | gcc | gag | agc | atg | ccc | gag | atc | gaa | acc | gag | cag | gag | tac | aaa | gag | 2304 |
| Gln | Ala | Glu | Ser | Met | Pro | Glu | Ile | Glu | Thr | Glu | Gln | Glu | Tyr | Lys | Glu |
|     |     | 755 |     |     |     |     | 760 |     |     |     |     | 765 |

| atc | ttc | atc | acc | ccc | cac | cag | atc | aag | cac | att | aag | gac | ttc | aag | gac | 2352 |
| Ile | Phe | Ile | Thr | Pro | His | Gln | Ile | Lys | His | Ile | Lys | Asp | Phe | Lys | Asp |
| 770 |     |     |     |     | 775 |     |     |     |     | 780 |

| tac | aag | tac | agc | cac | cgg | gtg | gac | aag | aag | cct | aat | aga | gag | ctg | att | 2400 |
| Tyr | Lys | Tyr | Ser | His | Arg | Val | Asp | Lys | Lys | Pro | Asn | Arg | Glu | Leu | Ile |
| 785 |     |     |     |     | 790 |     |     |     |     | 795 |     |     |     |     | 800 |

| aac | gac | acc | ctg | tac | tcc | acc | cgg | aag | gac | gac | aag | ggc | aac | acc | ctg | 2448 |
| Asn | Asp | Thr | Leu | Tyr | Ser | Thr | Arg | Lys | Asp | Asp | Lys | Gly | Asn | Thr | Leu |
|     |     |     |     | 805 |     |     |     |     | 810 |     |     |     |     | 815 |

| atc | gtg | aac | aat | ctg | aac | ggc | ctg | tac | gac | aag | gac | aat | gac | aag | ctg | 2496 |
| Ile | Val | Asn | Asn | Leu | Asn | Gly | Leu | Tyr | Asp | Lys | Asp | Asn | Asp | Lys | Leu |
|     |     |     | 820 |     |     |     |     | 825 |     |     |     |     | 830 |

| aaa | aag | ctg | atc | aac | aag | agc | ccc | gaa | aag | ctg | ctg | atg | tac | cac | cac | 2544 |
| Lys | Lys | Leu | Ile | Asn | Lys | Ser | Pro | Glu | Lys | Leu | Leu | Met | Tyr | His | His |
|     |     | 835 |     |     |     |     | 840 |     |     |     |     | 845 |

| gac | ccc | cag | acc | tac | cag | aaa | ctg | aag | ctg | att | atg | gaa | cag | tac | ggc | 2592 |
| Asp | Pro | Gln | Thr | Tyr | Gln | Lys | Leu | Lys | Leu | Ile | Met | Glu | Gln | Tyr | Gly |
| 850 |     |     |     |     | 855 |     |     |     |     | 860 |

| gac | gag | aag | aat | ccc | ctg | tac | aag | tac | tac | gag | gaa | acc | ggg | aac | tac | 2640 |
| Asp | Glu | Lys | Asn | Pro | Leu | Tyr | Lys | Tyr | Tyr | Glu | Glu | Thr | Gly | Asn | Tyr |
| 865 |     |     |     |     | 870 |     |     |     |     | 875 |     |     |     |     | 880 |

| ctg | acc | aag | tac | tcc | aaa | aag | gac | aac | ggc | ccc | gtg | atc | aag | aag | att | 2688 |
| Leu | Thr | Lys | Tyr | Ser | Lys | Lys | Asp | Asn | Gly | Pro | Val | Ile | Lys | Lys | Ile |
|     |     |     |     | 885 |     |     |     |     | 890 |     |     |     |     | 895 |

| aag | tat | tac | ggc | aac | aaa | ctg | aac | gcc | cat | ctg | gac | atc | acc | gac | gac | 2736 |
| Lys | Tyr | Tyr | Gly | Asn | Lys | Leu | Asn | Ala | His | Leu | Asp | Ile | Thr | Asp | Asp |
|     |     |     | 900 |     |     |     |     | 905 |     |     |     |     | 910 |

```
tac ccc aac agc aga aac aag gtc gtg aag ctg tcc ctg aag ccc tac    2784
Tyr Pro Asn Ser Arg Asn Lys Val Val Lys Leu Ser Leu Lys Pro Tyr
        915                 920                 925 aga ttc gac gtg tac ctg gac aat ggc gtg tac aag ttc gtg acc gtg    2832
Arg Phe Asp Val Tyr Leu Asp Asn Gly Val Tyr Lys Phe Val Thr Val
930                 935                 940 aag aat ctg gat gtg atc aaa aaa gaa aac tac tac gaa gtg aat agc    2880
Lys Asn Leu Asp Val Ile Lys Lys Glu Asn Tyr Tyr Glu Val Asn Ser
945                 950                 955                 960 aag tgc tat gag gaa gct aag aag ctg aag aag atc agc aac cag gcc    2928
Lys Cys Tyr Glu Glu Ala Lys Lys Leu Lys Lys Ile Ser Asn Gln Ala
            965                 970                 975 gag ttt atc gcc tcc ttc tac aac aac gat ctg atc aag atc aac ggc    2976
Glu Phe Ile Ala Ser Phe Tyr Asn Asn Asp Leu Ile Lys Ile Asn Gly
        980                 985                 990 gag ctg tat aga gtg atc ggc gtg  aac aac gac ctg ctg  aac cgg atc   3024
Glu Leu Tyr Arg Val Ile Gly Val  Asn Asn Asp Leu Leu  Asn Arg Ile
        995                 1000               1005 gaa gtg  aac atg atc gac atc  acc tac cgc gag tac  ctg gaa aac      3069
Glu Val  Asn Met Ile Asp Ile  Thr Tyr Arg Glu Tyr  Leu Glu Asn
1010                1015                    1020 atg aac gac aag agg ccc ccc agg atc att aag aca  atc gcc tcc        3114
Met Asn Asp Lys Arg Pro Pro Arg Ile Ile Lys Thr  Ile Ala Ser
1025                1030                1035 aag acc cag agc att aag aag tac agc aca gac att ctg ggc aac        3159
Lys Thr Gln Ser Ile Lys Lys Tyr Ser Thr Asp Ile Leu Gly Asn
1040                1045                1050 ctg tat gaa gtg aaa tct aag aag cac cct cag atc  atc aaa aag        3204
Leu Tyr Glu Val Lys Ser Lys Lys His Pro Gln Ile  Ile Lys Lys
1055                1060                1065 ggc aaa agg ccg gcg gcc acg aaa aag gcc ggc cag gca aaa aag        3249
Gly Lys Arg Pro Ala Ala Thr Lys Lys Ala Gly Gln Ala Lys Lys
1070                1075                1080 aaa aag gga tcc atg gat gct aag tca cta act gcc tgg tcc cgg        3294
Lys Lys Gly Ser Met Asp Ala Lys Ser Leu Thr Ala Trp Ser Arg
1085                1090                1095 aca ctg gtg acc ttc aag gat gta ttt gtg gac ttc acc agg gag        3339
Thr Leu Val Thr Phe Lys Asp Val Phe Val Asp Phe Thr Arg Glu
1100                1105                1110 gag tgg aag ctg ctg gac act gct cag cag atc gtg tac aga aat        3384
Glu Trp Lys Leu Leu Asp Thr Ala Gln Gln Ile Val Tyr Arg Asn
1115                1120                1125 gtg atg ctg gag aac tat aag aac ctg gtt tcc ttg ggt tat cag        3429
Val Met Leu Glu Asn Tyr Lys Asn Leu Val Ser Leu Gly Tyr Gln
1130                1135                1140 ctt act aag cca gat gtg atc ctc cgg ttg gag aag gga gaa gag        3474
Leu Thr Lys Pro Asp Val Ile Leu Arg Leu Glu Lys Gly Glu Glu
1145                1150                1155 ccc gga agc ggt gct act aac ttc agc ctg ctg aag cag gct gga        3519
Pro Gly Ser Gly Ala Thr Asn Phe Ser Leu Leu Lys Gln Ala Gly
1160                1165                1170 gac gtg gag gag aac cct gga cct acc gag tac aag ccc acg gtg        3564
Asp Val Glu Glu Asn Pro Gly Pro Thr Glu Tyr Lys Pro Thr Val
1175                1180                1185 cgc ctc gcc acc cgc gac gac gtc ccc agg gcc gta cgc acc ctc        3609
Arg Leu Ala Thr Arg Asp Asp Val Pro Arg Ala Val Arg Thr Leu
1190                1195                1200 gcc gcc gcg ttc gcc gac tac ccc gcc acg cgc cac acc gtc gat        3654
Ala Ala Ala Phe Ala Asp Tyr Pro Ala Thr Arg His Thr Val Asp
1205                1210                1215
```

| | | | | | | | | | | |
|---|---|---|---|---|---|---|---|---|---|---|
| ccg | gac | cgc | cac | atc | gag | cgg | gtc | acc | gag | ctg | caa | gaa | ctc | ttc | 3699 |
| Pro | Asp | Arg | His | Ile | Glu | Arg | Val | Thr | Glu | Leu | Gln | Glu | Leu | Phe | |
| | 1220 | | | | 1225 | | | | | 1230 | | | | | |

| ctc | acg | cgc | gtc | ggg | ctc | gac | atc | ggc | aag | gtg | tgg | gtc | gcg | gac | 3744 |
| Leu | Thr | Arg | Val | Gly | Leu | Asp | Ile | Gly | Lys | Val | Trp | Val | Ala | Asp | |
| 1235 | | | | | 1240 | | | | | 1245 | | | | | |

| gac | ggc | gcc | gcg | gtg | gcg | gtc | tgg | acc | acg | ccg | gag | agc | gtc | gaa | 3789 |
| Asp | Gly | Ala | Ala | Val | Ala | Val | Trp | Thr | Thr | Pro | Glu | Ser | Val | Glu | |
| 1250 | | | | | 1255 | | | | | 1260 | | | | | |

| gcg | ggg | gcg | gtg | ttc | gcc | gag | atc | ggc | ccg | cgc | atg | gcc | gag | ttg | 3834 |
| Ala | Gly | Ala | Val | Phe | Ala | Glu | Ile | Gly | Pro | Arg | Met | Ala | Glu | Leu | |
| | 1265 | | | | 1270 | | | | | 1275 | | | | | |

| agc | ggt | tcc | cgg | ctg | gcc | gcg | cag | caa | cag | atg | gaa | ggc | ctc | ctg | 3879 |
| Ser | Gly | Ser | Arg | Leu | Ala | Ala | Gln | Gln | Gln | Met | Glu | Gly | Leu | Leu | |
| | 1280 | | | | 1285 | | | | | 1290 | | | | | |

| gcg | ccg | cac | cgg | ccc | aag | gag | ccc | gcg | tgg | ttc | ctg | gcc | acc | gtc | 3924 |
| Ala | Pro | His | Arg | Pro | Lys | Glu | Pro | Ala | Trp | Phe | Leu | Ala | Thr | Val | |
| 1295 | | | | | 1300 | | | | | 1305 | | | | | |

| gga | gtc | tcg | ccc | gac | cac | cag | ggc | aag | ggt | ctg | ggc | agc | gcc | gtc | 3969 |
| Gly | Val | Ser | Pro | Asp | His | Gln | Gly | Lys | Gly | Leu | Gly | Ser | Ala | Val | |
| 1310 | | | | | 1315 | | | | | 1320 | | | | | |

| gtg | ctc | ccc | gga | gtg | gag | gcg | gcc | gag | cgc | gcc | ggg | gtg | ccc | gcc | 4014 |
| Val | Leu | Pro | Gly | Val | Glu | Ala | Ala | Glu | Arg | Ala | Gly | Val | Pro | Ala | |
| 1325 | | | | | 1330 | | | | | 1335 | | | | | |

| ttc | ctg | gaa | acc | tcc | gcg | ccc | cgc | aac | ctc | ccc | ttc | tac | gag | cgg | 4059 |
| Phe | Leu | Glu | Thr | Ser | Ala | Pro | Arg | Asn | Leu | Pro | Phe | Tyr | Glu | Arg | |
| 1340 | | | | | 1345 | | | | | 1350 | | | | | |

| ctc | ggc | ttc | acc | gtc | acc | gcc | gac | gtc | gag | gtg | ccc | gaa | gga | ccg | 4104 |
| Leu | Gly | Phe | Thr | Val | Thr | Ala | Asp | Val | Glu | Val | Pro | Glu | Gly | Pro | |
| 1355 | | | | | 1360 | | | | | 1365 | | | | | |

| cgc | acc | tgg | tgc | atg | acc | cgc | aag | ccc | ggt | gcc | tga | | | | 4140 |
| Arg | Thr | Trp | Cys | Met | Thr | Arg | Lys | Pro | Gly | Ala | | | | | |
| | 1370 | | | | 1375 | | | | | | | | | | |

<210> SEQ ID NO 38
<211> LENGTH: 1379
<212> TYPE: PRT
<213> ORGANISM: Artificial Sequence
<220> FEATURE:
<223> OTHER INFORMATION: Synthetic Construct

<400> SEQUENCE: 38

Met Ala Pro Lys Lys Lys Arg Lys Val Gly Ile His Gly Val Pro Ala
1               5                   10                  15

Ala Lys Arg Asn Tyr Ile Leu Gly Leu Ala Ile Gly Ile Thr Ser Val
                20                  25                  30

Gly Tyr Gly Ile Ile Asp Tyr Glu Thr Arg Asp Val Ile Asp Ala Gly
            35                  40                  45

Val Arg Leu Phe Lys Glu Ala Asn Val Glu Asn Asn Glu Gly Arg Arg
        50                  55                  60

Ser Lys Arg Gly Ala Arg Arg Leu Lys Arg Arg Arg His Arg Ile
65                  70                  75                  80

Gln Arg Val Lys Lys Leu Leu Phe Asp Tyr Asn Leu Leu Thr Asp His
                85                  90                  95

Ser Glu Leu Ser Gly Ile Asn Pro Tyr Glu Ala Arg Val Lys Gly Leu
            100                 105                 110

Ser Gln Lys Leu Ser Glu Glu Glu Phe Ser Ala Ala Leu Leu His Leu
        115                 120                 125

```
Ala Lys Arg Arg Gly Val His Asn Val Asn Glu Val Glu Glu Asp Thr
    130                 135                 140

Gly Asn Glu Leu Ser Thr Lys Glu Gln Ile Ser Arg Asn Ser Lys Ala
145                 150                 155                 160

Leu Glu Glu Lys Tyr Val Ala Glu Leu Gln Leu Glu Arg Leu Lys Lys
                165                 170                 175

Asp Gly Glu Val Arg Gly Ser Ile Asn Arg Phe Lys Thr Ser Asp Tyr
            180                 185                 190

Val Lys Glu Ala Lys Gln Leu Leu Lys Val Gln Lys Ala Tyr His Gln
        195                 200                 205

Leu Asp Gln Ser Phe Ile Asp Thr Tyr Ile Asp Leu Leu Glu Thr Arg
210                 215                 220

Arg Thr Tyr Tyr Glu Gly Pro Gly Glu Gly Ser Pro Phe Gly Trp Lys
225                 230                 235                 240

Asp Ile Lys Glu Trp Tyr Glu Met Leu Met Gly His Cys Thr Tyr Phe
                245                 250                 255

Pro Glu Glu Leu Arg Ser Val Lys Tyr Ala Tyr Asn Ala Asp Leu Tyr
            260                 265                 270

Asn Ala Leu Asn Asp Leu Asn Asn Leu Val Ile Thr Arg Asp Glu Asn
        275                 280                 285

Glu Lys Leu Glu Tyr Tyr Glu Lys Phe Gln Ile Ile Glu Asn Val Phe
    290                 295                 300

Lys Gln Lys Lys Lys Pro Thr Leu Lys Gln Ile Ala Lys Glu Ile Leu
305                 310                 315                 320

Val Asn Glu Glu Asp Ile Lys Gly Tyr Arg Val Thr Ser Thr Gly Lys
                325                 330                 335

Pro Glu Phe Thr Asn Leu Lys Val Tyr His Asp Ile Lys Asp Ile Thr
            340                 345                 350

Ala Arg Lys Glu Ile Ile Glu Asn Ala Glu Leu Leu Asp Gln Ile Ala
        355                 360                 365

Lys Ile Leu Thr Ile Tyr Gln Ser Ser Glu Asp Ile Gln Glu Glu Leu
    370                 375                 380

Thr Asn Leu Asn Ser Glu Leu Thr Gln Glu Glu Ile Glu Gln Ile Ser
385                 390                 395                 400

Asn Leu Lys Gly Tyr Thr Gly Thr His Asn Leu Ser Leu Lys Ala Ile
                405                 410                 415

Asn Leu Ile Leu Asp Glu Leu Trp His Thr Asn Asp Asn Gln Ile Ala
            420                 425                 430

Ile Phe Asn Arg Leu Lys Leu Val Pro Lys Lys Val Asp Leu Ser Gln
        435                 440                 445

Gln Lys Glu Ile Pro Thr Thr Leu Val Asp Asp Phe Ile Leu Ser Pro
    450                 455                 460

Val Val Lys Arg Ser Phe Ile Gln Ser Ile Lys Val Ile Asn Ala Ile
465                 470                 475                 480

Ile Lys Lys Tyr Gly Leu Pro Asn Asp Ile Ile Glu Leu Ala Arg
                485                 490                 495

Glu Lys Asn Ser Lys Asp Ala Gln Lys Met Ile Asn Glu Met Gln Lys
            500                 505                 510

Arg Asn Arg Gln Thr Asn Glu Arg Ile Glu Glu Ile Ile Arg Thr Thr
        515                 520                 525

Gly Lys Glu Asn Ala Lys Tyr Leu Ile Glu Lys Ile Lys Leu His Asp
    530                 535                 540

Met Gln Glu Gly Lys Cys Leu Tyr Ser Leu Glu Ala Ile Pro Leu Glu
```

-continued

```
           545                 550                 555                 560
Asp Leu Leu Asn Asn Pro Phe Asn Tyr Glu Val Asp His Ile Ile Pro
                    565                 570                 575
Arg Ser Val Ser Phe Asp Asn Ser Phe Asn Asn Lys Val Leu Val Lys
                580                 585                 590
Gln Glu Glu Ala Ser Lys Lys Gly Asn Arg Thr Pro Phe Gln Tyr Leu
                595                 600                 605
Ser Ser Ser Asp Ser Lys Ile Ser Tyr Glu Thr Phe Lys Lys His Ile
            610                 615                 620
Leu Asn Leu Ala Lys Gly Lys Gly Arg Ile Ser Lys Thr Lys Lys Glu
625                 630                 635                 640
Tyr Leu Leu Glu Glu Arg Asp Ile Asn Arg Phe Ser Val Gln Lys Asp
                645                 650                 655
Phe Ile Asn Arg Asn Leu Val Asp Thr Arg Tyr Ala Thr Arg Gly Leu
                660                 665                 670
Met Asn Leu Leu Arg Ser Tyr Phe Arg Val Asn Asn Leu Asp Val Lys
            675                 680                 685
Val Lys Ser Ile Asn Gly Gly Phe Thr Ser Phe Leu Arg Arg Lys Trp
690                 695                 700
Lys Phe Lys Lys Glu Arg Asn Lys Gly Tyr Lys His His Ala Glu Asp
705                 710                 715                 720
Ala Leu Ile Ile Ala Asn Ala Asp Phe Ile Phe Lys Glu Trp Lys Lys
                725                 730                 735
Leu Asp Lys Ala Lys Lys Val Met Glu Asn Gln Met Phe Glu Glu Lys
                740                 745                 750
Gln Ala Glu Ser Met Pro Glu Ile Glu Thr Glu Gln Glu Tyr Lys Glu
            755                 760                 765
Ile Phe Ile Thr Pro His Gln Ile Lys His Ile Lys Asp Phe Lys Asp
            770                 775                 780
Tyr Lys Tyr Ser His Arg Val Asp Lys Lys Pro Asn Arg Glu Leu Ile
785                 790                 795                 800
Asn Asp Thr Leu Tyr Ser Thr Arg Lys Asp Asp Lys Gly Asn Thr Leu
                805                 810                 815
Ile Val Asn Asn Leu Asn Gly Leu Tyr Asp Lys Asp Asn Asp Lys Leu
                820                 825                 830
Lys Lys Leu Ile Asn Lys Ser Pro Glu Lys Leu Leu Met Tyr His His
            835                 840                 845
Asp Pro Gln Thr Tyr Gln Lys Leu Lys Leu Ile Met Glu Gln Tyr Gly
850                 855                 860
Asp Glu Lys Asn Pro Leu Tyr Lys Tyr Tyr Glu Glu Thr Gly Asn Tyr
865                 870                 875                 880
Leu Thr Lys Tyr Ser Lys Lys Asp Asn Gly Pro Val Ile Lys Lys Ile
                885                 890                 895
Lys Tyr Tyr Gly Asn Lys Leu Asn Ala His Leu Asp Ile Thr Asp Asp
                900                 905                 910
Tyr Pro Asn Ser Arg Asn Lys Val Val Lys Leu Ser Leu Lys Pro Tyr
            915                 920                 925
Arg Phe Asp Val Tyr Leu Asp Asn Gly Val Tyr Lys Phe Val Thr Val
            930                 935                 940
Lys Asn Leu Asp Val Ile Lys Lys Glu Asn Tyr Tyr Glu Val Asn Ser
945                 950                 955                 960
Lys Cys Tyr Glu Glu Ala Lys Lys Leu Lys Lys Ile Ser Asn Gln Ala
                965                 970                 975
```

```
Glu Phe Ile Ala Ser Phe Tyr Asn Asn Asp Leu Ile Lys Ile Asn Gly
                980                 985                 990

Glu Leu Tyr Arg Val Ile Gly Val  Asn Asn Asp Leu Leu  Asn Arg Ile
            995                 1000                1005

Glu Val Asn Met Ile Asp Ile  Thr Tyr Arg Glu Tyr  Leu Glu Asn
        1010                1015                1020

Met Asn Asp Lys Arg Pro Pro  Arg Ile Ile Lys Thr  Ile Ala Ser
        1025                1030                1035

Lys Thr Gln Ser Ile Lys Lys  Tyr Ser Thr Asp Ile  Leu Gly Asn
        1040                1045                1050

Leu Tyr Glu Val Lys Ser Lys  Lys His Pro Gln Ile  Ile Lys Lys
        1055                1060                1065

Gly Lys Arg Pro Ala Ala Thr  Lys Lys Ala Gly Gln  Ala Lys Lys
        1070                1075                1080

Lys Lys Gly Ser Met Asp Ala  Lys Ser Leu Thr Ala  Trp Ser Arg
        1085                1090                1095

Thr Leu Val Thr Phe Lys Asp  Val Phe Val Asp Phe  Thr Arg Glu
        1100                1105                1110

Glu Trp Lys Leu Leu Asp Thr  Ala Gln Gln Ile Val  Tyr Arg Asn
        1115                1120                1125

Val Met Leu Glu Asn Tyr Lys  Asn Leu Val Ser Leu  Gly Tyr Gln
        1130                1135                1140

Leu Thr Lys Pro Asp Val Ile  Leu Arg Leu Glu Lys  Gly Glu Glu
        1145                1150                1155

Pro Gly Ser Gly Ala Thr Asn  Phe Ser Leu Leu Lys  Gln Ala Gly
        1160                1165                1170

Asp Val Glu Glu Asn Pro Gly  Pro Thr Glu Tyr Lys  Pro Thr Val
        1175                1180                1185

Arg Leu Ala Thr Arg Asp Asp  Val Pro Arg Ala Val  Arg Thr Leu
        1190                1195                1200

Ala Ala Ala Phe Ala Asp Tyr  Pro Ala Thr Arg His  Thr Val Asp
        1205                1210                1215

Pro Asp Arg His Ile Glu Arg  Val Thr Glu Leu Gln  Glu Leu Phe
        1220                1225                1230

Leu Thr Arg Val Gly Leu Asp  Ile Gly Lys Val Trp  Val Ala Asp
        1235                1240                1245

Asp Gly Ala Ala Val Ala Val  Trp Thr Thr Pro Glu  Ser Val Glu
        1250                1255                1260

Ala Gly Ala Val Phe Ala Glu  Ile Gly Pro Arg Met  Ala Glu Leu
        1265                1270                1275

Ser Gly Ser Arg Leu Ala Ala  Gln Gln Gln Met Glu  Gly Leu Leu
        1280                1285                1290

Ala Pro His Arg Pro Lys Glu  Pro Ala Trp Phe Leu  Ala Thr Val
        1295                1300                1305

Gly Val Ser Pro Asp His Gln  Gly Lys Gly Leu Gly  Ser Ala Val
        1310                1315                1320

Val Leu Pro Gly Val Glu Ala  Ala Glu Arg Ala Gly  Val Pro Ala
        1325                1330                1335

Phe Leu Glu Thr Ser Ala Pro  Arg Asn Leu Pro Phe  Tyr Glu Arg
        1340                1345                1350

Leu Gly Phe Thr Val Thr Ala  Asp Val Glu Val Pro  Glu Gly Pro
        1355                1360                1365
```

<210> SEQ ID NO 39
<211> LENGTH: 4140
<212> TYPE: DNA
<213> ORGANISM: Artificial Sequence
<220> FEATURE:
<223> OTHER INFORMATION: NLS-PF(v15)dSaCas9(D10A,N580A)-NLS-KRAB-P2A-
    Puro fusion protein
<220> FEATURE:
<221> NAME/KEY: CDS
<222> LOCATION: (1)..(4140)

<400> SEQUENCE: 39

```
                                                                          -continued
Arg Thr Trp Cys Met Thr Arg Lys Pro Gly Ala
    1370                1375 atg gcc cca aag aag aag cgg aag gtc ggt atc cac gga gtc cca gca      48
Met Ala Pro Lys Lys Lys Arg Lys Val Gly Ile His Gly Val Pro Ala
1               5                   10                  15 gcc aag cgg aac tac atc ctg ggc ctg gcc atc ggc atc acc agc gtg      96
Ala Lys Arg Asn Tyr Ile Leu Gly Leu Ala Ile Gly Ile Thr Ser Val
                20                  25                  30 ggc tac ggc atc atc gac tac gag aca cgg gac gtg atc gat gcc ggc     144
Gly Tyr Gly Ile Ile Asp Tyr Glu Thr Arg Asp Val Ile Asp Ala Gly
            35                  40                  45 gtg cgg ctg ttc aaa gag gcc aac gtg gaa aac aac gag ggc agg cgg     192
Val Arg Leu Phe Lys Glu Ala Asn Val Glu Asn Asn Glu Gly Arg Arg
        50                  55                  60 agc aag aga ggc gcc aga agg ctg aag cgg agg agg cgg cat aga atc     240
Ser Lys Arg Gly Ala Arg Arg Leu Lys Arg Arg Arg Arg His Arg Ile
    65                  70                  75                  80 cag aga gtg aag aag ctg ctg ttc gac tac aac ctg ctg acc gac cac     288
Gln Arg Val Lys Lys Leu Leu Phe Asp Tyr Asn Leu Leu Thr Asp His
                85                  90                  95 agc gag ctg agc ggc atc aac ccc tac gag gcc aga gtg aag ggc ctg     336
Ser Glu Leu Ser Gly Ile Asn Pro Tyr Glu Ala Arg Val Lys Gly Leu
                100                 105                 110 agc cag aag ctg agc gag gaa gag ttc tct gcc gcc ctg ctg cac ctg     384
Ser Gln Lys Leu Ser Glu Glu Glu Phe Ser Ala Ala Leu Leu His Leu
            115                 120                 125 gcc aag aga aga ggc gtg cac aac gtg aac gag gtg gaa gag gac acc     432
Ala Lys Arg Arg Gly Val His Asn Val Asn Glu Val Glu Glu Asp Thr
        130                 135                 140 ggc aac gag ctg tcc acc aaa gag cag atc agc cgg aac agc aag gcc     480
Gly Asn Glu Leu Ser Thr Lys Glu Gln Ile Ser Arg Asn Ser Lys Ala
    145                 150                 155                 160 ctg gaa gag aaa tac gtg gcc gaa ctg cag ctg gaa cgg ctg aag aaa     528
Leu Glu Glu Lys Tyr Val Ala Glu Leu Gln Leu Glu Arg Leu Lys Lys
                165                 170                 175 gac ggc gaa gtg cgg ggc agc atc aac aga ttc aag acc agc gac tac     576
Asp Gly Glu Val Arg Gly Ser Ile Asn Arg Phe Lys Thr Ser Asp Tyr
                180                 185                 190 gtg aaa gaa gcc aaa cag ctg ctg aag gtg cag aag gcc tac cac cag     624
Val Lys Glu Ala Lys Gln Leu Leu Lys Val Gln Lys Ala Tyr His Gln
            195                 200                 205 ctg gac cag agc ttc atc gac acc tac atc gac ctg ctg gaa acc cgg     672
Leu Asp Gln Ser Phe Ile Asp Thr Tyr Ile Asp Leu Leu Glu Thr Arg
        210                 215                 220 cgg acc tac tat gag gga cct ggc gag ggc agc ccc ttc ggc tgg aag     720
Arg Thr Tyr Tyr Glu Gly Pro Gly Glu Gly Ser Pro Phe Gly Trp Lys
    225                 230                 235                 240 gac atc aaa gaa tgg tac gag atg ctg atg ggc cac tgc acc tac ttc     768
Asp Ile Lys Glu Trp Tyr Glu Met Leu Met Gly His Cys Thr Tyr Phe
```

```
                   245                 250                 255
ccc gag gaa ctg cgg agc gtg aag tac gcc tac aac gcc gac ctg tac      816
Pro Glu Glu Leu Arg Ser Val Lys Tyr Ala Tyr Asn Ala Asp Leu Tyr
            260                 265                 270 aac gcc ctg aac gac ctg aac aat ctc gtg atc acc agg gac gag aac      864
Asn Ala Leu Asn Asp Leu Asn Asn Leu Val Ile Thr Arg Asp Glu Asn
                275                 280                 285 gag aag ctg gaa tat tac gag aag ttc cag atc atc gag aac gtg ttc      912
Glu Lys Leu Glu Tyr Tyr Glu Lys Phe Gln Ile Ile Glu Asn Val Phe
290                 295                 300 aag cag aag aag aag ccc acc ctg aag cag atc gcc aaa gaa atc ctc      960
Lys Gln Lys Lys Lys Pro Thr Leu Lys Gln Ile Ala Lys Glu Ile Leu
305                 310                 315                 320 gtg aac gaa gag gat att aag ggc tac aga gtg acc agc acc ggc aag     1008
Val Asn Glu Glu Asp Ile Lys Gly Tyr Arg Val Thr Ser Thr Gly Lys
                325                 330                 335 ccc gag ttc acc aac ctg aag gtg tac cac gac atc aag gac att acc     1056
Pro Glu Phe Thr Asn Leu Lys Val Tyr His Asp Ile Lys Asp Ile Thr
                340                 345                 350 gcc cgg aaa gag att att gag aac gcc gag ctg ctg gat cag att gcc     1104
Ala Arg Lys Glu Ile Ile Glu Asn Ala Glu Leu Leu Asp Gln Ile Ala
            355                 360                 365 aag atc ctg acc atc tac cag agc agc gag gac atc cag gaa gaa ctg     1152
Lys Ile Leu Thr Ile Tyr Gln Ser Ser Glu Asp Ile Gln Glu Glu Leu
370                 375                 380 acc aat ctg aac tcc gag ctg acc cag gaa gag atc gag cag atc tct     1200
Thr Asn Leu Asn Ser Glu Leu Thr Gln Glu Glu Ile Glu Gln Ile Ser
385                 390                 395                 400 aat ctg aag ggc tat acc ggc acc cac aac ctg agc ctg aag gcc atc     1248
Asn Leu Lys Gly Tyr Thr Gly Thr His Asn Leu Ser Leu Lys Ala Ile
                405                 410                 415 aac ctg atc ctg gac gag ctg tgg cac acc aac gac aac cag atc gct     1296
Asn Leu Ile Leu Asp Glu Leu Trp His Thr Asn Asp Asn Gln Ile Ala
            420                 425                 430 atc ttc aac cgg ctg aag ctg gtg ccc aag aag gtg gac ctg tcc cag     1344
Ile Phe Asn Arg Leu Lys Leu Val Pro Lys Lys Val Asp Leu Ser Gln
            435                 440                 445 cag aaa gag atc ccc acc acc ctg gtg gac gac ttc atc ctg agc ccc     1392
Gln Lys Glu Ile Pro Thr Thr Leu Val Asp Asp Phe Ile Leu Ser Pro
    450                 455                 460 gtc gtg aag aga agc ttc atc cag agc atc aaa gtg atc aac gcc atc     1440
Val Val Lys Arg Ser Phe Ile Gln Ser Ile Lys Val Ile Asn Ala Ile
465                 470                 475                 480 atc aag aag tac ggc ctg ccc aac gac atc att atc gag ctg gcc cgc     1488
Ile Lys Lys Tyr Gly Leu Pro Asn Asp Ile Ile Ile Glu Leu Ala Arg
                485                 490                 495 gag aag aac tcc aag gac gcc cag aaa atg atc aac gag atg cag aag     1536
Glu Lys Asn Ser Lys Asp Ala Gln Lys Met Ile Asn Glu Met Gln Lys
                500                 505                 510 cgg aac cgg cag acc aac gag cgg atc gag gaa atc atc cgg acc acc     1584
Arg Asn Arg Gln Thr Asn Glu Arg Ile Glu Glu Ile Ile Arg Thr Thr
            515                 520                 525 ggc aaa gag aac gcc aag tac ctg atc gag aag atc aag ctg cac gac     1632
Gly Lys Glu Asn Ala Lys Tyr Leu Ile Glu Lys Ile Lys Leu His Asp
530                 535                 540 atg cag gaa ggc aag tgc ctg tac agc ctg gaa gcc atc cct ctg gaa     1680
Met Gln Glu Gly Lys Cys Leu Tyr Ser Leu Glu Ala Ile Pro Leu Glu
545                 550                 555                 560 gat ctg ctg aac aac ccc ttc aac tat gag gtg gac cac atc atc ccc     1728
Asp Leu Leu Asn Asn Pro Phe Asn Tyr Glu Val Asp His Ile Ile Pro
```

```
                Asp Leu Leu Asn Asn Pro Phe Asn Tyr Glu Val Asp His Ile Ile Pro
                                565                 570                 575 aga agc gtg tcc ttc gac aac agc ttc aac aac aag gtg ctc gtg aag          1776
Arg Ser Val Ser Phe Asp Asn Ser Phe Asn Asn Lys Val Leu Val Lys
            580                 585                 590 cag gaa gaa gcc agc aag aag ggc aac cgg acc cca ttc cag tac ctg          1824
Gln Glu Glu Ala Ser Lys Lys Gly Asn Arg Thr Pro Phe Gln Tyr Leu
            595                 600                 605 agc agc agc gac agc aag atc agc tac gaa acc ttc aag aag cac atc          1872
Ser Ser Ser Asp Ser Lys Ile Ser Tyr Glu Thr Phe Lys Lys His Ile
            610                 615                 620 ctg aat ctg gcc aag ggc aag ggc aga atc agc aag acc aag aaa gag          1920
Leu Asn Leu Ala Lys Gly Lys Gly Arg Ile Ser Lys Thr Lys Lys Glu
625                 630                 635                 640 tat ctg ctg gaa gaa cgg gac atc aac agg ttc tcc gtg cag aaa gac          1968
Tyr Leu Leu Glu Glu Arg Asp Ile Asn Arg Phe Ser Val Gln Lys Asp
                645                 650                 655 ttc atc aac cgg aac ctg gtg gat acc aga tac gcc acc aga ggc ctg          2016
Phe Ile Asn Arg Asn Leu Val Asp Thr Arg Tyr Ala Thr Arg Gly Leu
                660                 665                 670 atg aac ctg ctg cgg agc tac ttc aga gtg aac aac ctg gac gtg aaa          2064
Met Asn Leu Leu Arg Ser Tyr Phe Arg Val Asn Asn Leu Asp Val Lys
            675                 680                 685 gtg aag tcc atc aat ggc ggc ttc acc agc ttt ctg cgg cgg aag tgg          2112
Val Lys Ser Ile Asn Gly Gly Phe Thr Ser Phe Leu Arg Arg Lys Trp
690                 695                 700 aag ttt aag aaa gag cgg aac aag ggg tac aag cac cac gcc gag gac          2160
Lys Phe Lys Lys Glu Arg Asn Lys Gly Tyr Lys His His Ala Glu Asp
705                 710                 715                 720 gcc ctg atc att gcc aac gcc gat ttc atc ttc aaa gag tgg aag aaa          2208
Ala Leu Ile Ile Ala Asn Ala Asp Phe Ile Phe Lys Glu Trp Lys Lys
                725                 730                 735 ctg gac aag gcc aaa aaa gtg atg gaa aac cag atg ttc gag gaa aag          2256
Leu Asp Lys Ala Lys Lys Val Met Glu Asn Gln Met Phe Glu Glu Lys
            740                 745                 750 cag gcc gag agc atg ccc gag atc gaa acc gag cag gag tac aaa gag          2304
Gln Ala Glu Ser Met Pro Glu Ile Glu Thr Glu Gln Glu Tyr Lys Glu
            755                 760                 765 atc ttc atc acc ccc cac cag atc aag cac att aag gac ttc aag gac          2352
Ile Phe Ile Thr Pro His Gln Ile Lys His Ile Lys Asp Phe Lys Asp
770                 775                 780 tac aag tac agc cac cgg gtg gac aag aag cct aat aga aag ctg att          2400
Tyr Lys Tyr Ser His Arg Val Asp Lys Lys Pro Asn Arg Lys Leu Ile
785                 790                 795                 800 aac gac acc ctg tac tcc acc cgg aag gac gac aag ggc aac acc cgg          2448
Asn Asp Thr Leu Tyr Ser Thr Arg Lys Asp Asp Lys Gly Asn Thr Arg
                805                 810                 815 atc gtg aac aat ctg aac ggc ctg tac gac aag gac aat gac aag ctg          2496
Ile Val Asn Asn Leu Asn Gly Leu Tyr Asp Lys Asp Asn Asp Lys Leu
            820                 825                 830 aaa aag ctg atc aac aag agc ccc gaa aag ctg ctg atg tac cac cac          2544
Lys Lys Leu Ile Asn Lys Ser Pro Glu Lys Leu Leu Met Tyr His His
            835                 840                 845 gac ccc cag acc tac cag aaa ctg aag ctg att atg gaa cag tac ggc          2592
Asp Pro Gln Thr Tyr Gln Lys Leu Lys Leu Ile Met Glu Gln Tyr Gly
            850                 855                 860 gac gag aag aat ccc ctg tac aag tac tac gag gaa acc ggg aac tac          2640
Asp Glu Lys Asn Pro Leu Tyr Lys Tyr Tyr Glu Glu Thr Gly Asn Tyr
865                 870                 875                 880
```

```
ctg acc aag tac tcc aaa aag gac aac ggc ccc gtg atc aag aag att    2688
Leu Thr Lys Tyr Ser Lys Lys Asp Asn Gly Pro Val Ile Lys Lys Ile
            885                 890                 895 aag tat tac ggc aac aaa ctg aac aga cat ctg gac atc acc gac gac    2736
Lys Tyr Tyr Gly Asn Lys Leu Asn Arg His Leu Asp Ile Thr Asp Asp
        900                 905                 910 tac ccc aac agc aga aac aag gtc gtg aag ctg tcc ctg aag ccc tac    2784
Tyr Pro Asn Ser Arg Asn Lys Val Val Lys Leu Ser Leu Lys Pro Tyr
            915                 920                 925 aga ttc gac gtg tac ctg gac aat ggc gtg tac aag ttc gtg acc gtg    2832
Arg Phe Asp Val Tyr Leu Asp Asn Gly Val Tyr Lys Phe Val Thr Val
        930                 935                 940 aag aat ctg gat gtg atc aaa aaa gaa aac tac tac gaa gtg aat agc    2880
Lys Asn Leu Asp Val Ile Lys Lys Glu Asn Tyr Tyr Glu Val Asn Ser
945                 950                 955                 960 aag tgc tat gag gaa gct aag aag ctg aag aag atc agc aac cag gcc    2928
Lys Cys Tyr Glu Glu Ala Lys Lys Leu Lys Lys Ile Ser Asn Gln Ala
            965                 970                 975 gag ttt atc gcc tcc ttc tac aga aac gat ctg atc aag atc aac ggc    2976
Glu Phe Ile Ala Ser Phe Tyr Arg Asn Asp Leu Ile Lys Ile Asn Gly
        980                 985                 990 gag ctg tat aga gtg atc ggc gtg gcg gcc gac cac ctg aac gcc atc    3024
Glu Leu Tyr Arg Val Ile Gly Val Ala Ala Asp His Leu Asn Ala Ile
        995                 1000                1005 gaa gtg aac atg atc gac atc acc tac cgc gag tac ctg gaa aac        3069
Glu Val Asn Met Ile Asp Ile Thr Tyr Arg Glu Tyr Leu Glu Asn
    1010                1015                1020 atg aac gac aag agg ccc ccc agg atc att aag aca atc agc tcc        3114
Met Asn Asp Lys Arg Pro Pro Arg Ile Ile Lys Thr Ile Ser Ser
    1025                1030                1035 aag acc cag agc att aag aag tac agc aca gac att ctg ggc aac        3159
Lys Thr Gln Ser Ile Lys Lys Tyr Ser Thr Asp Ile Leu Gly Asn
    1040                1045                1050 ctg tat gaa gtg aaa tct aag aag cac cct cag atc atc aaa aag        3204
Leu Tyr Glu Val Lys Ser Lys Lys His Pro Gln Ile Ile Lys Lys
    1055                1060                1065 ggc aaa agg ccg gcg gcc acg aaa aag gcc ggc cag gca aaa aag        3249
Gly Lys Arg Pro Ala Ala Thr Lys Lys Ala Gly Gln Ala Lys Lys
    1070                1075                1080 aaa aag gga tcc atg gat gct aag tca cta act gcc tgg tcc cgg        3294
Lys Lys Gly Ser Met Asp Ala Lys Ser Leu Thr Ala Trp Ser Arg
    1085                1090                1095 aca ctg gtg acc ttc aag gat gta ttt gtg gac ttc acc agg gag        3339
Thr Leu Val Thr Phe Lys Asp Val Phe Val Asp Phe Thr Arg Glu
    1100                1105                1110 gag tgg aag ctg ctg gac act gct cag cag atc gtg tac aga aat        3384
Glu Trp Lys Leu Leu Asp Thr Ala Gln Gln Ile Val Tyr Arg Asn
    1115                1120                1125 gtg atg ctg gag aac tat aag aac ctg gtt tcc ttg ggt tat cag        3429
Val Met Leu Glu Asn Tyr Lys Asn Leu Val Ser Leu Gly Tyr Gln
    1130                1135                1140 ctt act aag cca gat gtg atc ctc cgg ttg gag aag gga gaa gag        3474
Leu Thr Lys Pro Asp Val Ile Leu Arg Leu Glu Lys Gly Glu Glu
    1145                1150                1155 ccc gga agc ggt gct act aac ttc agc ctg ctg aag cag gct gga        3519
Pro Gly Ser Gly Ala Thr Asn Phe Ser Leu Leu Lys Gln Ala Gly
    1160                1165                1170 gac gtg gag gag aac cct gga cct acc gag tac aag ccc acg gtg        3564
Asp Val Glu Glu Asn Pro Gly Pro Thr Glu Tyr Lys Pro Thr Val
    1175                1180                1185
```

```
cgc ctc gcc acc cgc gac gac gtc ccc agg gcc gta cgc acc ctc      3609
Arg Leu Ala Thr Arg Asp Asp Val Pro Arg Ala Val Arg Thr Leu
    1190                1195                1200 gcc gcc gcg ttc gcc gac tac ccc gcc acg cgc cac acc gtc gat      3654
Ala Ala Ala Phe Ala Asp Tyr Pro Ala Thr Arg His Thr Val Asp
    1205                1210                1215 ccg gac cgc cac atc gag cgg gtc acc gag ctg caa gaa ctc ttc      3699
Pro Asp Arg His Ile Glu Arg Val Thr Glu Leu Gln Glu Leu Phe
    1220                1225                1230 ctc acg cgc gtc ggg ctc gac atc ggc aag gtg tgg gtc gcg gac      3744
Leu Thr Arg Val Gly Leu Asp Ile Gly Lys Val Trp Val Ala Asp
    1235                1240                1245 gac ggc gcc gcg gtg gcg gtc tgg acc acg ccg gag agc gtc gaa      3789
Asp Gly Ala Ala Val Ala Val Trp Thr Thr Pro Glu Ser Val Glu
    1250                1255                1260 gcg ggg gcg gtg ttc gcc gag atc ggc ccg cgc atg gcc gag ttg      3834
Ala Gly Ala Val Phe Ala Glu Ile Gly Pro Arg Met Ala Glu Leu
    1265                1270                1275 agc ggt tcc cgg ctg gcc gcg cag caa cag atg gaa ggc ctc ctg      3879
Ser Gly Ser Arg Leu Ala Ala Gln Gln Gln Met Glu Gly Leu Leu
    1280                1285                1290 gcg ccg cac cgg ccc aag gag ccc gcg tgg ttc ctg gcc acc gtc      3924
Ala Pro His Arg Pro Lys Glu Pro Ala Trp Phe Leu Ala Thr Val
    1295                1300                1305 gga gtc tcg ccc gac cac cag ggc aag ggt ctg ggc agc gcc gtc      3969
Gly Val Ser Pro Asp His Gln Gly Lys Gly Leu Gly Ser Ala Val
    1310                1315                1320 gtg ctc ccc gga gtg gag gcg gcc gag cgc gcc ggg gtg ccc gcc      4014
Val Leu Pro Gly Val Glu Ala Ala Glu Arg Ala Gly Val Pro Ala
    1325                1330                1335 ttc ctg gaa acc tcc gcg ccc cgc aac ctc ccc ttc tac gag cgg      4059
Phe Leu Glu Thr Ser Ala Pro Arg Asn Leu Pro Phe Tyr Glu Arg
    1340                1345                1350 ctc ggc ttc acc gtc acc gcc gac gtc gag gtg ccc gaa gga ccg      4104
Leu Gly Phe Thr Val Thr Ala Asp Val Glu Val Pro Glu Gly Pro
    1355                1360                1365 cgc acc tgg tgc atg acc cgc aag ccc ggt gcc tga                  4140
Arg Thr Trp Cys Met Thr Arg Lys Pro Gly Ala
    1370                1375
```

```
<210> SEQ ID NO 40
<211> LENGTH: 1379
<212> TYPE: PRT
<213> ORGANISM: Artificial Sequence
<220> FEATURE:
<223> OTHER INFORMATION: Synthetic Construct

<400> SEQUENCE: 40

Met Ala Pro Lys Lys Lys Arg Lys Val Gly Ile His Gly Val Pro Ala
1               5                   10                  15

Ala Lys Arg Asn Tyr Ile Leu Gly Leu Ala Ile Gly Ile Thr Ser Val
            20                  25                  30

Gly Tyr Gly Ile Ile Asp Tyr Glu Thr Arg Asp Val Ile Asp Ala Gly
        35                  40                  45

Val Arg Leu Phe Lys Glu Ala Asn Val Glu Asn Asn Glu Gly Arg Arg
    50                  55                  60

Ser Lys Arg Gly Ala Arg Arg Leu Lys Arg Arg Arg His Arg Ile
65                  70                  75                  80

Gln Arg Val Lys Lys Leu Leu Phe Asp Tyr Asn Leu Leu Thr Asp His
```

```
            85                  90                  95
Ser Glu Leu Ser Gly Ile Asn Pro Tyr Glu Arg Val Lys Gly Leu
            100                 105                 110

Ser Gln Lys Leu Ser Glu Glu Phe Ser Ala Ala Leu Leu His Leu
            115                 120                 125

Ala Lys Arg Arg Gly Val His Asn Val Asn Glu Val Glu Glu Asp Thr
130                 135                 140

Gly Asn Glu Leu Ser Thr Lys Glu Gln Ile Ser Arg Asn Ser Lys Ala
145                 150                 155                 160

Leu Glu Glu Lys Tyr Val Ala Glu Leu Gln Leu Glu Arg Leu Lys Lys
                165                 170                 175

Asp Gly Glu Val Arg Gly Ser Ile Asn Arg Phe Lys Thr Ser Asp Tyr
            180                 185                 190

Val Lys Glu Ala Lys Gln Leu Leu Lys Val Gln Lys Ala Tyr His Gln
            195                 200                 205

Leu Asp Gln Ser Phe Ile Asp Thr Tyr Ile Asp Leu Leu Glu Thr Arg
210                 215                 220

Arg Thr Tyr Tyr Glu Gly Pro Gly Glu Gly Ser Pro Phe Gly Trp Lys
225                 230                 235                 240

Asp Ile Lys Glu Trp Tyr Glu Met Leu Met Gly His Cys Thr Tyr Phe
                245                 250                 255

Pro Glu Glu Leu Arg Ser Val Lys Tyr Ala Tyr Asn Ala Asp Leu Tyr
            260                 265                 270

Asn Ala Leu Asn Asp Leu Asn Asn Leu Val Ile Thr Arg Asp Glu Asn
            275                 280                 285

Glu Lys Leu Glu Tyr Tyr Glu Lys Phe Gln Ile Ile Glu Asn Val Phe
290                 295                 300

Lys Gln Lys Lys Lys Pro Thr Leu Lys Gln Ile Ala Lys Glu Ile Leu
305                 310                 315                 320

Val Asn Glu Glu Asp Ile Lys Gly Tyr Arg Val Thr Ser Thr Gly Lys
                325                 330                 335

Pro Glu Phe Thr Asn Leu Lys Val Tyr His Asp Ile Lys Asp Ile Thr
            340                 345                 350

Ala Arg Lys Glu Ile Ile Glu Asn Ala Glu Leu Leu Asp Gln Ile Ala
            355                 360                 365

Lys Ile Leu Thr Ile Tyr Gln Ser Ser Glu Asp Ile Gln Glu Glu Leu
370                 375                 380

Thr Asn Leu Asn Ser Glu Leu Thr Gln Glu Glu Ile Glu Gln Ile Ser
385                 390                 395                 400

Asn Leu Lys Gly Tyr Thr Gly Thr His Asn Leu Ser Leu Lys Ala Ile
                405                 410                 415

Asn Leu Ile Leu Asp Glu Leu Trp His Thr Asn Asp Asn Gln Ile Ala
            420                 425                 430

Ile Phe Asn Arg Leu Lys Leu Val Pro Lys Lys Val Asp Leu Ser Gln
            435                 440                 445

Gln Lys Glu Ile Pro Thr Thr Leu Val Asp Asp Phe Ile Leu Ser Pro
450                 455                 460

Val Val Lys Arg Ser Phe Ile Gln Ser Ile Lys Val Ile Asn Ala Ile
465                 470                 475                 480

Ile Lys Lys Tyr Gly Leu Pro Asn Asp Ile Ile Ile Glu Leu Ala Arg
                485                 490                 495

Glu Lys Asn Ser Lys Asp Ala Gln Lys Met Ile Asn Glu Met Gln Lys
            500                 505                 510
```

```
Arg Asn Arg Gln Thr Asn Glu Arg Ile Glu Glu Ile Arg Thr Thr
        515                 520                 525

Gly Lys Glu Asn Ala Lys Tyr Leu Ile Glu Lys Ile Lys Leu His Asp
        530                 535                 540

Met Gln Glu Gly Lys Cys Leu Tyr Ser Leu Glu Ala Ile Pro Leu Glu
545                 550                 555                 560

Asp Leu Leu Asn Asn Pro Phe Asn Tyr Glu Val Asp His Ile Ile Pro
                565                 570                 575

Arg Ser Val Ser Phe Asp Asn Ser Phe Asn Asn Lys Val Leu Val Lys
                580                 585                 590

Gln Glu Glu Ala Ser Lys Lys Gly Asn Arg Thr Pro Phe Gln Tyr Leu
        595                 600                 605

Ser Ser Ser Asp Ser Lys Ile Ser Tyr Glu Thr Phe Lys Lys His Ile
        610                 615                 620

Leu Asn Leu Ala Lys Gly Lys Gly Arg Ile Ser Lys Thr Lys Lys Glu
625                 630                 635                 640

Tyr Leu Leu Glu Glu Arg Asp Ile Asn Arg Phe Ser Val Gln Lys Asp
                645                 650                 655

Phe Ile Asn Arg Asn Leu Val Asp Thr Arg Tyr Ala Thr Arg Gly Leu
                660                 665                 670

Met Asn Leu Leu Arg Ser Tyr Phe Arg Val Asn Asn Leu Asp Val Lys
        675                 680                 685

Val Lys Ser Ile Asn Gly Gly Phe Thr Ser Phe Leu Arg Arg Lys Trp
        690                 695                 700

Lys Phe Lys Lys Glu Arg Asn Lys Gly Tyr Lys His His Ala Glu Asp
705                 710                 715                 720

Ala Leu Ile Ile Ala Asn Ala Asp Phe Ile Phe Lys Glu Trp Lys Lys
                725                 730                 735

Leu Asp Lys Ala Lys Lys Val Met Glu Asn Gln Met Phe Glu Glu Lys
                740                 745                 750

Gln Ala Glu Ser Met Pro Glu Ile Glu Thr Glu Gln Glu Tyr Lys Glu
        755                 760                 765

Ile Phe Ile Thr Pro His Gln Ile Lys His Ile Lys Asp Phe Lys Asp
        770                 775                 780

Tyr Lys Tyr Ser His Arg Val Asp Lys Lys Pro Asn Arg Lys Leu Ile
785                 790                 795                 800

Asn Asp Thr Leu Tyr Ser Thr Arg Lys Asp Asp Lys Gly Asn Thr Arg
                805                 810                 815

Ile Val Asn Asn Leu Asn Gly Leu Tyr Asp Lys Asp Asn Asp Lys Leu
                820                 825                 830

Lys Lys Leu Ile Asn Lys Ser Pro Glu Lys Leu Leu Met Tyr His His
        835                 840                 845

Asp Pro Gln Thr Tyr Gln Lys Leu Lys Leu Ile Met Glu Gln Tyr Gly
850                 855                 860

Asp Glu Lys Asn Pro Leu Tyr Lys Tyr Tyr Glu Glu Thr Gly Asn Tyr
865                 870                 875                 880

Leu Thr Lys Tyr Ser Lys Lys Asp Asn Gly Pro Val Ile Lys Lys Ile
                885                 890                 895

Lys Tyr Tyr Gly Asn Lys Leu Asn Arg His Leu Asp Ile Thr Asp Asp
                900                 905                 910

Tyr Pro Asn Ser Arg Asn Lys Val Val Lys Leu Ser Leu Lys Pro Tyr
        915                 920                 925
```

```
Arg Phe Asp Val Tyr Leu Asp Asn Gly Val Tyr Lys Phe Val Thr Val
    930             935                 940

Lys Asn Leu Asp Val Ile Lys Glu Asn Tyr Tyr Glu Val Asn Ser
945             950                 955                 960

Lys Cys Tyr Glu Glu Ala Lys Lys Leu Lys Lys Ile Ser Asn Gln Ala
            965                 970                 975

Glu Phe Ile Ala Ser Phe Tyr Arg Asn Asp Leu Ile Lys Ile Asn Gly
            980                 985                 990

Glu Leu Tyr Arg Val Ile Gly Val Ala Ala Asp His Leu Asn Ala Ile
            995                 1000                1005

Glu Val Asn Met Ile Asp Ile Thr Tyr Arg Glu Tyr Leu Glu Asn
    1010                1015                1020

Met Asn Asp Lys Arg Pro Pro Arg Ile Ile Lys Thr Ile Ser Ser
    1025                1030                1035

Lys Thr Gln Ser Ile Lys Lys Tyr Ser Thr Asp Ile Leu Gly Asn
    1040                1045                1050

Leu Tyr Glu Val Lys Ser Lys His Pro Gln Ile Ile Lys Lys
    1055                1060                1065

Gly Lys Arg Pro Ala Ala Thr Lys Lys Ala Gly Gln Ala Lys Lys
    1070                1075                1080

Lys Lys Gly Ser Met Asp Ala Lys Ser Leu Thr Ala Trp Ser Arg
    1085                1090                1095

Thr Leu Val Thr Phe Lys Asp Val Phe Val Asp Phe Thr Arg Glu
    1100                1105                1110

Glu Trp Lys Leu Leu Asp Thr Ala Gln Gln Ile Val Tyr Arg Asn
    1115                1120                1125

Val Met Leu Glu Asn Tyr Lys Asn Leu Val Ser Leu Gly Tyr Gln
    1130                1135                1140

Leu Thr Lys Pro Asp Val Ile Leu Arg Leu Glu Lys Gly Glu Glu
    1145                1150                1155

Pro Gly Ser Gly Ala Thr Asn Phe Ser Leu Leu Lys Gln Ala Gly
    1160                1165                1170

Asp Val Glu Glu Asn Pro Gly Pro Thr Glu Tyr Lys Pro Thr Val
    1175                1180                1185

Arg Leu Ala Thr Arg Asp Asp Val Pro Arg Ala Val Arg Thr Leu
    1190                1195                1200

Ala Ala Ala Phe Ala Asp Tyr Pro Ala Thr Arg His Thr Val Asp
    1205                1210                1215

Pro Asp Arg His Ile Glu Arg Val Thr Glu Leu Gln Glu Leu Phe
    1220                1225                1230

Leu Thr Arg Val Gly Leu Asp Ile Gly Lys Val Trp Val Ala Asp
    1235                1240                1245

Asp Gly Ala Ala Val Ala Val Trp Thr Thr Pro Glu Ser Val Glu
    1250                1255                1260

Ala Gly Ala Val Phe Ala Glu Ile Gly Pro Arg Met Ala Glu Leu
    1265                1270                1275

Ser Gly Ser Arg Leu Ala Ala Gln Gln Gln Met Glu Gly Leu Leu
    1280                1285                1290

Ala Pro His Arg Pro Lys Glu Pro Ala Trp Phe Leu Ala Thr Val
    1295                1300                1305

Gly Val Ser Pro Asp His Gln Gly Lys Gly Leu Gly Ser Ala Val
    1310                1315                1320

Val Leu Pro Gly Val Glu Ala Ala Glu Arg Ala Gly Val Pro Ala
```

<210> SEQ ID NO 41
<211> LENGTH: 4140
<212> TYPE: DNA
<213> ORGANISM: Artificial Sequence
<220> FEATURE:
<223> OTHER INFORMATION: NLS-PF(v51)-dSaCas9(D10A,N580A)-NLS-KRAB-P2A-Puro fusion protein
<220> FEATURE:
<221> NAME/KEY: CDS
<222> LOCATION: (1)..(4140)

<400> SEQUENCE: 41

```
atg gcc cca aag aag aag cgg aag gtc ggt atc cac gga gtc cca gca      48
Met Ala Pro Lys Lys Lys Arg Lys Val Gly Ile His Gly Val Pro Ala
1               5                   10                  15 gcc aag cgg aac tac atc ctg ggc ctg gcc atc ggc atc acc agc gtg      96
Ala Lys Arg Asn Tyr Ile Leu Gly Leu Ala Ile Gly Ile Thr Ser Val
            20                  25                  30 ggc tac ggc atc atc gac tac gag aca cgg gac gtg atc gat gcc ggc     144
Gly Tyr Gly Ile Ile Asp Tyr Glu Thr Arg Asp Val Ile Asp Ala Gly
        35                  40                  45 gtg cgg ctg ttc aaa gag gcc aac gtg gaa aac aac gag ggc agg cgg     192
Val Arg Leu Phe Lys Glu Ala Asn Val Glu Asn Asn Glu Gly Arg Arg
    50                  55                  60 agc aag aga ggc gcc aga agg ctg aag cgg cgg agg cgg cat aga atc     240
Ser Lys Arg Gly Ala Arg Arg Leu Lys Arg Arg Arg Arg His Arg Ile
65                  70                  75                  80 cag aga gtg aag aag ctg ctg ttc gac tac aac ctg ctg acc gac cac     288
Gln Arg Val Lys Lys Leu Leu Phe Asp Tyr Asn Leu Leu Thr Asp His
                85                  90                  95 agc gag ctg agc ggc atc aac ccc tac gag gcc aga gtg aag ggc ctg     336
Ser Glu Leu Ser Gly Ile Asn Pro Tyr Glu Ala Arg Val Lys Gly Leu
            100                 105                 110 agc cag aag ctg agc gag gaa gag ttc tct gcc gcc ctg ctg cac ctg     384
Ser Gln Lys Leu Ser Glu Glu Glu Phe Ser Ala Ala Leu Leu His Leu
        115                 120                 125 gcc aag aga aga ggc gtg cac aac gtg aac gag gtg gaa gag gac acc     432
Ala Lys Arg Arg Gly Val His Asn Val Asn Glu Val Glu Glu Asp Thr
    130                 135                 140 ggc aac gag ctg tcc acc aaa gag cag atc agc cgg aac agc aag gcc     480
Gly Asn Glu Leu Ser Thr Lys Glu Gln Ile Ser Arg Asn Ser Lys Ala
145                 150                 155                 160 ctg gaa gag aaa tac gtg gcc gaa ctg cag ctg gaa cgg ctg aag aaa     528
Leu Glu Glu Lys Tyr Val Ala Glu Leu Gln Leu Glu Arg Leu Lys Lys
                165                 170                 175 gac ggc gaa gtg cgg ggc agc atc aac aga ttc aag acc agc gac tac     576
Asp Gly Glu Val Arg Gly Ser Ile Asn Arg Phe Lys Thr Ser Asp Tyr
            180                 185                 190 gtg aaa gaa gcc aaa cag ctg ctg aag gtg cag aag gcc tac cac cag     624
Val Lys Glu Ala Lys Gln Leu Leu Lys Val Gln Lys Ala Tyr His Gln
        195                 200                 205 ctg gac cag agc ttc atc gac acc tac atc gac ctg ctg gaa acc cgg     672
Leu Asp Gln Ser Phe Ile Asp Thr Tyr Ile Asp Leu Leu Glu Thr Arg
```

```
                210                 215                 220
cgg acc tac tat gag gga cct ggc gag ggc agc ccc ttc ggc tgg aag      720
Arg Thr Tyr Tyr Glu Gly Pro Gly Glu Gly Ser Pro Phe Gly Trp Lys
225                 230                 235                 240 gac atc aaa gaa tgg tac gag atg ctg atg ggc cac tgc acc tac ttc      768
Asp Ile Lys Glu Trp Tyr Glu Met Leu Met Gly His Cys Thr Tyr Phe
                    245                 250                 255 ccc gag gaa ctg cgg agc gtg aag tac gcc tac aac gcc gac ctg tac      816
Pro Glu Glu Leu Arg Ser Val Lys Tyr Ala Tyr Asn Ala Asp Leu Tyr
            260                 265                 270 aac gcc ctg aac gac ctg aac aat ctc gtg atc acc agg gac gag aac      864
Asn Ala Leu Asn Asp Leu Asn Asn Leu Val Ile Thr Arg Asp Glu Asn
        275                 280                 285 gag aag ctg gaa tat tac gag aag ttc cag atc atc gag aac gtg ttc      912
Glu Lys Leu Glu Tyr Tyr Glu Lys Phe Gln Ile Ile Glu Asn Val Phe
290                 295                 300 aag cag aag aag aag ccc acc ctg aag cag atc gcc aaa gaa atc ctc      960
Lys Gln Lys Lys Lys Pro Thr Leu Lys Gln Ile Ala Lys Glu Ile Leu
305                 310                 315                 320 gtg aac gaa gag gat att aag ggc tac aga gtg acc agc acc ggc aag     1008
Val Asn Glu Glu Asp Ile Lys Gly Tyr Arg Val Thr Ser Thr Gly Lys
                    325                 330                 335 ccc gag ttc acc aac ctg aag gtg tac cac gac atc aag gac att acc     1056
Pro Glu Phe Thr Asn Leu Lys Val Tyr His Asp Ile Lys Asp Ile Thr
            340                 345                 350 gcc cgg aaa gag att att gag aac gcc gag ctg ctg gat cag att gcc     1104
Ala Arg Lys Glu Ile Ile Glu Asn Ala Glu Leu Leu Asp Gln Ile Ala
        355                 360                 365 aag atc ctg acc atc tac cag agc agc gag gac atc cag gaa gaa ctg     1152
Lys Ile Leu Thr Ile Tyr Gln Ser Ser Glu Asp Ile Gln Glu Glu Leu
370                 375                 380 acc aat ctg aac tcc gag ctg acc cag gaa gag atc gag cag atc tct     1200
Thr Asn Leu Asn Ser Glu Leu Thr Gln Glu Glu Ile Glu Gln Ile Ser
385                 390                 395                 400 aat ctg aag ggc tat acc ggc acc cac aac ctg agc ctg aag gcc atc     1248
Asn Leu Lys Gly Tyr Thr Gly Thr His Asn Leu Ser Leu Lys Ala Ile
                    405                 410                 415 aac ctg atc ctg gac gag ctg tgg cac acc aac gac aac cag atc gct     1296
Asn Leu Ile Leu Asp Glu Leu Trp His Thr Asn Asp Asn Gln Ile Ala
            420                 425                 430 atc ttc aac cgg ctg aag ctg gtg ccc aag aag gtg gac ctg tcc cag     1344
Ile Phe Asn Arg Leu Lys Leu Val Pro Lys Lys Val Asp Leu Ser Gln
        435                 440                 445 cag aaa gag atc ccc acc acc ctg gtg gac gac ttc atc ctg agc ccc     1392
Gln Lys Glu Ile Pro Thr Thr Leu Val Asp Asp Phe Ile Leu Ser Pro
450                 455                 460 gtc gtg aag aga agc ttc atc cag agc atc aaa gtg atc aac gcc atc     1440
Val Val Lys Arg Ser Phe Ile Gln Ser Ile Lys Val Ile Asn Ala Ile
465                 470                 475                 480 atc aag aag tac ggc ctg ccc aac gac atc att atc gag ctg gcc cgc     1488
Ile Lys Lys Tyr Gly Leu Pro Asn Asp Ile Ile Ile Glu Leu Ala Arg
                    485                 490                 495 gag aag aac tcc aag gac gcc cag aaa atg atc aac gag atg cag aag     1536
Glu Lys Asn Ser Lys Asp Ala Gln Lys Met Ile Asn Glu Met Gln Lys
            500                 505                 510 cgg aac cgg cag acc aac gag cgg atc gag gaa atc atc cgg acc acc     1584
Arg Asn Arg Gln Thr Asn Glu Arg Ile Glu Glu Ile Ile Arg Thr Thr
        515                 520                 525 ggc aaa gag aac gcc aag tac ctg atc gag aag atc aag ctg cac gac     1632
```

```
Gly Lys Glu Asn Ala Lys Tyr Leu Ile Glu Lys Ile Lys Leu His Asp
    530                 535                 540 atg cag gaa ggc aag tgc ctg tac agc ctg gaa gcc atc cct ctg gaa       1680
Met Gln Glu Gly Lys Cys Leu Tyr Ser Leu Glu Ala Ile Pro Leu Glu
545                 550                 555                 560 gat ctg ctg aac aac ccc ttc aac tat gag gtg gac cac atc atc ccc       1728
Asp Leu Leu Asn Asn Pro Phe Asn Tyr Glu Val Asp His Ile Ile Pro
                565                 570                 575 aga agc gtg tcc ttc gac aac agc ttc aac aac aag gtg ctc gtg aag       1776
Arg Ser Val Ser Phe Asp Asn Ser Phe Asn Asn Lys Val Leu Val Lys
            580                 585                 590 cag gaa gaa gcc agc aag aag ggc aac cgg acc cca ttc cag tac ctg       1824
Gln Glu Glu Ala Ser Lys Lys Gly Asn Arg Thr Pro Phe Gln Tyr Leu
        595                 600                 605 agc agc agc gac agc aag atc agc tac gaa acc ttc aag aag cac atc       1872
Ser Ser Ser Asp Ser Lys Ile Ser Tyr Glu Thr Phe Lys Lys His Ile
    610                 615                 620 ctg aat ctg gcc aag ggc aag ggc aga atc agc aag acc aag aaa gag       1920
Leu Asn Leu Ala Lys Gly Lys Gly Arg Ile Ser Lys Thr Lys Lys Glu
625                 630                 635                 640 tat ctg ctg gaa gaa cgg gac atc aac agg ttc tcc gtg cag aaa gac       1968
Tyr Leu Leu Glu Glu Arg Asp Ile Asn Arg Phe Ser Val Gln Lys Asp
                645                 650                 655 ttc atc aac cgg aac ctg gtg gat acc aga tac gcc acc aga ggc ctg       2016
Phe Ile Asn Arg Asn Leu Val Asp Thr Arg Tyr Ala Thr Arg Gly Leu
            660                 665                 670 atg aac ctg ctg cgg agc tac ttc aga gtg aac aac ctg gac gtg aaa       2064
Met Asn Leu Leu Arg Ser Tyr Phe Arg Val Asn Asn Leu Asp Val Lys
        675                 680                 685 gtg aag tcc atc aat ggc ggc ttc acc agc ttt ctg cgg cgg aag tgg       2112
Val Lys Ser Ile Asn Gly Gly Phe Thr Ser Phe Leu Arg Arg Lys Trp
    690                 695                 700 aag ttt aag aaa gag cgg aac aag ggg tac aag cac cac gcc gag gac       2160
Lys Phe Lys Lys Glu Arg Asn Lys Gly Tyr Lys His His Ala Glu Asp
705                 710                 715                 720 gcc ctg atc att gcc aac gcc gat ttc atc ttc aaa gag tgg aag aaa       2208
Ala Leu Ile Ile Ala Asn Ala Asp Phe Ile Phe Lys Glu Trp Lys Lys
                725                 730                 735 ctg gac aag gcc aaa aaa gtg atg gaa aac cag atg ttc gag gaa aag       2256
Leu Asp Lys Ala Lys Lys Val Met Glu Asn Gln Met Phe Glu Glu Lys
            740                 745                 750 cag gcc gag agc atg ccc gag atc gaa acc gag cag gag tac aaa gag       2304
Gln Ala Glu Ser Met Pro Glu Ile Glu Thr Glu Gln Glu Tyr Lys Glu
        755                 760                 765 atc ttc atc acc ccc cac cag atc aag cac att aag gac ttc aag gac       2352
Ile Phe Ile Thr Pro His Gln Ile Lys His Ile Lys Asp Phe Lys Asp
    770                 775                 780 tac aag tac agc cac cgg gtg gac aag aag cct aat aga aaa ctg att       2400
Tyr Lys Tyr Ser His Arg Val Asp Lys Lys Pro Asn Arg Lys Leu Ile
785                 790                 795                 800 aac gac acc ctg tac tcc acc cgg aag gac gac aag ggc aac acc cgg       2448
Asn Asp Thr Leu Tyr Ser Thr Arg Lys Asp Asp Lys Gly Asn Thr Arg
                805                 810                 815 atc gtg aac aat ctg aac ggc ctg tac gac aag gac aat gac aag ctg       2496
Ile Val Asn Asn Leu Asn Gly Leu Tyr Asp Lys Asp Asn Asp Lys Leu
            820                 825                 830 aaa aag ctg atc aac aag agc ccc gaa aag ctg ctg atg tac cac cac       2544
Lys Lys Leu Ile Asn Lys Ser Pro Glu Lys Leu Leu Met Tyr His His
        835                 840                 845
```

```
gac ccc cag acc tac cag aaa ctg aag ctg att atg gaa cag tac ggc       2592
Asp Pro Gln Thr Tyr Gln Lys Leu Lys Leu Ile Met Glu Gln Tyr Gly
        850                 855                 860 gac gag aag aat ccc ctg tac aag tac tac gag gaa acc ggg aac tac       2640
Asp Glu Lys Asn Pro Leu Tyr Lys Tyr Tyr Glu Glu Thr Gly Asn Tyr
865                 870                 875                 880 ctg acc aag tac tcc aaa aag gac aac ggc ccc gtg atc aag aag att       2688
Leu Thr Lys Tyr Ser Lys Lys Asp Asn Gly Pro Val Ile Lys Lys Ile
            885                 890                 895 aag tat tac ggc aac aaa ctg aac gcc cat ctg gac atc acc gac gac       2736
Lys Tyr Tyr Gly Asn Lys Leu Asn Ala His Leu Asp Ile Thr Asp Asp
                900                 905                 910 tac ccc aac agc aga aac aag gtc gtg aag ctg tcc ctg aag ccc tac       2784
Tyr Pro Asn Ser Arg Asn Lys Val Val Lys Leu Ser Leu Lys Pro Tyr
                    915                 920                 925 aga ttc gac gtg tac ctg gac aat ggc gtg tac aag ttc gtg aag gtg       2832
Arg Phe Asp Val Tyr Leu Asp Asn Gly Val Tyr Lys Phe Val Lys Val
        930                 935                 940 aat aat ctg gat gtg atc aaa aaa gaa aac tac tac gaa gtg aat agc       2880
Asn Asn Leu Asp Val Ile Lys Lys Glu Asn Tyr Tyr Glu Val Asn Ser
945                 950                 955                 960 aag tgc tat gag gaa gct aag aag ctg aag aag atc agc aac cag gcc       2928
Lys Cys Tyr Glu Glu Ala Lys Lys Leu Lys Lys Ile Ser Asn Gln Ala
            965                 970                 975 gag ttt atc gcc tcc ttc tac aga aac gat ctg atc aag atc aac ggc       2976
Glu Phe Ile Ala Ser Phe Tyr Arg Asn Asp Leu Ile Lys Ile Asn Gly
                980                 985                 990 gag ctg tat aga gtg atc ggc gtg  gcc aac gac ctg ctg  aac gcc atc     3024
Glu Leu Tyr Arg Val Ile Gly Val  Ala Asn Asp Leu Leu  Asn Ala Ile
                995                 1000                1005 gaa gtg  aac atg atc gac atc  acc tac cgc gag tac  ctg gaa aac        3069
Glu Val  Asn Met Ile Asp Ile  Thr Tyr Arg Glu Tyr  Leu Glu Asn
    1010                1015                1020 atg aac gac aag agg ccc ccc  agg atc ttc aag aca  atc tcc tcc         3114
Met Asn Asp Lys Arg Pro Pro  Arg Ile Phe Lys Thr  Ile Ser Ser
1025                1030                1035 aag acc cag agc att aag aag  tac agc aca gac att  ctg ggc aac         3159
Lys Thr Gln Ser Ile Lys Lys  Tyr Ser Thr Asp Ile  Leu Gly Asn
    1040                1045                1050 ctg tat  gaa gtg aaa tct aag  aag cac cct cag atc  atc aaa aag        3204
Leu Tyr  Glu Val Lys Ser Lys  Lys His Pro Gln Ile  Ile Lys Lys
    1055                1060                1065 ggc aaa  agg ccg gcg gcc acg  aaa aag gcc ggc cag  gca aaa aag        3249
Gly Lys  Arg Pro Ala Ala Thr  Lys Lys Ala Gly Gln  Ala Lys Lys
    1070                1075                1080 aaa aag  gga tcc atg gat gct  aag tca cta act gcc  tgg tcc cgg        3294
Lys Lys  Gly Ser Met Asp Ala  Lys Ser Leu Thr Ala  Trp Ser Arg
    1085                1090                1095 aca ctg  gtg acc ttc aag gat  gta ttt gtg gac ttc  acc agg gag        3339
Thr Leu  Val Thr Phe Lys Asp  Val Phe Val Asp Phe  Thr Arg Glu
    1100                1105                1110 gag tgg  aag ctg ctg gac act  gct cag cag atc gtg  tac aga aat        3384
Glu Trp  Lys Leu Leu Asp Thr  Ala Gln Gln Ile Val  Tyr Arg Asn
    1115                1120                1125 gtg atg  ctg gag aac tat aag  aac ctg gtt tcc ttg  ggt tat cag        3429
Val Met  Leu Glu Asn Tyr Lys  Asn Leu Val Ser Leu  Gly Tyr Gln
    1130                1135                1140 ctt act  aag cca gat gtg atc  ctc cgg ttg gag aag  gga gaa gag        3474
Leu Thr  Lys Pro Asp Val Ile  Leu Arg Leu Glu Lys  Gly Glu Glu
    1145                1150                1155
```

```
ccc  gga  agc  ggt  gct  act  aac  ttc  agc  ctg  ctg  aag  cag  gct  gga       3519
Pro  Gly  Ser  Gly  Ala  Thr  Asn  Phe  Ser  Leu  Leu  Lys  Gln  Ala  Gly
     1160                1165                1170 gac  gtg  gag  gag  aac  cct  gga  cct  acc  gag  tac  aag  ccc  acg  gtg       3564
Asp  Val  Glu  Glu  Asn  Pro  Gly  Pro  Thr  Glu  Tyr  Lys  Pro  Thr  Val
     1175                1180                1185 cgc  ctc  gcc  acc  cgc  gac  gac  gtc  ccc  agg  gcc  gta  cgc  acc  ctc       3609
Arg  Leu  Ala  Thr  Arg  Asp  Asp  Val  Pro  Arg  Ala  Val  Arg  Thr  Leu
     1190                1195                1200 gcc  gcc  gcg  ttc  gcc  gac  tac  ccc  gcc  acg  cgc  cac  acc  gtc  gat       3654
Ala  Ala  Ala  Phe  Ala  Asp  Tyr  Pro  Ala  Thr  Arg  His  Thr  Val  Asp
     1205                1210                1215 ccg  gac  cgc  cac  atc  gag  cgg  gtc  acc  gag  ctg  caa  gaa  ctc  ttc       3699
Pro  Asp  Arg  His  Ile  Glu  Arg  Val  Thr  Glu  Leu  Gln  Glu  Leu  Phe
     1220                1225                1230 ctc  acg  cgc  gtc  ggg  ctc  gac  atc  ggc  aag  gtg  tgg  gtc  gcg  gac       3744
Leu  Thr  Arg  Val  Gly  Leu  Asp  Ile  Gly  Lys  Val  Trp  Val  Ala  Asp
     1235                1240                1245 gac  ggc  gcc  gcg  gtg  gcg  gtc  tgg  acc  acg  ccg  gag  agc  gtc  gaa       3789
Asp  Gly  Ala  Ala  Val  Ala  Val  Trp  Thr  Thr  Pro  Glu  Ser  Val  Glu
     1250                1255                1260 gcg  ggg  gcg  gtg  ttc  gcc  gag  atc  ggc  ccg  cgc  atg  gcc  gag  ttg       3834
Ala  Gly  Ala  Val  Phe  Ala  Glu  Ile  Gly  Pro  Arg  Met  Ala  Glu  Leu
     1265                1270                1275 agc  ggt  tcc  cgg  ctg  gcc  gcg  cag  caa  cag  atg  gaa  ggc  ctc  ctg       3879
Ser  Gly  Ser  Arg  Leu  Ala  Ala  Gln  Gln  Gln  Met  Glu  Gly  Leu  Leu
     1280                1285                1290 gcg  ccg  cac  cgg  ccc  aag  gag  ccc  gcg  tgg  ttc  ctg  gcc  acc  gtc       3924
Ala  Pro  His  Arg  Pro  Lys  Glu  Pro  Ala  Trp  Phe  Leu  Ala  Thr  Val
     1295                1300                1305 gga  gtc  tcg  ccc  gac  cac  cag  ggc  aag  ggt  ctg  ggc  agc  gcc  gtc       3969
Gly  Val  Ser  Pro  Asp  His  Gln  Gly  Lys  Gly  Leu  Gly  Ser  Ala  Val
     1310                1315                1320 gtg  ctc  ccc  gga  gtg  gag  gcg  gcc  gag  cgc  gcc  ggg  gtg  ccc  gcc       4014
Val  Leu  Pro  Gly  Val  Glu  Ala  Ala  Glu  Arg  Ala  Gly  Val  Pro  Ala
     1325                1330                1335 ttc  ctg  gaa  acc  tcc  gcg  ccc  cgc  aac  ctc  ccc  ttc  tac  gag  cgg       4059
Phe  Leu  Glu  Thr  Ser  Ala  Pro  Arg  Asn  Leu  Pro  Phe  Tyr  Glu  Arg
     1340                1345                1350 ctc  ggc  ttc  acc  gtc  acc  gcc  gac  gtc  gag  gtg  ccc  gaa  gga  ccg       4104
Leu  Gly  Phe  Thr  Val  Thr  Ala  Asp  Val  Glu  Val  Pro  Glu  Gly  Pro
     1355                1360                1365 cgc  acc  tgg  tgc  atg  acc  cgc  aag  ccc  ggt  gcc  tga                      4140
Arg  Thr  Trp  Cys  Met  Thr  Arg  Lys  Pro  Gly  Ala
     1370                1375

<210> SEQ ID NO 42
<211> LENGTH: 1379
<212> TYPE: PRT
<213> ORGANISM: Artificial Sequence
<220> FEATURE:
<223> OTHER INFORMATION: Synthetic Construct

<400> SEQUENCE: 42

Met  Ala  Pro  Lys  Lys  Arg  Lys  Val  Gly  Ile  His  Gly  Val  Pro  Ala
1                  5                   10                  15

Ala  Lys  Arg  Asn  Tyr  Ile  Leu  Gly  Leu  Ala  Ile  Gly  Ile  Thr  Ser  Val
                20                  25                  30

Gly  Tyr  Gly  Ile  Ile  Asp  Tyr  Glu  Thr  Arg  Asp  Val  Ile  Asp  Ala  Gly
        35                  40                  45
```

-continued

```
Val Arg Leu Phe Lys Glu Ala Asn Val Glu Asn Asn Glu Gly Arg Arg
     50                  55                  60

Ser Lys Arg Gly Ala Arg Arg Leu Lys Arg Arg Arg His Arg Ile
 65              70                  75                  80

Gln Arg Val Lys Lys Leu Leu Phe Asp Tyr Asn Leu Leu Thr Asp His
                 85                  90                  95

Ser Glu Leu Ser Gly Ile Asn Pro Tyr Glu Ala Arg Val Lys Gly Leu
                100                 105                 110

Ser Gln Lys Leu Ser Glu Glu Phe Ser Ala Ala Leu Leu His Leu
            115                 120                 125

Ala Lys Arg Arg Gly Val His Asn Val Asn Glu Val Glu Glu Asp Thr
    130                 135                 140

Gly Asn Glu Leu Ser Thr Lys Glu Gln Ile Ser Arg Asn Ser Lys Ala
145                 150                 155                 160

Leu Glu Glu Lys Tyr Val Ala Glu Leu Gln Leu Glu Arg Leu Lys Lys
                165                 170                 175

Asp Gly Glu Val Arg Gly Ser Ile Asn Arg Phe Lys Thr Ser Asp Tyr
                180                 185                 190

Val Lys Glu Ala Lys Gln Leu Leu Lys Val Gln Lys Ala Tyr His Gln
                195                 200                 205

Leu Asp Gln Ser Phe Ile Asp Thr Tyr Ile Asp Leu Leu Glu Thr Arg
    210                 215                 220

Arg Thr Tyr Tyr Glu Gly Pro Gly Glu Gly Ser Pro Phe Gly Trp Lys
225                 230                 235                 240

Asp Ile Lys Glu Trp Tyr Glu Met Leu Met Gly His Cys Thr Tyr Phe
                245                 250                 255

Pro Glu Glu Leu Arg Ser Val Lys Tyr Ala Tyr Asn Ala Asp Leu Tyr
            260                 265                 270

Asn Ala Leu Asn Asp Leu Asn Asn Leu Val Ile Thr Arg Asp Glu Asn
    275                 280                 285

Glu Lys Leu Glu Tyr Tyr Glu Lys Phe Gln Ile Ile Glu Asn Val Phe
290                 295                 300

Lys Gln Lys Lys Lys Pro Thr Leu Lys Gln Ile Ala Lys Glu Ile Leu
305                 310                 315                 320

Val Asn Glu Glu Asp Ile Lys Gly Tyr Arg Val Thr Ser Thr Gly Lys
                325                 330                 335

Pro Glu Phe Thr Asn Leu Lys Val Tyr His Asp Ile Lys Asp Ile Thr
            340                 345                 350

Ala Arg Lys Glu Ile Ile Glu Asn Ala Glu Leu Leu Asp Gln Ile Ala
    355                 360                 365

Lys Ile Leu Thr Ile Tyr Gln Ser Ser Glu Asp Ile Gln Glu Glu Leu
370                 375                 380

Thr Asn Leu Asn Ser Glu Leu Thr Gln Glu Glu Ile Glu Gln Ile Ser
385                 390                 395                 400

Asn Leu Lys Gly Tyr Thr Gly Thr His Asn Leu Ser Leu Lys Ala Ile
                405                 410                 415

Asn Leu Ile Leu Asp Glu Leu Trp His Thr Asn Asp Asn Gln Ile Ala
            420                 425                 430

Ile Phe Asn Arg Leu Lys Leu Val Pro Lys Lys Val Asp Leu Ser Gln
    435                 440                 445

Gln Lys Glu Ile Pro Thr Thr Leu Val Asp Asp Phe Ile Leu Ser Pro
450                 455                 460
```

```
Val Val Lys Arg Ser Phe Ile Gln Ser Ile Lys Val Ile Asn Ala Ile
465                 470                 475                 480

Ile Lys Lys Tyr Gly Leu Pro Asn Asp Ile Ile Glu Leu Ala Arg
            485                 490                 495

Glu Lys Asn Ser Lys Asp Ala Gln Lys Met Ile Asn Glu Met Gln Lys
                500                 505                 510

Arg Asn Arg Gln Thr Asn Glu Arg Ile Glu Glu Ile Arg Thr Thr
            515                 520                 525

Gly Lys Glu Asn Ala Lys Tyr Leu Ile Glu Lys Ile Lys Leu His Asp
            530                 535                 540

Met Gln Glu Gly Lys Cys Leu Tyr Ser Leu Glu Ala Ile Pro Leu Glu
545                 550                 555                 560

Asp Leu Leu Asn Asn Pro Phe Asn Tyr Glu Val Asp His Ile Ile Pro
                565                 570                 575

Arg Ser Val Ser Phe Asp Asn Ser Phe Asn Asn Lys Val Leu Val Lys
            580                 585                 590

Gln Glu Glu Ala Ser Lys Lys Gly Asn Arg Thr Pro Phe Gln Tyr Leu
    595                 600                 605

Ser Ser Ser Asp Ser Lys Ile Ser Tyr Glu Thr Phe Lys Lys His Ile
610                 615                 620

Leu Asn Leu Ala Lys Gly Lys Gly Arg Ile Ser Lys Thr Lys Lys Glu
625                 630                 635                 640

Tyr Leu Leu Glu Glu Arg Asp Ile Asn Arg Phe Ser Val Gln Lys Asp
                645                 650                 655

Phe Ile Asn Arg Asn Leu Val Asp Thr Arg Tyr Ala Thr Arg Gly Leu
            660                 665                 670

Met Asn Leu Leu Arg Ser Tyr Phe Arg Val Asn Asn Leu Asp Val Lys
            675                 680                 685

Val Lys Ser Ile Asn Gly Gly Phe Thr Ser Phe Leu Arg Arg Lys Trp
    690                 695                 700

Lys Phe Lys Lys Glu Arg Asn Lys Gly Tyr Lys His His Ala Glu Asp
705                 710                 715                 720

Ala Leu Ile Ile Ala Asn Ala Asp Phe Ile Phe Lys Glu Trp Lys Lys
                725                 730                 735

Leu Asp Lys Ala Lys Lys Val Met Glu Asn Gln Met Phe Glu Glu Lys
            740                 745                 750

Gln Ala Glu Ser Met Pro Glu Ile Glu Thr Glu Gln Glu Tyr Lys Glu
            755                 760                 765

Ile Phe Ile Thr Pro His Gln Ile Lys His Ile Lys Asp Phe Lys Asp
    770                 775                 780

Tyr Lys Tyr Ser His Arg Val Asp Lys Lys Pro Asn Arg Lys Leu Ile
785                 790                 795                 800

Asn Asp Thr Leu Tyr Ser Thr Arg Lys Asp Asp Lys Gly Asn Thr Arg
            805                 810                 815

Ile Val Asn Asn Leu Asn Gly Leu Tyr Asp Lys Asp Asn Asp Lys Leu
            820                 825                 830

Lys Lys Leu Ile Asn Lys Ser Pro Glu Lys Leu Leu Met Tyr His His
            835                 840                 845

Asp Pro Gln Thr Tyr Gln Lys Leu Lys Leu Ile Met Glu Gln Tyr Gly
    850                 855                 860

Asp Glu Lys Asn Pro Leu Tyr Lys Tyr Glu Glu Thr Gly Asn Tyr
865                 870                 875                 880

Leu Thr Lys Tyr Ser Lys Lys Asp Asn Gly Pro Val Ile Lys Lys Ile
```

```
                    885                 890                 895
Lys Tyr Tyr Gly Asn Lys Leu Asn Ala His Leu Asp Ile Thr Asp Asp
                900                 905                 910
Tyr Pro Asn Ser Arg Asn Lys Val Val Lys Leu Ser Leu Lys Pro Tyr
                915                 920                 925
Arg Phe Asp Val Tyr Leu Asp Asn Gly Val Tyr Lys Phe Val Lys Val
    930                 935                 940
Asn Asn Leu Asp Val Ile Lys Lys Glu Asn Tyr Tyr Glu Val Asn Ser
945                 950                 955                 960
Lys Cys Tyr Glu Glu Ala Lys Lys Leu Lys Lys Ile Ser Asn Gln Ala
                965                 970                 975
Glu Phe Ile Ala Ser Phe Tyr Arg Asn Asp Leu Ile Lys Ile Asn Gly
                980                 985                 990
Glu Leu Tyr Arg Val Ile Gly Val Ala Asn Asp Leu Leu Asn Ala Ile
                995                1000                1005
Glu Val Asn Met Ile Asp Ile Thr Tyr Arg Glu Tyr Leu Glu Asn
                1010                1015                1020
Met Asn Asp Lys Arg Pro Pro Arg Ile Phe Lys Thr Ile Ser Ser
                1025                1030                1035
Lys Thr Gln Ser Ile Lys Lys Tyr Ser Thr Asp Ile Leu Gly Asn
                1040                1045                1050
Leu Tyr Glu Val Lys Ser Lys His Pro Gln Ile Ile Lys Lys
                1055                1060                1065
Gly Lys Arg Pro Ala Ala Thr Lys Lys Ala Gly Gln Ala Lys Lys
                1070                1075                1080
Lys Lys Gly Ser Met Asp Ala Lys Ser Leu Thr Ala Trp Ser Arg
                1085                1090                1095
Thr Leu Val Thr Phe Lys Asp Val Phe Val Asp Phe Thr Arg Glu
                1100                1105                1110
Glu Trp Lys Leu Leu Asp Thr Ala Gln Gln Ile Val Tyr Arg Asn
                1115                1120                1125
Val Met Leu Glu Asn Tyr Lys Asn Leu Val Ser Leu Gly Tyr Gln
                1130                1135                1140
Leu Thr Lys Pro Asp Val Ile Leu Arg Leu Glu Lys Gly Glu Glu
                1145                1150                1155
Pro Gly Ser Gly Ala Thr Asn Phe Ser Leu Leu Lys Gln Ala Gly
                1160                1165                1170
Asp Val Glu Glu Asn Pro Gly Pro Thr Glu Tyr Lys Pro Thr Val
                1175                1180                1185
Arg Leu Ala Thr Arg Asp Asp Val Pro Arg Ala Val Arg Thr Leu
                1190                1195                1200
Ala Ala Ala Phe Ala Asp Tyr Pro Ala Thr Arg His Thr Val Asp
                1205                1210                1215
Pro Asp Arg His Ile Glu Arg Val Thr Glu Leu Gln Glu Leu Phe
                1220                1225                1230
Leu Thr Arg Val Gly Leu Asp Ile Gly Lys Val Trp Val Ala Asp
                1235                1240                1245
Asp Gly Ala Ala Val Ala Val Trp Thr Thr Pro Glu Ser Val Glu
                1250                1255                1260
Ala Gly Ala Val Phe Ala Glu Ile Gly Pro Arg Met Ala Glu Leu
                1265                1270                1275
Ser Gly Ser Arg Leu Ala Ala Gln Gln Gln Met Glu Gly Leu Leu
                1280                1285                1290
```

-continued

```
Ala Pro His Arg Pro Lys Glu Pro Ala Trp Phe Leu Ala Thr Val
   1295                1300                1305

Gly Val Ser Pro Asp His Gln Gly Lys Gly Leu Gly Ser Ala Val
   1310                1315                1320

Val Leu Pro Gly Val Glu Ala Ala Glu Arg Ala Gly Val Pro Ala
   1325                1330                1335

Phe Leu Glu Thr Ser Ala Pro Arg Asn Leu Pro Phe Tyr Glu Arg
   1340                1345                1350

Leu Gly Phe Thr Val Thr Ala Asp Val Glu Val Pro Glu Gly Pro
   1355                1360                1365

Arg Thr Trp Cys Met Thr Arg Lys Pro Gly Ala
   1370                1375

<210> SEQ ID NO 43
<211> LENGTH: 21
<212> TYPE: DNA
<213> ORGANISM: Artificial Sequence
<220> FEATURE:
<223> OTHER INFORMATION: sgRNA sequence_sgRNA-KRAS#1(WT)

<400> SEQUENCE: 43
gggaaggctg gaccgaggca g                                          21

<210> SEQ ID NO 44
<211> LENGTH: 21
<212> TYPE: DNA
<213> ORGANISM: Artificial Sequence
<220> FEATURE:
<223> OTHER INFORMATION: sgRNA sequence_sgRNA-KRAS#2(WT)

<400> SEQUENCE: 44
cagtccgaaa tggcgggggc c                                          21

<210> SEQ ID NO 45
<211> LENGTH: 21
<212> TYPE: DNA
<213> ORGANISM: Artificial Sequence
<220> FEATURE:
<223> OTHER INFORMATION: sgRNA sequence_sgRNA-KRAS#3(WT)

<400> SEQUENCE: 45
aatcgagctc cgagcacacc g                                          21

<210> SEQ ID NO 46
<211> LENGTH: 21
<212> TYPE: DNA
<213> ORGANISM: Artificial Sequence
<220> FEATURE:
<223> OTHER INFORMATION: sgRNA sequence_sgRNA-KRAS#4(PF-v15)

<400> SEQUENCE: 46
gtgcgggaga gaggtacgga g                                          21

<210> SEQ ID NO 47
<211> LENGTH: 21
<212> TYPE: DNA
<213> ORGANISM: Artificial Sequence
<220> FEATURE:
<223> OTHER INFORMATION: sgRNA sequence_sgRNA-KRAS#5(PF-v15)

<400> SEQUENCE: 47
ggagcgagcg cggcgcaggc a                                          21
```

```
<210> SEQ ID NO 48
<211> LENGTH: 21
<212> TYPE: DNA
<213> ORGANISM: Artificial Sequence
<220> FEATURE:
<223> OTHER INFORMATION: sgRNA sequence_sgRNA-KRAS#6(PF-v15)

<400> SEQUENCE: 48
cggccgcggc ggcggaggca g                                        21

<210> SEQ ID NO 49
<211> LENGTH: 20
<212> TYPE: DNA
<213> ORGANISM: Artificial Sequence
<220> FEATURE:
<223> OTHER INFORMATION: sgRNA sequence_sgRNA-C1

<400> SEQUENCE: 49
acggaggcta agcgtcgcaa                                          20

<210> SEQ ID NO 50
<211> LENGTH: 20
<212> TYPE: DNA
<213> ORGANISM: Artificial Sequence
<220> FEATURE:
<223> OTHER INFORMATION: sgRNA sequence_sgRNA-C2

<400> SEQUENCE: 50
cgcttccgcg gcccgttcaa                                          20

<210> SEQ ID NO 51
<211> LENGTH: 20
<212> TYPE: DNA
<213> ORGANISM: Artificial Sequence
<220> FEATURE:
<223> OTHER INFORMATION: sgRNA sequence_sgRNA-C3

<400> SEQUENCE: 51
gtaggcgcgc cgctctctac                                          20

<210> SEQ ID NO 52
<211> LENGTH: 28
<212> TYPE: DNA
<213> ORGANISM: Artificial Sequence
<220> FEATURE:
<223> OTHER INFORMATION: Stuffer sequence

<400> SEQUENCE: 52
gaaacaccgg agaccacggc aggtctca                                 28
```

MODIFIED CAS9 PROTEIN, AND USE THEREOF

SEQUENCE LISTING

The instant application contains a Sequence Listing which has been submitted in ASCII format via EFS-Web and is hereby incorporated by reference in its entirety. Said ASCII copy, created on Jan. 29, 2021 is named 529105USSeqListingtxt.txt and is 134918 KB in size

TECHNICAL FIELD

The present invention relates to a modified Cas9 protein with an expanded targetable region, and use thereof.

BACKGROUND ART

Clustered Regularly Interspaced Short Palindromic Repeats (CRISPR) are known to compose the adaptive immune system that provides acquired resistance against invasive foreign nucleic acids in bacteria and archaea together with Cas (CRISPR-associated) genes. CRISPR frequently originate from phage or plasmid DNA and are composed of 24 bp to 48 bp short, conserved repeat sequences having unique variable DNA sequences referred to as spacers of similar size inserted there between. In addition, a group of genes encoding the Cas protein family is present in the vicinity of the repeat and spacer sequences.

In the CRISPR-Cas system, foreign DNA is cleaved into fragments of about 30 bp by the Cas protein family and inserted into CRISPR. Cas1 and Cas2 proteins, which are among the Cas protein family, recognize a base sequence referred to as proto-spacer adjacent motif (PAM) of foreign DNA, cut the upstream, and insert same into the CRISPR sequence of the host, which creates immune memory of bacteria. RNA generated by transcription of a CRISPR sequence including immune memory (referred to as pre-crRNA) is paired with a partially complementary RNA (trans-activating crRNA: tracrRNA) and incorporated into Cas9 protein which is one of the Cas protein family. The pre-crRNA and tracrRNA incorporated into Cas9 are cleaved by RNaseIII to form small RNA fragments (CRISPR-RNAs: crRNAs) containing a foreign sequence (guide sequence), and a Cas9-crRNA-tracrRNA complex is thus formed. The Cas9-crRNA-tracrRNA complex binds to a foreign invasive DNA complementary to crRNA, and the Cas9 protein, which is an enzyme that cleaves the DNA (nuclease), cleaves the foreign invasive DNA, thereby suppressing and eliminating the function of the DNA that invaded from the outside.

Cas9 protein recognizes the PAM sequence in the foreign invasive DNA, and cleaves the double-stranded DNA at the upstream thereof to give a blunt end. The length and base sequence of the PAM sequence vary depending on the bacterial species, and *Streptococcus pyogenes* (*S. pyogenes*) recognizes 3 bases of "NGG" (N=A/C/T/G). *Streptococcus thermophilus* (*S. thermophilus*) has two Cas9 and they respectively recognize 5-6 bases in the form of "NGGNG" (N=A/C/T/G) or "NNAGAA" (N=A/C/T/G) as PAM sequences. *Francisella novicida* (*F. novicida*) recognizes three bases of "NGR" (N=A/C/T/G; R=A/G). *Staphylococcus aureus* (*S. aureus*) recognizes six bases of "NNGRRT" (N=A/C/T/G; R=A/G).

In recent years, techniques for applying the CRISPR-Cas system in bacteria to genome editing have been actively developed. crRNA and tracrRNA are fused, expressed as a tracrRNA-crRNA chimera (hereinafter to be referred to as guide RNA: gRNA), and utilized. Using this, nuclease (RNA-guided nuclease: RGN) is then recruited to cleave genomic DNA at the target site.

A method using the CRISPR-Cas system only needs to synthesize a short gRNA homologous to the target DNA sequence, and can perform genome editing using the Cas9 protein which is a single protein. Therefore, it is not necessary to synthesize large proteins that differ for each DNA sequence in the manner of conventionally used zinc finger nuclease (ZFN) or transcription activator-like effector nuclease (TALEN), and genome editing can be performed easily and quickly.

Patent Document 1 discloses a genome editing technique that uses a CRISPR-Cas system derived from *S. pyogenes*.

Patent Document 2 discloses a genome editing technique that uses a CRISPR-Cas system derived from *S. thermophilus*. Moreover, Patent document 2 discloses that a Cas9 protein mutant D31A or N891A functions as a DNA cleavage enzyme, nickase, that places a nick only in one of the DNA strands. Moreover, these mutants are also indicated as having homologous recombination efficiency comparable to that of wild-type Cas9 protein while retaining a low incidence of non-homologous end-joining susceptible to the occurrence of mutations such as insertions, deletions and the like in the repair mechanism following DNA cleavage.

Non-Patent Document 1 discloses a CRISPR-Cas system that uses *S. pyogenes*-derived Cas9, wherein the CRISPR-Cas system is a double nickase system that uses two Cas9 protein D10A mutants and a pair of target-specific guide RNA that form a complex with these D10A mutants. Each complex of Cas9 protein D10A mutant and target-specific guide RNA creates only one nick in DNA strand homologous to the guide DNA. The pair of guide RNA has about 20 bases of mismatch and only recognizes a target sequence located in the opposite strand of the target DNA. The two nicks created by each complex of Cas9 protein D10A mutant and target-specific guide RNA mimic a DNA double-strand break (DSB), and the use of the pair of guide RNA is indicated as being able to improve the specificity of Cas 9 protein-mediated genome editing while maintaining a high level of efficiency.

Patent document 3 discloses various mutants of Cas9 protein derived from *S. pyogenes* and Patent Document 4 discloses various mutants of Cas9 protein derived from *F. novicida*.

At present, SpCas9 is widely utilized as a genome editing tool. However, problems remain such as high molecular weight and low efficiency of introduction into viral vectors and the like. To solve the problems, compact Cas9 (SaCas9) derived from *Staphylococcus aureus* has been developed (non-patent document 2), and structure analysis has been performed (non-patent document 3, patent document 5). SaCas9 (1053 residues) has a smaller molecular weight compared to SpCas9 (1368 residues), and has low sequence identity (17%). SpCas9 recognizes 5'-NGG-3' as PAM, and SaCas9 recognizes 5'-NNGRRT-3' (R is a purine base, A or G).

DOCUMENT LIST

Patent Documents patent document 1: WO 2014/093661
patent document 2: National Publication of International Patent Application No. 2015-510778
patent document 3: WO 2016/141224 patent document 4: WO 2017/010543
patent document 5: WO 2016/205759

Non-Patent Document non-patent document 1: Ran, F. A., et al., Double Nicking by RNA-Guided CRISPR Cas9 for Enhanced Genome Editing Specificity. Cell, vol. 154, p1390-1389, 2013.
non-patent document 2: Ran, F. A., et al., In vivo genome editing using *Staphylococcus aureus* Cas9. Nature vol. 520, p186-191, 2015
non-patent document 3: Nishimasu H, et al., Crystal Structure of *Staphylococcus aureus* Cas9. Cell. Vol. 162, No. 5, p1113-1126, 2015

SUMMARY OF THE INVENTION

Problems to be Solved by the Invention

The PAM sequence able to be recognized by the *S. aureus*-derived Cas9 (to be also referred to as SaCas9 in the present specification) protein consists of 6 bases of "NNGRRT (N is any base and R is a purine residue (A or G))".

While SaCas9 is advantageous in that it is small as compared with conventional Cas9 proteins, since there are limitations on the PAM sequences that SaCas9 can recognize, there is also a problem of limitation on the editable target sequences.

The present invention aims to provide a modified SaCas9 protein with relaxed restriction on target sequence while maintaining binding ability to guide RNA, and use thereof.

Means of Solving the Problems

The present inventors have taken note of SaCas9 protein as Cas9 protein, and conducted intensive studies in an attempt to solve the above-mentioned problems. As a result, they have succeeded in converting a PAM sequence conventionally consisting of NNGRRT to a sequence of NNGNNN while maintaining the binding ability to guide RNA, by substituting an amino acid at a predetermined position of the SaCas9 protein with a specific amino acid (introducing a mutation), which resulted in the completion of the present invention.

In the present specification, Cas9 protein before introduction of mutation is sometimes to be referred to as wild-type Cas9 protein, and Cas9 protein after introduction of mutation is sometimes to be referred to as modified Cas9 protein or mutant Cas9 protein.

That is, the present invention provides the following.
[1] A protein consisting of an amino acid sequence resulting from mutations of the 985-position and the 991-position, and optionally the 986-position, and at least one site selected from the group consisting of the 782-position, the 800-position, the 888-position, the 968-position, the 988-position, the 1017-position and the 1021-position of the amino acid sequence shown in SEQ ID NO: 2, and having a binding ability to guide RNA.
[2] The protein of the above-mentioned [1], wherein the protein comprises mutation at at least 2 sites selected from the group consisting of the 782-position, the 800-position, the 888-position, the 968-position, the 988-position, the 1017-position and the 1021-position.
[3] The protein of the above-mentioned [1], wherein the protein comprises mutation at at least 3 sites selected from the group consisting of the 782-position, the 800-position, the 888-position, the 968-position, the 988-position, the 1017-position and the 1021-position.
[4] The protein of the above-mentioned [1], wherein the protein comprises mutation at at least 4 sites selected from the group consisting of the 782-position, the 800-position, the 888-position, the 968-position, the 988-position, the 1017-position and the 1021-position.
[5] The protein of the above-mentioned [1], wherein the protein comprises mutation at at least 5 sites selected from the group consisting of the 782-position, the 800-position, the 888-position, the 968-position, the 988-position, the 1017-position and the 1021-position.
[6] The protein of the above-mentioned [1], wherein the protein comprises mutation at at least 6 sites selected from the group consisting of the 782-position, the 800-position, the 888-position, the 968-position, the 988-position, the 1017-position and the 1021-position.
[7] The protein of any of the above-mentioned [1] to [6], wherein the mutation at the 782-position is substitution with lysine or arginine;
the mutation at the 800-position is substitution with arginine or lysine;
the mutation at the 888-position is substitution with an amino acid selected from the group consisting of lysine, arginine, asparagine, glutamine, histidine and serine;
the mutation at the 968-position is substitution with arginine or lysine;
the mutation at the 985-position is substitution with an amino acid selected from the group consisting of alanine, serine, threonine, cysteine, valine and isoleucine;
the mutation at the 986-position is substitution with an amino acid selected from the group consisting of alanine, serine, threonine, cysteine, valine and isoleucine;
the mutation at the 988-position is substitution with histidine;
the mutation at the 991-position is substitution with a non-aromatic amino acid;
the mutation at the 1017-position is substitution with an amino acid selected from the group consisting of phenylalanine, methionine, tyrosine, tryptophan and proline; and
the mutation at the 1021-position is substitution with an amino acid selected from the group consisting of serine, threonine and asparagine.
[8] The protein of any of the above-mentioned [1] to [7], wherein the mutation at the 782-position is substitution with lysine;
the mutation at the 800-position is substitution with arginine;
the mutation at the 888-position is substitution with lysine;
the mutation at the 968-position is substitution with arginine;
the mutation at the 985-position is substitution with alanine;
the mutation at the 986-position is substitution with alanine;
the mutation at the 991-position is substitution with alanine;
the mutation at the 988-position is substitution with histidine;
the mutation at the 1017-position is substitution with phenylalanine; and
the mutation at the 1021-position is substitution with serine.

[9] The protein of any of the above-mentioned [1] to [8], further comprising
(i) mutation at the 927-position and the 929-position,
(ii) mutation at the 929-position,
(iii) mutation at the 927-position,
(iv) mutation at the 889-position, or
(v) mutation at the 927-position, the 929-position and the 889-position.

[10] The protein of the above-mentioned [9], wherein
the mutation of (i) is substitution of the 927-position with lysine or arginine, and substitution of the 929-position with asparagine, aspartic acid or alanine;
the mutation of (ii) is substitution of the 929-position with arginine;
the mutation of (iii) is substitution of the 927-position with lysine or arginine;
the mutation of (iv) is substitution of the 889-position with asparagine, serine, lysine, arginine or histidine; and
the mutation of (v) is substitution of the 927-position with lysine or arginine, substitution of the 929-position with asparagine, aspartic acid or alanine, and substitution of the 889-position with asparagine.

[11] The protein of the above-mentioned [9], wherein
the mutation of (i) is substitution of the 927-position with lysine, and substitution of the 929-position with asparagine;
the mutation of (ii) is substitution of the 929-position with arginine;
the mutation of (iii) is substitution of the 927-position with lysine;
the mutation of (iv) is substitution of the 889-position with asparagine; and
the mutation of (v) is substitution of the 927-position with lysine, substitution of the 929-position with asparagine, and substitution of the 889-position with asparagine.

[12] The protein of the above-mentioned [9] consisting of a sequence comprising an amino acid sequence resulting from substitutions of
glutamic acid at the 782-position with lysine,
leucine at the 800-position with arginine;
asparagine at the 968-position with arginine;
asparagine at the 985-position with alanine;
asparagine at the 986-position with alanine;
arginine at the 991-position with alanine;
leucine at the 988-position with histidine;
alanine at the 1021-position with serine;
threonine at the 927-position with lysine;
lysine at the 929-position with asparagine; in the amino acid sequence shown in SEQ ID NO: 2;
and having a binding ability to guide RNA.

[13] The protein of the above-mentioned [9] consisting of a sequence comprising an amino acid sequence resulting from substitutions of
glutamic acid at the 782-position with lysine;
leucine at the 800-position with arginine;
asparagine at the 968-position with arginine;
asparagine at the 985-position with alanine;
asparagine at the 986-position with alanine;
arginine at the 991-position with alanine;
leucine at the 988-position with histidine;
alanine at the 1021-position with serine;
alanine at the 889-position with asparagine;
threonine at the 927-position with lysine;
lysine at the 929-position with asparagine; in the amino acid sequence shown in SEQ ID NO: 2;
and having a binding ability to guide RNA.

[14] The protein of the above-mentioned [1] consisting of a sequence comprising an amino acid sequence resulting from substitutions of
glutamic acid at the 782-position with lysine,
leucine at the 800-position with arginine;
asparagine at the 968-position with arginine;
asparagine at the 985-position with alanine;
asparagine at the 986-position with alanine;
arginine at the 991-position with alanine;
leucine at the 988-position with histidine;
alanine at the 1021-position with serine; in the amino acid sequence shown in SEQ ID NO: 2;
and having a binding ability to guide RNA.

[15] The protein of the above-mentioned [1] consisting of a sequence comprising an amino acid sequence resulting from substitutions of
glutamic acid at the 782-position with lysine,
leucine at the 800-position with arginine;
asparagine at the 968-position with arginine;
asparagine at the 985-position with alanine;
arginine at the 991-position with alanine;
alanine at the 1021-position with serine;
threonine at the 927-position with lysine;
lysine at the 929-position with asparagine;
isoleucine at the 1017-position with phenylalanine; in the amino acid sequence shown in SEQ ID NO: 2;
and having a binding ability to guide RNA.

[16] The protein of any of the above-mentioned [1] to [15], having identity of 80% or more at a site other than the mutated positions in the SEQ ID NO: 2.

[17] The protein of any of the above-mentioned [1] to [15], wherein one to several amino acids are substituted, deleted, inserted and/or added at a site other than the mutated positions in the SEQ ID NO: 2.

[18] The protein of any of the above-mentioned [1] to [17], which has RNA-guided DNA endonuclease activity.

[19] The protein of any of the above-mentioned [1] to [17], further having a mutation that deletes nuclease activity in the amino acid sequence shown in SEQ ID NO: 2.

[20] The protein of any of the above-mentioned [1] to [17], having mutation in the protein of the above-mentioned [19] at sites corresponding to the 10-position, the 556-position, the 557-position and/or the 580-position in the amino acid sequence shown in SEQ ID NO: 2.

[21] The protein of the above-mentioned [20], wherein the mutation at the 10-position is substitution of aspartic acid with alanine; the mutation at the 556-position is substitution of aspartic acid with alanine; the mutation at the 557-position is substitution of histidine with alanine; and the mutation at the 580-position is substitution of asparagine with alanine.

[22] The protein of any of the above-mentioned [19] to [21], wherein a transcriptional regulator protein or domain is linked.

[23] The protein of the above-mentioned [22], wherein the transcriptional regulator is a transcription activator.

[24] The protein of the above-mentioned [23], wherein the transcriptional regulator is a transcription silencer or a transcription inhibitor.

[25] A nucleic acid encoding the protein of any of the above-mentioned [1] to [24].

[26] A protein-PNA complex provided with the protein of any of the above-mentioned [1] to [24] and a guide RNA comprising a polynucleotide composed of a base sequence complementary to a base sequence located 1 to 20 to 24 bases upstream from a proto-spacer adjacent motif (PAM) sequence in a target double-stranded polynucleotide.

[27] A method for site-specifically modifying a target double-stranded polynucleotide, including
a step of mixing and incubating a target double-stranded polynucleotide, a protein and a guide RNA, and
a step of having the aforementioned protein modify the aforementioned target double-stranded polynucleotide at a binding site located upstream of a PAM sequence; wherein,
the aforementioned target double-stranded polynucleotide has a PAM sequence composed of NNGNNN (wherein, N is any base and G is guanine),
the aforementioned protein is the protein of any of the above-mentioned [1] to [24], and
the aforementioned guide RNA contains a polynucleotide composed of a base sequence complementary to a base sequence located 1 to 20 to 24 bases upstream from the aforementioned PAM sequence in the aforementioned target double-stranded polynucleotide.
[28] The method of the above-mentioned [27], wherein the modification is site specific cleavage in the target double-stranded polynucleotide.
[29] The method of the above-mentioned [27], wherein the modification is site specific substitution, deletion and/or addition of one or more nucleotides in the target double-stranded polynucleotide.
[30] A method for increasing expression of a target gene in a cell, comprising expressing the protein of the above-mentioned [23] and one or plural guide RNAs for the aforementioned target gene in the aforementioned cell.
[31] A method for decreasing expression of a target gene in a cell, comprising expressing the protein of the above-mentioned [24] and one or plural guide RNAs for the aforementioned target gene in the aforementioned cell.
[32] The method of the above-mentioned [30] or [31], wherein the cell is a eukaryotic cell.
[33] The method of the above-mentioned [30] or [31], wherein the cell is a yeast cell, a plant cell or an animal cell.

Effect of the Invention

According to the present invention, a Cas9 protein can be obtained that recognizes a wide range of PAM sequences while retaining binding strength with a guide RNA. In addition, a simple and rapid site-specific genome editing technology for a target sequence can be provided that uses the aforementioned Cas9 protein.

BRIEF DESCRIPTION OF THE DRAWINGS

FIG. 7 shows the amino acid sequence (FIG. 7-1) (SEQ ID NO: 40) of NLS-PF(v15)-dSaCas(D10A,N580A)-NLS-KRAB-P2A-Puro fusion protein (sometimes to be abbreviated as PF(v15)-dSaCas9(D10A, N580A)-KRAB) and a base sequence encoding same (FIG. 7-2) (SEQ ID NO: 39).
FIG. 8 shows the amino acid sequence (FIG. 8-1) (SEQ ID NO: 42) of NLS-PF(v51)-dSaCas(D10A,N580A)-NLS-KRAB-P2A-Puro fusion protein (sometimes to be abbreviated as PF(v51)-dSaCas9(D10A, N580A)-KRAB) and a base sequence encoding same (SEQ ID NO: 41) (FIG. 8-2).
FIG. 9 shows that PF(v15)-dSaCas9 suppresses expression of KRAS gene more strongly than WT-dSaCas9.

DESCRIPTION OF EMBODIMENTS

Figure 1:
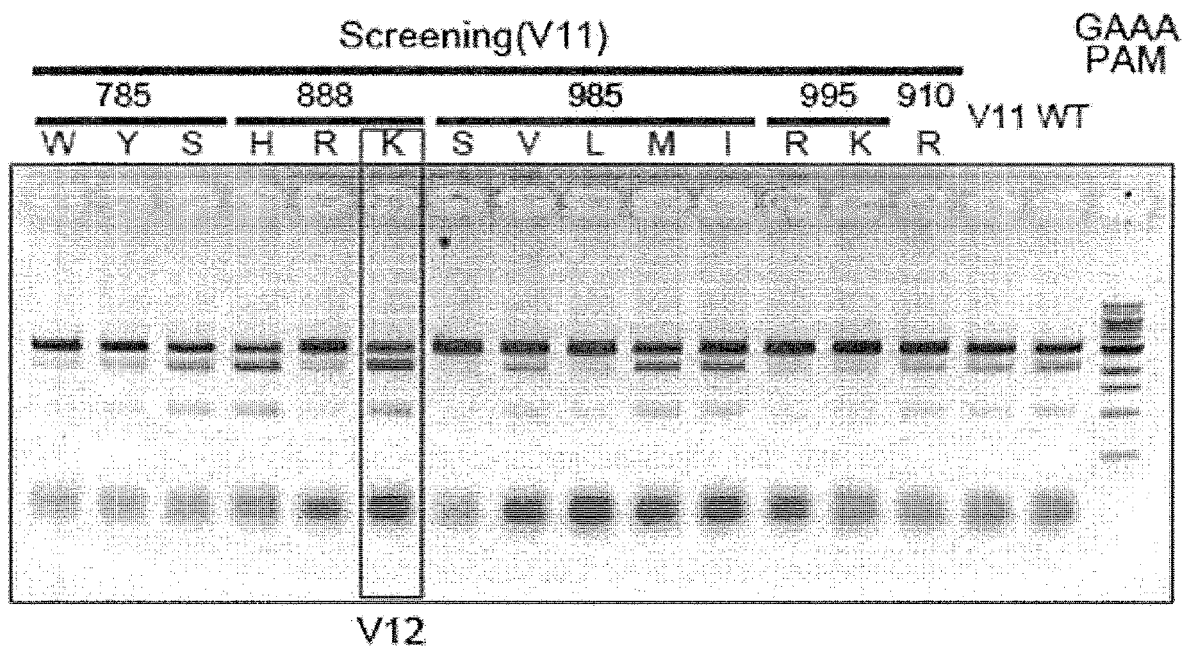
FIG. 1 shows an image representing the results of agarose gel electrophoresis in a DNA cleavage activity measurement test in Example 1. "(NN)GAAA" was used as the PAM sequence.

The present invention is described below. Unless particularly indicated, the terms used in the present specification have meanings generally used in the pertinent field.

<Cas9 Protein Recognizing Wide Range of PAM Sequences>

The protein of the present embodiment is a Cas9 protein that recognizes a wide range of PAM sequences while retaining binding strength with a guide RNA. According to the protein of the present embodiment, a simple and rapid technique can be provided for site-specific editing of the genome of a target sequence.

In the present description, "guide RNA" refers to that which mimics the hairpin structure of tracrRNA-crRNA, and contains in the 5'-terminal region thereof a polynucleotide composed of a base sequence complementary to a base sequence located from 1 to preferably 20 to 24 bases, and more preferably from 1 to preferably 22 to 24 bases, upstream from the PAM sequence in a target double-stranded polynucleotide. Moreover, guide RNA may contain one or more polynucleotides composed of a base sequence allowing the obtaining of a hairpin structure composed of base sequences non-complementary to a target double-stranded polynucleotide symmetrically arranged so as to form a complementary sequence having a single point as the axis thereof.

The guide RNA has a function of binding to the mutant Cas9 protein of the present invention and leading the protein to a target DNA. The guide RNA has a sequence at the 5'-terminal which is complementary to the target DNA, and binds to the target DNA via the complementary sequence, thereby leading the mutant Cas9 protein of the present invention to the target DNA. When the mutant Cas9 protein functions as a DNA endonuclease, the DNA can be cleaved at the site where the target DNA exists and, for example, the function of the target DNA can be specifically lost.

The guide RNA is designed and prepared based on the sequence information of the target DNA to be cleaved or modified. Specific examples include sequences such as those used in the Examples.

In the present description, an "endonuclease" refers to an enzyme that cleaves a nucleotide strand at an intermediate location. Therefore, the Cas9 protein of the present embodiment that recognizes a wide range of PAM sequences and has endonuclease activity has enzyme activity guided by guide RNA that cleaves at an intermediate location of a DNA strand.

In the present description, the terms "polypeptide", "peptide" and "protein" refer to polymers of amino acid residues and are used interchangeably. In addition, these terms also refer to amino acid polymers in which one or a plurality of amino acid residues are in the form of a chemical analog or modified derivative of the corresponding amino acids present in nature.

In the present specification, the "non-aromatic amino acid" means an amino acid not having a benzene ring, such as glutamic acid, alanine, proline, valine, leucine, isoleucine and the like.

In the present description, a "DNA sequence" refers to a nucleotide sequence of an arbitrary length, is a deoxyribonucleotide or ribonucleotide, and may be linear or branched and single-stranded or double-stranded.

In the present description, a "PAM sequence" refers to a sequence present in a target double-stranded polynucleotide that can be recognized by Cas9 protein, and the length and base sequence of the PAM sequence differs according to the bacterial species. A sequence capable of being recognized by the Cas9 protein of the present embodiment capable of recognizing a wide range of PAM sequences can be represented by "5'-NNGNNN-3'.

Furthermore, in the present description, "N" refers to any one base selected from the group consisting of adenine, cytosine, thymine and guanine, "A" refers to adenine, "G" to guanine, "C" to cytosine, "T" to thymine, "R" to a base having a purine skeleton (adenine or guanine), and "Y" to a base having a pyrimidine skeleton (cytosine or thymine).

In the present description, a "polynucleotide" refers to a deoxyribonucleotide or ribonucleotide polymer having linear or cyclic coordination and may be single-stranded or double-stranded, and should not be interpreted as being restricted with respect to polymer length. In addition, polynucleotides include known analogs of naturally-occurring nucleotides as well as nucleotides in which at least one of the base moieties, sugar moieties and phosphate moieties thereof has been modified (such as a phosphorothioate backbone). In general, an analog of a specific nucleotide has the same base-pairing specificity, and for example, A analogs form base pairs with T.

In one embodiment, the present invention provides a protein consisting of an amino acid sequence resulting from mutations of the 985-position and the 991-position, and optionally the 986-position, and at least one, two, three, four, five, six or seven sites selected from the group consisting of the 782-position, the 800-position, the 888-position, the 968-position, the 988-position, the 1017-position and the 1021-position in the amino acid sequence shown in SEQ ID NO: 2, and having a binding ability to guide RNA (embodiment 1). The protein of embodiment 1 has RNA-guided DNA endonuclease activity.

SEQ ID NO: 2 is a full-length amino acid sequence of SaCas9 protein.

The mutation at the 782-position of SEQ ID NO: 2 is specifically substitution of glutamic acid at the 782-position with lysine or arginine, preferably substitution with lysine.

The mutation at the 800-position of SEQ ID NO: 2 is specifically substitution of leucine at the 800-position with arginine or lysine, preferably substitution with arginine.

The mutation at the 888-position of SEQ ID NO: 2 is specifically substitution of asparagine at the 888-position with an amino acid selected from the group consisting of lysine, arginine, asparagine, glutamine, histidine and serine, preferably substitution with lysine.

The mutation at the 968-position of SEQ ID NO: 2 is specifically substitution of asparagine at the 968-position with arginine or lysine, preferably substitution with arginine.

The mutation at the 985-position of SEQ ID NO: 2 is specifically substitution of asparagine at the 985-position with an amino acid selected from the group consisting of alanine, serine, threonine, cysteine, valine and isoleucine, preferably substitution with alanine.

The mutation at the 986-position of SEQ ID NO: 2 is specifically substitution of asparagine at the 986-position with an amino acid selected from the group consisting of alanine, serine, threonine, cysteine, valine and isoleucine, preferably substitution with alanine.

The mutation at the 988-position of SEQ ID NO: 2 is specifically substitution of leucine at the 988-position with histidine.

The mutation at the 991-position of SEQ ID NO: 2 is specifically substitution of arginine at the 991-position with a non-aromatic amino acid, preferably substitution with alanine.

The mutation at the 1017-position of SEQ ID NO: 2 is specifically substitution of isoleucine at the 1017-position with a bulkier amino acid. By substitution with a bulky amino acid, stabilization by interaction with the side chain of arginine at the 1015-position is expected. Examples of the bulky amino acid include phenylalanine, methionine, tyrosine, tryptophan and proline. Preferred is substitution with phenylalanine.

The mutation at the 1021-position of SEQ ID NO: 2 is specifically substitution of alanine at the 1021-position with an amino acid selected from the group consisting of serine, threonine and asparagine, preferably substitution with serine.

In another embodiment of the present invention, the present invention provides a protein further having mutations at the 927-position and the 929-position and having binding ability to guide RNA (embodiment 2) in addition to the mutation of the aforementioned embodiment 1. In addition, the protein of embodiment 2 has RNA-guided DNA endonuclease activity.

The mutation at the 927-position is specifically substitution of threonine at the 927-position with lysine or arginine, preferably substitution with lysine.

The mutation at the 929-position is specifically substitution of lysine at the 929-position with asparagine, aspartic acid or alanine, preferably substitution with asparagine.

In another embodiment of the present invention, the present invention provides a protein further having a mutation at the 929-position and having binding ability to guide RNA (embodiment 3) in addition to the mutation of the aforementioned embodiment 1. The protein of embodiment 3 has RNA-guided DNA endonuclease activity.

The mutation at the 929-position is specifically substitution of lysine at the 929-position with arginine.

In another embodiment of the present invention, the present invention provides a protein having a mutation at the 927-position in addition to the mutation of the aforementioned embodiment 1. The protein of embodiment 4 has RNA-guided DNA endonuclease activity.

The mutation at the 927-position is specifically substitution of threonine at the 927-position with lysine.

In another embodiment of the present invention, the present invention provides a protein having a further mutation at the 889-position in addition to the mutation of the aforementioned embodiment 1, and having a binding ability to guide RNA (embodiment 5). The protein of embodiment 5 has RNA-guided DNA endonuclease activity.

The mutation at the 889-position is specifically substitution of alanine at the 889-position with asparagine, serine, lysine, arginine or histidine, preferably substitution with asparagine.

In another embodiment of the present invention, the present invention provides a protein having further mutations at the 927-position, 929-position and 889-position in addition to the mutation of the aforementioned embodiment 1, and having a binding ability to guide RNA (embodiment 6). The protein of embodiment 6 additionally has RNA-guided DNA endonuclease activity.

The mutation at the 927-position is specifically substitution of threonine at the 927-position with lysine or arginine, preferably lysine.

The mutation at the 929-position is specifically substitution of lysine at the 929-position with asparagine, aspartic acid or alanine, preferably asparagine.

The mutation at the 889-position is specifically substitution with asparagine.

In another embodiment of the present invention, the present invention provides a protein (embodiment 7) that is functionally equivalent to the proteins of the aforementioned embodiments 1-6. To be functionally equivalent to the proteins of the aforementioned embodiments 1-6, the amino acid sequence having identity of 80% or more at a site other than the positions where the mutations have been applied in the SEQ ID NO: 2 in the aforementioned embodiments 1-6 and has a binding ability to guide RNA. When amino acids are increased or decreased due to mutation, the "site other than the positions where the mutations have been applied" can be interpreted to mean a "site other than the positions corresponding to the positions where the mutations have been applied". This identity is preferably 80% or more, more preferably 85% or more, even more preferably 90% or more, particularly preferably 95% or more, and most preferably 99% or more. The amino acid sequence identity can be determined by a method known per se. For example, amino acid sequence identity (%) can be determined using a program conventionally used in the pertinent field (e.g., BLAST, FASTA, etc.) by default. In another aspect, identity (%) is determined by any algorithm known in the pertinent field, such as algorithms of Needleman et al. (1970) (J. Mol. Biol. 48: 444-453), Myers and Miller (CABIOS, 1988, 4: 11-17) and the like. The algorithm of Needleman et al. is incorporated into the GAP program in the GCG software package (available at www.gcg.com) and the identity (%) can be determined using, for example, any of BLOSUM 62 matrix and PAM250 matrix, as well as gap weight: 16, 14, 12, 10, 8, 6 or 4, and length weight: 1, 2, 3, 4, 5 or 6. The algorithm of Myers and Miller is incorporated into the ALIGN program that is a part of the GCG sequence alignment software package. When the ALIGN program is used to compare amino acid sequences, for example, PAM120 weight residue table, gap length penalty 12, and gap penalty 4 can be used.

As a protein functionally equivalent to the proteins of the aforementioned embodiments 1-6, a protein which comprises one to several amino acids substituted, deleted, inserted and/or added at site(s) other than the positions where the mutations have been applied in the SEQ ID NO: 2 in the aforementioned embodiment 1-6 and having the binding ability to guide RNA (embodiment 7) is provided. When amino acids are increased or decreased due to mutation, the "site other than the positions where the mutations have been applied" can be interpreted to mean a "site other than the positions corresponding to the positions where the mutations have been applied".

As a technique for artificially performing "substitution, deletion, insertion and/or addition of amino acid", for example, a method including applying conventional site specific mutation introduction to DNA encoding a predetermined amino acid sequence, and thereafter expressing the DNA by a conventional method can be mentioned. Examples of the site specific mutation introduction method include a method using amber mutation (gapped duplex method, Nucleic Acids Res., 12, 9441-9456 (1984)), a PCR method using a mutation introduction primer and the like.

The number of the amino acids modified above is at least one residue, specifically one or several, or more than that. Among the aforementioned substitution, deletion, insertion and addition, substitution of amino acid is particularly preferred. The substitution is more preferably substitution with an amino acid having similar properties such as hydrophobicity, charge, pK, and characteristic of steric structure and the like. Examples of the substitution include substitution within the groups of i) glycine, alanine; ii) valine, isoleucine, leucine; iii) aspartic acid, glutamic acid, asparagine, glutamine; iv) serine, threonine; v) lysine, arginine; vi) phenylalanine, tyrosine.

In another embodiment of the present invention, the present invention provides a protein having further mutations at the 10-position, the 556-position, the 557-position and/or the 580-position in the SEQ ID NO: 2, in addition to the mutations of the aforementioned embodiments 1 to 7, and having a binding ability to guide RNA (embodiment 8). In the present specification, the amino acid residue at the "corresponding position" is identified by comparing the target amino acid sequence with a reference sequence (the amino acid sequence shown in SEQ ID NO: 2) by the use of a known algorithm, and aligning the sequence so as to confer maximum homology to the conserved amino acid residues present in the amino acid sequence of each protein having mutation. By aligning the amino acid sequence of each protein by this method, it is possible to determine the position of the amino acid residue to be mutated in the sequence regardless of the insertion or deletion contained in the amino acid sequence.

The mutation at the 10-position is specifically substitution of the 10-position aspartic acid with alanine or asparagine.

The mutation at the 10-position is specifically substitution of aspartic acid at the 10-position with alanine.

The mutation at the 556-position is specifically substitution of aspartic acid at the 556-position with alanine.

The mutation at the 557-position is specifically substitution of histidine at the 557-position with alanine.

The mutation at the 580-position is specifically substitution of asparagine at the 580-position with alanine.

Preferred as embodiment 8 are a protein in which aspartic acid at the 10-position is substitution with alanine; a protein in which asparagine at the 580-position is substituted with alanine; and a protein in which aspartic acid at the 10-position is substitution with alanine and asparagine at the 580-position is substituted with alanine. The first two proteins have nickase activity, and the third protein binds to guide RNA and led to the target DNA but the endonuclease activity is inactivated.

A preferable example of the Cas9 protein recognizing a wide range of the PAM sequence of the present invention is, for example, a protein having an amino acid sequence resulting from mutations of glutamic acid at the 782-position to lysine (E782K), leucine at the 800-position to arginine (L800R), asparagine at the 968-position to arginine (N968R), asparagine at the 985-position to alanine (N985A), asparagine at the 986-position to alanine (N986A), arginine at the 991-position to alanine (R991A), leucine at the 988-position to histidine (L988H), alanine at the 1021-position to serine (A1021S), threonine at the 927-position to lysine (T927K), and lysine at the 929-position to asparagine (K929N) in the SEQ ID NO: 2.

In this specification, the alphabet displayed on the left side of the number indicating the number of amino acid residues up to the substitution site indicates a single letter code of the amino acid before substitution of the amino acid sequence of SEQ ID NO: 2, and the alphabet displayed on the right side indicates a single letter code of the amino acid after substitution.

Another preferable example of the Cas9 protein recognizing a wide range of the PAM sequence of the present invention is, for example, a protein having an amino acid sequence resulting from mutations of glutamic acid at the 782-position to lysine (E782K), leucine at the 800-position to arginine (L800R), asparagine at the 968-position to arginine (N968R), asparagine at the 985-position to alanine (N985A), asparagine at the 986-position to alanine (N986A), arginine at the 991-position to alanine (R991A), leucine at the 988-position to histidine (L988H), alanine at the 1021-position to serine (A1021S), alanine at the 889-position to asparagine (A889N), threonine at the 927-position to lysine (T927K), and lysine at the 929-position to asparagine (K929N) in the SEQ ID NO: 2.

Another preferable example of the Cas9 protein recognizing a wide range of the PAM sequence of the present invention is, for example, a protein having an amino acid sequence resulting from mutations of glutamic acid at the 782-position to lysine (E782K), leucine at the 800-position to arginine (L800R), asparagine at the 968-position to arginine (N968R), asparagine at the 985-position to alanine (N985A), asparagine at the 986-position to alanine (N986A), arginine at the 991-position to alanine (R991A), leucine at the 988-position to histidine (L988H), alanine at the 1021-position to serine (A1021S) in the SEQ ID NO: 2.

Another preferable example of the Cas9 protein recognizing a wide range of the PAM sequence of the present invention is, for example, a protein having an amino acid sequence resulting from mutations of glutamic acid at the 782-position to lysine (E782K), leucine at the 800-position to arginine (L800R), asparagine at the 968-position to arginine (N968R), asparagine at the 985-position to alanine (N985A), arginine at the 991-position to alanine (R991A), alanine at the 1021-position to serine (A1021S), threonine at the 927-position to lysine (T927K), lysine at the 929-position to asparagine (K929N), and isoleucine at the 1017-position to phenylalanine (I1017F) in the SEQ ID NO: 2.

A preferable example of the Cas9 protein recognizing a wide range of the PAM sequence of the present invention is, for example, a protein having an amino acid sequence resulting from mutations of glutamic acid at the 782-position to lysine (E782K), leucine at the 800-position to arginine (L800R), asparagine at the 968-position to arginine (N968R), asparagine at the 985-position to alanine (N985A), asparagine at the 986-position to alanine (N986A), arginine at the 991-position to alanine (R991A), leucine at the 988-position to histidine (L988H), alanine at the 1021-position to serine (A1021S), threonine at the 927-position to lysine (T927K), lysine at the 929-position to asparagine (K929N), aspartic acid at the 10-position to alanine (D10A), and asparagine at the 580-position to alanine (N580A) in the SEQ ID NO: 2.

Another preferable example of the Cas9 protein recognizing a wide range of the PAM sequence of the present invention is, for example, a protein having an amino acid sequence resulting from mutation of glutamic acid at the 782-position to lysine (E782K), leucine at the 800-position to arginine (L800R), asparagine at the 968-position to arginine (N968R), asparagine at the 985-position to alanine (N985A), arginine at the 991-position to alanine (R991A), alanine at the 1021-position to serine (A1021S), threonine at the 927-position to lysine (T927K), lysine at the 929-position to asparagine (K929N), isoleucine at the 1017-position to phenylalanine (I1017F)), aspartic acid at the 10-position to alanine (D10A), and asparagine at the 580-position to alanine (N580A) in the SEQ ID NO: 2.

The Cas9 protein recognizing a wide range of PAM sequences in the present embodiment can be produced according to, for example, the method indicated below. First, a host is transformed using a vector containing a nucleic acid that encodes the aforementioned Cas9 protein of the present invention recognizing a wide range of PAM sequences. Then, the host is cultured to express the aforementioned protein. Conditions such as medium composition, culture temperature, duration of culturing or addition of inducing agents can be determined by a person with ordinary skill in the art in accordance with known methods so that the transformant grows and the aforementioned protein is efficiently produced. In addition, in the case of having incorporated a selection marker in the form of an antibiotic resistance gene in an expression vector, the transformant can be selected by adding antibiotic to the medium. Then, Cas9 protein recognizing a wide range of PAM sequences is obtained by purifying the aforementioned protein expressed by the host according to a method known per se.

There are no particular limitations on the host, and examples thereof include animal cells, plant cells, insect cells and microorganisms such as *Escherichia coli, Bacillus subtilis* or yeast.

<Complex of Cas9 Protein Recognizing Wide Range of PMA Sequences and Guide RNA>

In one embodiment thereof, the present invention provides a protein-RNA complex provided with the protein indicated in the previous section on <Cas9 Protein Recognizing Wide Range of PMA Sequences> and guide RNA containing a polynucleotide composed of a base sequence complementary to a base sequence located 1 to 20 to 24 bases upstream from a proto-spacer adjacent motif (PAM) sequence in a target double-stranded polynucleotide.

According to the protein-RNA complex of the present embodiment, a wide range of PMA sequences can be recognized and a target double-stranded polynucleotide can be easily and rapidly edited site-specifically for a target sequence.

The aforementioned protein and the aforementioned guide RNA are able to form a protein-RNA complex by mixing in vitro and in vivo under mild conditions. Mild conditions refer to a temperature and pH of a degree that does not cause proteolysis or denaturation, and the temperature is preferably 4° C. to 40° C., while the pH is preferably 4 to 10.

In addition, the duration of mixing and incubating the aforementioned protein and the aforementioned guide RNA is preferably 0.5 hours to 1 hour. The complex formed by the aforementioned protein and the aforementioned guide RNA is stable and is able to maintain stability even if allowed to stand for several hours at room temperature.

<CRISPR-Cas Vector System>

In one embodiment thereof, the present invention provides a CRISPR-Cas vector system provided with a first vector containing a gene encoding a protein indicated in the previous section on <Cas9 Protein Recognizing Wide Range of PAM Sequences>, and a second vector containing a guide RNA containing a polynucleotide composed of a base sequence complementary to a base sequence located 1 to 20 to 24 bases upstream from PAM sequence in a target double-stranded polynucleotide.

According to the CRISPR-Cas vector system of the present embodiment, a target double-stranded polynucleotide can be easily and rapidly edited site-specifically for a target sequence.

The guide RNA is suitably designed to contain in the 5'-terminal region thereof a polynucleotide composed of a base sequence complementary to a base sequence located from 1 to 20 to 24 bases, and preferably to 22 to 24 bases, upstream from a PAM sequence in a target double-stranded polynucleotide. Moreover, the guide RNA may also contain one or more polynucleotides composed of a base sequence allowing the obtaining of a hairpin structure composed of base sequences non-complementary to a target double-stranded polynucleotide symmetrically arranged so as to form a complementary sequence having a single point as the axis thereof.

The vector of the present embodiment is preferably an expression vector. There are no particular limitations on the expression vector, and examples thereof that can be used include E. coli-derived plasmids such as pBR322, pBR325, puC12 or puCl3; B. subtilis-derived plasmids such as pUB110, pTP5 or pC194; yeast-derived plasmids such as pSH19 or pSH15; bacteriophages such as γphages; viruses such as adenovirus, adeno-associated virus, lentivirus, vaccinia virus or baculovirus; and modified vectors thereof.

In the aforementioned expression vector, there are no particular limitations on the promoters for expression of the aforementioned Cas9 protein or the aforementioned guide RNA, and examples thereof that can be used include promoters for expression in animal cells such as EF1α promoter, SRα promoter, SV40 promoter, LTR promoter, cytomegalovirus (CMV) promoter or HSV-tk promoter, promoters for expression in plant cells such as the 35S promoter of cauliflower mosaic virus (CaMV) or rubber elongation factor (REF) promoter, and promoters for expression in insect cells such as polyhedrin promoter or p10 promoter. These promoters can be suitably selected according to the aforementioned Cas9 protein and the aforementioned guide RNA, or the type of cells expressing the aforementioned Cas9 protein and the aforementioned guide RNA.

The aforementioned expression vector may also further have a multi-cloning site, enhancer, splicing signal, polyadenylation signal, selection marker or replication origin and the like.

<Method for Site-Specifically Modifying Target Double-Stranded Polynucleotide>

First Embodiment

In one embodiment thereof, the present invention provides a method for site-specifically modifying a target double-stranded polynucleotide, provided with:

a step for mixing and incubating a target double-stranded polynucleotide, a protein and a guide RNA, and a step for having the aforementioned protein modify the aforementioned target double-stranded polynucleotide at a binding site located upstream of a PAM sequence; wherein, the aforementioned target double-stranded polynucleotide has a PAM sequence composed of NNGNNN (wherein, N represents any base and G represents guanine), the aforementioned protein is the protein indicated in the above-mentioned <Cas9 Protein Recognizing Wide Range of PMA Sequences>, and the aforementioned guide RNA contains a polynucleotide composed of a base sequence complementary to a base sequence located 1 to 20 to 24 bases upstream from the aforementioned PAM sequence in the aforementioned target double-stranded polynucleotide.

According to the method of the present embodiment, a target double-stranded polynucleotide can be modified easily, rapidly and site-specifically for a target sequence by using mutant Cas9 protein recognizing a wide range of PAM sequences.

In the present embodiment, there are no particular limitations on the target double-stranded polynucleotide provided it has a PAM sequence composed of NNGNNN (wherein, N represents any base and G represents guanine).

In the present embodiment, the protein and guide RNA are as indicated in the previous section on <Cas9 Protein Recognizing Wide Range of PMA Sequences>.

The following provides a detailed explanation of the method for site-specifically modifying a target double-stranded polynucleotide.

First, the aforementioned protein and the aforementioned guide RNA are mixed and incubated under mild conditions. Mild conditions are as previously described. The incubation time is preferably 0.5 hours to 1 hour. A complex formed by the aforementioned protein and the aforementioned guide RNA is stable and is able to maintain stability even if allowed to stand for several hours at room temperature.

Next, the aforementioned protein and the aforementioned guide RNA form a complex on the aforementioned target double-stranded polynucleotide. The aforementioned protein recognizes PAM sequences, and binds to the aforementioned target double-stranded polynucleotide at a binding site located upstream of the PAM sequence. When the aforementioned protein has an endonuclease activity, the polynucleotide is cleaved at this site. As a result of the Cas9 protein recognizing the PAM sequence, and the double helix structure of the target double-stranded polynucleotide being pulled apart starting at the PAM sequence and annealing with a base sequence complementary to the target double-stranded polynucleotide in the guide RNA, the double helix structure of the target double-stranded polynucleotide is partially unraveled. At this time, the aforementioned Cas9 protein cleaves phosphate diester bonds of the target double-stranded polynucleotide at a cleavage site located upstream of the PAM sequence and a cleavage site located upstream of a sequence complementary to the PAM sequence.

Second Embodiment

In the present embodiment, an expression step may be further provided prior to the incubation step in which the protein indicated in the previous section on <Cas9 Protein Recognizing Wide Range of PAM Sequences> and guide RNA are expressed using the previously described CRISPR-Cas vector system.

In the expression step of the present embodiment, Cas9 protein and guide RNA are first expressed using the aforementioned CRISPR-Cas vector system. A specific expression method consists of transforming a host using an expression vector containing a gene that encodes Cas9 protein and an expression vector containing guide RNA, respectively. Then, the host is cultured to express the Cas9 protein and guide RNA. Conditions such as medium composition, culture temperature, duration of culturing or addition of inducing agents can be determined by a person with ordinary skill in the art in accordance with known methods so that the transformant grows and the aforementioned protein is efficiently produced. In addition, in the case of having incorporated a selection marker in the form of an antibiotic resistance gene in the expression vector, the transformant can be selected by adding antibiotic to the medium. Then, the Cas9 protein and guide PNA are obtained by purifying the Cas9 protein and guide RNA expressed by the host according to a suitable method.

<Method for Site-Specifically Modifying Target Double-Stranded Polynucleotide>

First Embodiment

In one embodiment thereof, the present invention provides a method for site-specifically modifying a target double-stranded polynucleotide, provided with:

a step for mixing and incubating a target double-stranded polynucleotide, a protein and a guide RNA, a step for having the protein bind with the target double-stranded polynucleotide at a binding site located upstream of a PAM sequence, and a step for obtaining a modified target double-stranded polynucleotide in a region determined by complementary binding between the guide RNA and the target double-stranded polynucleotide; wherein, the aforementioned protein is the protein indicated in the previous section on the aforementioned <Cas9 Protein Recognizing Wide Range of PAM Sequences>, and the aforementioned guide RNA contains a polynucleotide composed of a base sequence complementary to a base sequence located 1 to 20 to 24 bases upstream from the aforementioned PAM sequence in the aforementioned target double-stranded polynucleotide.

According to the method of the present embodiment, a target double-stranded polynucleotide can be modified easily, rapidly and site-specifically for a target sequence by using an RNA-guided DNA endonuclease improved in binding ability to guide RNA and cleavage activity.

In the present embodiment, the target double-stranded polynucleotide, protein and guide RNA are as indicated in the previous sections on <Cas9 Protein Recognizing Wide Range of PMA Sequences> and <Method for Site-Specifically Modifying Target Double-Stranded Polynucleotide>.

The following provides a detailed explanation of the method for site-specifically modifying a target double-stranded polynucleotide. The steps through site-specifically bind to a target double-stranded polynucleotide are the same as in the previous section on <Method for Site-Specifically Cleaving Target Double-Stranded Polynucleotide>. Then, a target double-stranded polynucleotide that has been modified as necessary in a region determined by complementary binding between the guide RNA and the target double-stranded polynucleotide is obtained.

In the present description, "modification" refers to a change in the base sequence of a target double-stranded polynucleotide. Examples thereof include cleavage of a target double-stranded polynucleotide, modification of the base sequence of a target double-stranded polynucleotide by inserting an exogenous sequence following cleavage (by physical insertion or insertion by replicating through homology-directed repair), and modification of the base sequence of a target double-stranded polynucleotide by non-homologous end-joining (NHEJ: rejoining the ends of DNA resulting from cleavage) following cleavage, as well as addition of functional protein or base sequence and the like.

Modification of a target double-stranded polynucleotide in the present embodiment makes it possible to introduce a mutation into the target double-stranded polynucleotide or disrupt or modify the function of the target double-stranded polynucleotide.

Second Embodiment

In the present embodiment, an expression step may be further provided prior to the incubation step in which the protein indicated in the previous section on <Cas9 Protein Recognizing Wide Range of PAM Sequences> and guide RNA are expressed using the previously described CRISPR-Cas vector system.

In the expression step of the present embodiment, Cas9 protein and guide RNA are first expressed using the aforementioned CRISPR-Cas vector system. The specific expression method is similar to the method exemplified in the second embodiment in the previous section on <Method for Site-Specifically Modifying Target Double-Stranded Polynucleotide>.

<Method for Site-Specifically Modifying Target Double-Stranded Polynucleotide in Cells>

In one embodiment thereof, the present invention provides a method for site-specifically modifying a target double-stranded polynucleotide in cells, provided with:

a step for introducing the previously described CRISPR-Cas9 vector system into a cell and expressing protein indicated in the previous section on <Cas9 Protein Recognizing Wide Range of PAM Sequences> and guide RNA, a step for having the aforementioned protein bind with the aforementioned target double-stranded polynucleotide at a binding site located upstream of a PAM sequence, and a step for obtaining a modified target double-stranded polynucleotide in a region determined by complementary binding between the aforementioned guide RNA and the aforementioned target double-stranded polynucleotide; wherein, the aforementioned guide PNA contains a polynucleotide composed of a base sequence complementary to a base sequence located 1 to 20 to 24 bases upstream from the aforementioned PAM sequence in the aforementioned target double-stranded polynucleotide.

In the expression step of the present embodiment, first, Cas9 protein and guide RNA are expressed in a cell using the aforementioned CRISPR-Cas vector system.

Examples of organisms serving as the origin of the cells targeted for application of the method of the present embodiment include prokaryote, yeast, animal, plant, insect and the like. There are no particular limitations on the aforementioned animals, and examples thereof include, but are not limited to, human, monkey, dog, cat, rabbit, swine, bovine, mouse, rat and the like. In addition, the type of organism serving as the source of the cells can be arbitrarily selected according to the desired type or objective of the target double-stranded polynucleotide.

Examples of animal-derived cells targeted for application of the method of the present embodiment include, but are not limited to, germ cells (such as sperm or ova), somatic cells composing the body, stem cells, progenitor cells, cancer cells isolated from the body, cells isolated from the body that are stably maintained outside the body as a result of having become immortalized (cell line), and cells isolated from the body for which the nuclei have been artificially replaced.

Examples of somatic cells composing the body include, but are not limited to, cells harvested from arbitrary tissue such as the skin, kidneys, spleen, adrenals, liver, lungs, ovaries, pancreas, uterus, stomach, small intestine, large intestine, urinary bladder, prostate gland, testes, thymus, muscle, connective tissue, bone, cartilage, vascular tissue, blood, heart, eyes, brain or neural tissue. Specific examples of somatic cells include, but are not limited to, fibroblasts, bone marrow cells, immunocytes (e.g., B lymphocytes, T lymphocytes, neutrophils, macrophages or monocytes etc.), erythrocytes, platelets, osteocytes, bone marrow cells, pericytes, dendritic cells, keratinocytes, adipocytes, mesenchymal cells, epithelial cells, epidermal cells, endothelial cells, intravascular endothelial cells, lymphatic endothelial cells, hepatocytes, pancreatic islet cells (e.g., α cells, β cells, δ cells, ε cells or PP cells etc.), chondrocytes, cumulus cells, glia cells, nerve cells (neurons), oligodendrocytes, microglia cells, astrocytes, cardiomyocytes, esophageal cells, muscle cells (e.g., smooth muscle cells or skeletal muscle cells etc.), melanocytes and mononuclear cells, and the like.

Stem cells refer to cells having both the ability to self-replicate as well as the ability to differentiate into a plurality of other cell lines. Examples of stem cells include, but are not limited to, embryonic stem cells (ES cells), embryonic tumor cells, embryonic germ stem cells, induced pluripotent stem cells (iPS cells), neural stem cells, hematopoietic stem cells, mesenchymal stem cells, hepatic stem cells, pancreatic stem cells, muscle stem cells, germ stem cells, intestinal stem cells, cancer stem cells and hair follicle stem cells, and the like.

Cancer cells are cells derived from somatic cells that have acquired reproductive integrity. Examples of the origins of cancer cells include, but are not limited to, breast cancer (e.g., invasive ductal carcinoma, ductal carcinoma in situ, inflammatory breast cancer etc.), prostate cancer (e.g., hormone-dependent prostate cancer or non-hormone dependent prostate cancer etc.), pancreatic cancer (e.g., pancreatic ductal carcinoma etc.), stomach cancer (e.g., papillary adenocarcinoma, mucinous carcinoma, adenosquamous carcinoma etc.), lung cancer (e.g., non-small cell lung cancer, small cell lung cancer, malignant mesothelioma etc.), colorectal cancer (e.g., gastrointestinal stromal tumor etc.), rectal cancer (e.g., gastrointestinal stromal tumor etc.), colorectal cancer (e.g., familial colorectal cancer, hereditary non-polyposis colorectal cancer, gastrointestinal stromal tumor etc.), small intestinal cancer (e.g., non-Hodgkin's lymphoma, gastrointestinal stromal tumor etc.), esophageal cancer, duodenal cancer, cancer of the tongue, pharyngeal cancer (e.g., nasopharyngeal carcinoma, oropharyngeal carcinoma, hypopharyngeal carcinoma etc.), head and neck cancer, salivary gland cancer, brain tumor (e.g., pineal astrocytoma, pilocytic astrocytoma, diffuse astrocytoma, anaplastic astrocytoma etc.), schwannoma, liver cancer (e.g., primary liver cancer, extrahepatic bile duct cancer etc.), kidney cancer (e.g., renal cell carcinoma, transitional cell carcinoma of the renal pelvis and ureter etc.), gall bladder cancer, bile duct cancer, pancreatic cancer, endometrial carcinoma, cervical cancer, ovarian cancer (e.g., epithelial ovarian cancer, extragonadal germ cell tumor, ovarian germ cell tumor, ovarian low malignant potential tumor etc.), bladder cancer, urethral cancer, skin cancer (e.g., intraocular (ocular) melanoma, Merkel cell carcinoma etc.), Hemangioma, malignant lymphoma (e.g., reticulum cell sarcoma, lymphosarcoma, Hodgkin's etc.), melanoma (malignant melanoma), thyroid cancer (e.g., medullary thyroid cancer etc.), parathyroid cancer, nasal cancer, paranasal cancer, bone tumor (e.g., osteosarcoma, Ewing's tumor, uterine sarcoma, soft tissue sarcoma etc.), metastatic medulloblastoma, vascular fibroma, protuberant dermatofibrosarcoma, retinal sarcoma, penile cancer, testicular cancer, pediatric solid tumor (e.g., Wilms tumor or pediatric kidney tumor etc.), Kaposi's sarcoma, AIDS-induced Kaposi's sarcoma, maxillary sinus tumor, fibrous histiocytoma, leiomyosarcoma, rhabdomyosarcoma, chronic myeloproliferative disease and leukemia (e.g., acute myeloid leukemia, acute lymphoblastic leukemia etc.).

Cell lines refer to cells that have acquired reproductive integrity through artificial manipulation ex vivo. Examples of cell lines include, but are not limited to, HCT116, Huh7, HEK293 (human embryonic kidney cells), HeLa (human cervical cancer cell line), HepG2 (human liver cancer cell line), UT7/TPO (human leukemia cell line), CHO (Chinese hamster ovary cell line), MDCK, MDBK, BHK, C-33A, HT-29, AE-1, 3D9, NsO/1, Jurkat, NIH3T3, PC12, S2, Sf9, Sf21, High Five and Vero.

Introduction of the CRISPR-Cas vector system into cells can be carried out using a method suitable for the viable cells used, and examples thereof include electroporation method, heat shock method, calcium phosphate method, lipofection method, DEAE dextran method, microinjection method, particle gun method, methods using viruses, and methods using commercially available transfection reagents such as FuGENE (registered trade mark) 6 Transfection Reagent (manufactured by Roche), Lipofectamine 2000 Reagent (manufactured by Invitrogen Corp.), Lipofectamine LTX Reagent (manufactured by Invitrogen Corp.) or Lipofectamine 3000 Reagent (manufactured by Invitrogen Corp.).

Then, the modification step is the same as the methods indicated in the first embodiment in the previous section on <Method for Site-Specifically Modifying Target Double-Stranded Polynucleotide>.

Modification of a target double-stranded polynucleotide in the present embodiment makes it possible to obtain cells in which a mutation has been introduced into the target double-stranded polynucleotide or the function of the target double-stranded polynucleotide has been disrupted and modified.

When an embodiment having no endonuclease activity is used as the mutant Cas9 protein of the present invention, the protein can bind to the aforementioned target double-stranded polynucleotide at a binding site located upstream of the PAM sequence but cannot remain there to cleave the double-stranded polynucleotide. Therefore, for example, when a labeled protein such as a fluorescent protein (e.g., GFP) is fused to the protein, the labeled protein can be bound to the target double-stranded polynucleotide via the guide RNA-mutant Cas9 protein. By appropriately selecting a substance to be bound to the mutant Cas9 protein, various functions can be imparted to the target double-stranded polynucleotide.

Furthermore, a transcriptional regulatory protein or domain can be linked to the N-terminal or C-terminal of the mutant Cas9 protein. Examples of the transcriptional regulator or domain thereof include transcriptional activator or domain thereof (e.g., VP64, NF-κB p65) and transcription silencer or domain thereof (e.g., heterochromatin protein 1 (HP1)) and transcription inhibitory factor or domain thereof (e.g., Kruppel associated box (KRAB), ERF repressor domain (ERD), mSin3A interacting domain (SID)).

Enzymes that modify the methylation state of DNA (e.g., DNA methyltransferase (DNMT), TET) and enzymes that modify histone subunits (e.g., histone acetyltransferase (HAT), histone deacetylase (HDAC), histone methyltransferase, histone demethylase) can also be linked.

<Gene Therapy>

In one embodiment thereof, the present invention provides a method and composition for gene therapy by carrying out genome editing. In contrast to previously known methods for targeted gene recombination, the method of the present embodiment can be carried out efficiently and inexpensively and can be applied to any cell or living organism. An arbitrary segment of a double-stranded nucleic acid of a cell or living organism can be modified by the gene therapy method of the present embodiment. The gene therapy method of the present embodiment utilizes both homologous and non-homologous recombination processes present in all cells.

In the present description, the term "genome editing" refers to a novel gene modification technology for carrying out a specific gene disruption or knock-in of a reporter gene by carrying out targeted recombination or targeted mutation using a technology such as the CRISPR/Cas9 system or transcription activator-like effector nucleases (TALEN).

In addition, in one embodiment thereof, the present invention provides a gene therapy method for carrying out targeted DNA insertion or targeted DNA deletion. This gene therapy method includes a step for transforming a cell using a nucleic acid construct containing donor DNA. The scheme relating to DNA insertion or DNA deletion after cleaving a target gene can be determined by a person with ordinary skill in the art in accordance with a known method.

In addition, in one embodiment thereof, the present invention provides a gene therapy method for carrying out gene manipulation at a specific genetic locus using both somatic cells and germ cells.

In addition, in one embodiment thereof, the present invention provides a gene therapy method for disrupting a gene in a somatic cell. Here, the gene expresses a product harmful to cells or living organisms by over-expressing a substance harmful to cells or living organisms. This type of gene is over-expressed in one or more cell types generated in a disease. Disruption of the aforementioned over-expressed gene by the gene therapy method of the present embodiment is able to bring about a more favorable state of health in an individual suffering from a disease attributable to the aforementioned over-expressed gene. Namely, therapeutic effects are manifested as a result of the gene being disrupted in only a very small proportion of cells, thereby leading to a reduction in the expression level thereof.

In addition, in one embodiment thereof, the present invention provides a gene therapy method for disrupting a gene in a germ cell. Cells in which a specific gene has been disrupted can be used to create living organisms that do not have the function of a specific gene. A gene can be completely knocked out in cells in which the aforementioned gene has been disrupted. This functional deficit in a specific cell can have a therapeutic effect.

In addition, in one embodiment thereof, the present invention provides a gene therapy method for inserting a donor DNA encoding a gene product. This gene product has a therapeutic effect in the case of having been constitutively expressed. An example of such a method consists of inserting donor DNA encoding an active promoter and insulin gene into an individual suffering from diabetes in order to induce insertion of the donor DNA in an individual group of pancreas cells. Next, the aforementioned individual group of pancreas cells containing the aforementioned donor DNA produces insulin making it possible to treat the diabetes patient. Moreover, a drug-related gene product can be made to be produced by inserting the aforementioned donor DNA into a plant. A gene of a protein product (such as insulin, lipase or hemoglobin) is inserted into the plant along with a control element (constitutively activated promoter or inducible promoter) to enable a large amount of a pharmaceutical to be produced in the plant. Next, this protein product is isolated from the plant.

Transgenic plants or transgenic animals can be produced by methods using nucleic acid transfer technology (McCreath, K. J. et al. (2000), Nature 405: 1066-1069; Polejaeva, I. A. et al. (2000), Nature 407: 86-90). A tissue type-specific vector or cell type-specific vector can be used to provide gene expression only in selected cells.

In addition, in the case of using the aforementioned method in germ cells, cells can be produced having a designed genetic modification by inserting donor DNA into a target gene and allowing all of the subsequent cells to undergo cell division.

Examples of application targets of the gene therapy method of the present embodiment include, but are not limited to, any living organisms, cultured cells, cultured tissue, cultured nuclei (including cells, tissue or nuclei able to be used to regenerate a living organism in cultured cells, cultured tissue or intact cultured nuclei) and gametes (e.g., ova or sperm in various stages of development).

Examples of the origins of cells targeted for application of the gene therapy method of the present embodiment include, but are not limited to, any living organisms (such as insect, fungi, rodent, bovine, sheep, goat, chicken and other agriculturally important animal along with other mammals (e.g., dog, cat or human, although not limited thereto)).

Moreover, the gene therapy method of the present embodiment can be used in plants. There are no particular limitations on those plants targeted for application of the gene therapy method of the present embodiment, and the gene therapy method of the present embodiment can be applied to various arbitrary plant species (e.g., monocotyledons or dicotyledons etc.).

While the present invention is explained in more detail in the following by referring to Examples, they do not limit the scope of the present invention.

EXAMPLE

Example 1: Evaluation of DNA Cleavage Activity of Mutant SaCas9

1. Preparation of Wild-Type and Mutant SaCas9
(1) Construct Design

Wild-type or mutant SaCas9 gene with codon optimized by gene synthesis was incorporated in pESUMO vector (Novagen). Moreover, a TEV recognition sequence was added between His tag and the SaCas9 gene. The design of the construct was such that six consecutive histidine residues (His tag) were linked followed by the addition of the TEV protease recognition site to the N-terminal of the Cas9 expressed by the completed construct.

The base sequences of the SaCas9 genes used are as follows.

base sequence of wild-type SaCas9: SEQ ID NO: 1
base sequence of mutant SaCas9(V11_E782K_L800R_A889R_N968R_N985A_N986A_L988H_R991_A_A1021S): a base sequence resulting from conversion of gag at the 2344-2346-position to aaa, ctg at the 2398-2400-position to cgt, gcc at the 2665-2667-position to cgt, aac at the 2902-2904-position to cgt, aac at the 2953-2955-position to gcg, aat at the 2956-2958-position to gcg, ctg at the 2962-2964-position to cac, cgc at the 2971-2973-position to gcg, and gcc at the 3061-3063-position to tct in the base sequence of SEQ ID NO: 1.

base sequence of mutant SaCas9(V11a(+N785W) E782K_N785W_L800R_A889R_N968R_N985A_ N986A_L988H_R991A_A1021S): a base sequence resulting from further conversion of aat at the 2353-2355-position to tgg in the base sequence of V11.

base sequence of mutant SaCas9(V11b (+N785Y)_E782K_N785Y_L800R_A889R_N968R_ N985A_N986A_L988H_R991A_A1021S): a base sequence resulting from further conversion of aat at the 2353-2353-position to tat in the base sequence of V11.

base sequence of mutant SaCas9(V11c (+N785S)_E782K_N785S_L800R_A889R_N968R_ N985A_N986A_L988H_R991A_A1021S): a base sequence resulting from further conversion of aat at the 2353-2353-position to agc in the base sequence of V11.

base sequence of mutant SaCas9(V11d (+N888H)_E782K_L800R_N888H_A889R_N968R_ N985A_N986A_L988H_R991A_A1021S): a base sequence resulting from further conversion of aat at the 2362-2364-position to cat in the base sequence of V11.

base sequence of mutant SaCas9(V11e (+N888R)_E782K_L800R_N888R_A889R_N968R_ N985A_N986A_L988H_R991A_A1021S): a base sequence resulting from further conversion of aat at the 2362-2364-position to cgt in the base sequence of V11.

base sequence of mutant SaCas9(V11f (N985S)_E782K_L800R_A889R_N968R_N985S_ N986A_L988H_R991A_A1021S): a base sequence resulting from conversion of gcg at the 2953-2955-position to tct in the base sequence of V11.

base sequence of mutant SaCas9(V11g (N985V)_E782K_L800R_A889R_N968R_N985V_ N986A_L988H_R991A_A1021S): a base sequence resulting from conversion of gcg at the 2953-2955-position to gtg in the base sequence of V11.

base sequence of mutant SaCas9(V11h (N985L)_E782K_L800R_A889R_N968R_N985L_ N986A_L988H_R991A_A1021S): a base sequence resulting from conversion of gcg at the 2953-2955-position to ctg in the base sequence of V11.

base sequence of mutant SaCas9(V11i (N985M)_E782K_L800R_A889R_N968R_N985M_ N986A_L988H_R991A_A1021S): a base sequence resulting from conversion of gcg at the 2953-2955-position to atg in the base sequence of V11.

base sequence of mutant SaCas9(V11j (N985I)_E782K_L800R_A889R_N968R_N985I_ N986A_L988H_R991A_A1021S): a base sequence resulting from conversion of gcg at the 2953-2955-position to att in the base sequence of V11.

base sequence of mutant SaCas9(V11k (+N995R)_E782K_L800R_A889R_N968R_N985A_ N986A_L988H_R991A_N995R_A1021S): a base sequence resulting from further conversion of aat at the 2983-2985-position to cgt in the base sequence of V11.

base sequence of mutant SaCas9(V11l (+N995K)_E782K_L800R_A889R_N968R_N985A_ N986A_L988H_R991A_N995K_A1021S): a base sequence resulting from further conversion of aat at the 2983-2985-position to aaa in the base sequence of V11.

base sequence of mutant SaCas9(V11m (+K910R)_E782K_L800R_A889R_K910R_N968R_ N985A_N986A_L988H_R991A_A1021S): a base sequence resulting from further conversion of aag at 2728-2730 to cgt in the base sequence of V11.

base sequence of mutant SaCas9(V11n (A889A)_E782K_L800R_N968R_N985A_N986A_ L988H_R991A_A1021S): a base sequence resulting from conversion of cgt at the 2665-2667-position to gcg (returned to wild-type) in the base sequence of V11.

base sequence of mutant SaCas9(V11o(A889A_+ T927K)_E782K_L800R_T927K_N968R_N985A_ N986A_L988H_R991A_A1021S): a base sequence resulting from conversion of cgt at the 2665-2667-position to gcg (returned to wild-type), and further conversion of act at the 2779-2781-position to aaa in the base sequence of V11.

base sequence of mutant SaCas9(V11p(A889A_+T927K_+ K929A)_E782K_L800R_T927K_K929A_N968R_ N985A_N986A_L988H_R991A_A1021S): a base sequence resulting from conversion of cgt at the 2665-2667-position to gcg (returned to wild-type), and further conversion of act at the 2779-2781-position to aaa, and aag at the 2785-2787-position to gcg in the base sequence of V11.

base sequence of mutant SaCas9(V11q(A889A_+ K929R)_E782K_L800R_K929R_N968R_N985A_ N986A_L988H_R991A_A1021S): a base sequence resulting from conversion of cgt at the 2665-2667-position to gcg (returned to wild-type), and aag at the 2785-2787-position to cgt in the base sequence of V11.

base sequence of mutant SaCas9(V11r (+T927K)_E782K_L800R_A889R_T927K_N968R_ N985A_N986A_L988H_R991A_A1021S): a base sequence resulting from further conversion of act at the 2779-2781-position to aaa in the base sequence of V11.

base sequence of mutant SaCas9(V11s (+K929R)_E782K_L800R_A889R_K929R_N968R_ N985A_N986A_L988H_R991A_A1021S): a base sequence resulting from further conversion of aag at the 2785-2787-position to cgt in the base sequence of V11.

base sequence of mutant SaCas9(V11t (K929A)_E782K_L800R_A889R_T927A_N968R_ N985A_N986A_L988H_R991A_A1021S): a base sequence resulting from further conversion of aag at the 2785-2787-position to gcg in the base sequence of V11.

base sequence of mutant SaCas9(V12_E782K_L800R_N888K_A889R_N968R_ N985A_N986A_L988H_R991A_A1021S): a base sequence resulting from conversion of gag at the 2344-2346-position to aaa, ctg at the 2398-2400-position to cgt, aat at the 2662-2664-position to aaa, gcc at the 2665-2667-position to cgt, aac at the 2902-2904-position to cgt, aac at the 2953-2955-position to gcg, aat at the 2956-2958-position to gcg, ctg at the 2962-2964-position to cac, cgc at the 2971-2973-position to gcg, and gcc at the 3061-3063-position to tct in the base sequence of SEQ ID NO: 1.

base sequence of mutant SaCas9(V15_E782K_L800R_T927K_K929N_N968R_N985A_N986A_L988H_R991A_A1021S): a base sequence resulting from conversion of gag at the 2344-2346-position to aaa, ctg at the 2398-2400-position to cgt, act at the 2779-2781-position to aaa, aag at the 2785-2787-position to aac, aac at the 2902-2904-position to cgt, aac at the 2953-2955-position to gcg, aat at the 2956-2958-position to gcg, ctg at the 2962-2964-position to cac, cgc at the 2971-2973-position to gcg, and gcc at the 3061-3063-position to tct in the base SEQ ID NO: 1.

base sequence of mutant SaCas9(V15a (+N785S)_E782K_N785S_L800R_T927K_K929N_N968R_N985A_N986A_L988H_R991A_A1021S): a base sequence resulting from further conversion of aat at the 2353-2355-position to agc in the base sequence of V15.

base sequence of mutant SaCas9(V15b (+N888H)_E782K_L800R_N888H_T927K_K929N_N968R_N985A_N986A_L988H_R991A_A1021S): a base sequence resulting from further conversion of aat at the 2662-2664-position to cat in the base sequence of V15.

base sequence of mutant SaCas9(V15c (+N888K)_E782K_L800R_N888K_T927K_K929N_N968R_N985A_N986A_L988H_R991A_A1021S): a base sequence resulting from further conversion of aat at the 2662-2664-position to aaa in the base sequence of V15.

base sequence of mutant SaCas9(V15d (+A889S)_E782K_L800R_A889S_T927K_K929N_N968R_N985A_N986A_L988H_R991A_A1021S): a base sequence resulting from further conversion of gcg at the 2665-2667-position to tct in the base sequence of V15.

base sequence of mutant SaCas9(V15e (K929L)_E782K_L800R_T927K_K929L_N968R_N985A_N986A_L988H_R991A_A1021S): a base sequence resulting from conversion of aac at the 2785-2787-position to ctg in the base sequence of V15.

base sequence of mutant SaCas9(V15f (N929I)_E782K_L800R_T927K_N929I_N968R_N985A_N986A_L988H_R991A_A1021S): a base sequence resulting from conversion of aac at the 2785-2787-position to atc in the base sequence of V15.

base sequence of mutant SaCas9(V16_E782K_L800R_A889N_T927K_K929N_N968R_N985A_N986A_L988H_R991A_A1021S): a base sequence resulting from conversion of gag at the 2344-2346-position to aaa, ctg at the 2398-2400-position to cgt, gcc at the 2665-2667-position to aac, act at the 2779-2781-position to aaa, aag at the 2785-2787-position to aac, aac at the 2902-290 4-position to cgt, aac at the 2953-2955-position to gcg, aat at the 2956-2958-position to gcg, ctg at the 2962-2964-position to cac, cgc at the 2971-2973-position to gcg, and gcc at the 3061-3063-position to tct in the base sequence of SEQ ID NO: 1.

base sequence of mutant SaCas9(V17_E782K_L800R_T927K_K929D_N968R_N985A_N986A_L988H_R991A_A1021S): a base sequence resulting from conversion of gag at the 2344-2346-position to aaa, ctg at the 2398-2400-position to cgt, act at the 2779-2781-position to aaa, aag at the 2785-2787-position to gat, aac at the 2902-2904-position to cgt, aac at the 2953-2955-position to gcg, aat at the 2956-2958-position to gcg, ctg at the 2962-2964-position to cac, cgc at the 2971-2973-position to gcg, and gcc at the 3061-3063-position to tct in the base sequence of SEQ ID NO: 1.

base sequence of mutant SaCas9(V43_E782K_L800R_T927K_K929N_N968R_N985A_R991A_A1021S): a base sequence resulting from conversion of gag at the 2344-2346-position to aaa, ctg at the 2398-2400-position to cgt, act at the 2779-2781-position to aaa, aag at the 2785-2787-position to aac, aac at the 2902-2904-position to cgt, aac at the 2953-2955-position to gcg, cgc at the 2971-2973-position to gcg, and gcc at the 3061-3063-position to tct in the base sequence of SEQ ID NO: 1.

base sequence of mutant SaCas9(V51_E782K_L800R_T927K_K929N_N968R_N985A_R991A_A1021S_I1017F): a base sequence resulting from conversion of atc at the 3049-3051-position to ttc in the base sequence of V43.

(2) The resulting vectors were used to transform *Escherichia coli* strain rosetta 2 (DE3). Subsequently, the *E. coli* were cultured in LB medium containing 20 µg/ml of kanamycin. After having cultured to OD=0.8, isopropyl-β-D-1-thiogalactopyranoside (IPTG) (final concentration: 0.5 mM) as an expression inducing agent was added followed by culturing for 20 hours at 20° C. Following culturing, the *E. coli* were recovered by centrifugation (8,000 g, 10 min).

(3) Purification of Wild-Type and Mutant SaCas9

The bacterial cells recovered in (2) were suspended in a Buffer A and subjected to ultrasonication. Supernatant was recovered by centrifugation (25,000 g, 30 min) followed by mixing with Mg-His beads equilibrated with Buffer A and gently admixing for 1 hour. After recovering the unadsorbed fraction, the column was washed once with Buffer A. It was washed once with buffer B with high salt concentration, after which washed once with high concentration buffer A. Finally, the target protein was eluted with a Buffer C with high imidazole concentration.

The compositions of Buffers A to C are shown below.
Buffer A: 20 mM Tris-HCl, pH 6.0, 300 mM NaCl, 20 mM imidazole
Buffer B: 20 mM Tris-HCl, pH 0.0, 1000 mM NaCl, 20 mM imidazole
Buffer C: 20 mM Tris-HCl, pH 8.0, 300 mM NaCl, 300 mM imidazole 2. Preparation of Guide RNA A vector inserted with the target guide RNA sequence was prepared. A T7 promoter sequence was added upstream from the guide RNA sequence followed by incorporating a linearized pUC119 vector (Takara Corp.). Template DNA for an in vitro transcription reaction was produced using PCR based on the resulting vector. An in vitro transcription reaction was carried out by T7 RNA polymerase for 4 hours at 37° C. using this DNA template. The transcription product was purified by RNeasy. The base sequence consisting of a guide sequence and a scaffold is shown in SEQ ID NO: 3.

3. Plasmid DNA Cleavage Activity Measurement Test

Vectors inserted with the target DNA sequence and PAM sequence (5'-NNGAAA-3') were prepared for use in a DNA cleavage activity measurement test. PAM sequences were each added to the target DNA sequence and incorporated in a linearized pUC119 vector (SEQ ID NO: 4).

*Escherichia coli* strain Mach1 (Life Technologies) was transformed using the prepared vectors followed by culturing at 37° C. in LB medium containing 20 μg/mL of ampicillin.

Following culturing, the bacterial cells were recovered by centrifugation (8,000 g, 1 min) and the plasmid DNA was purified using the QIAprep Spin Miniprep Kit (QIAGEN).

Figure 2:
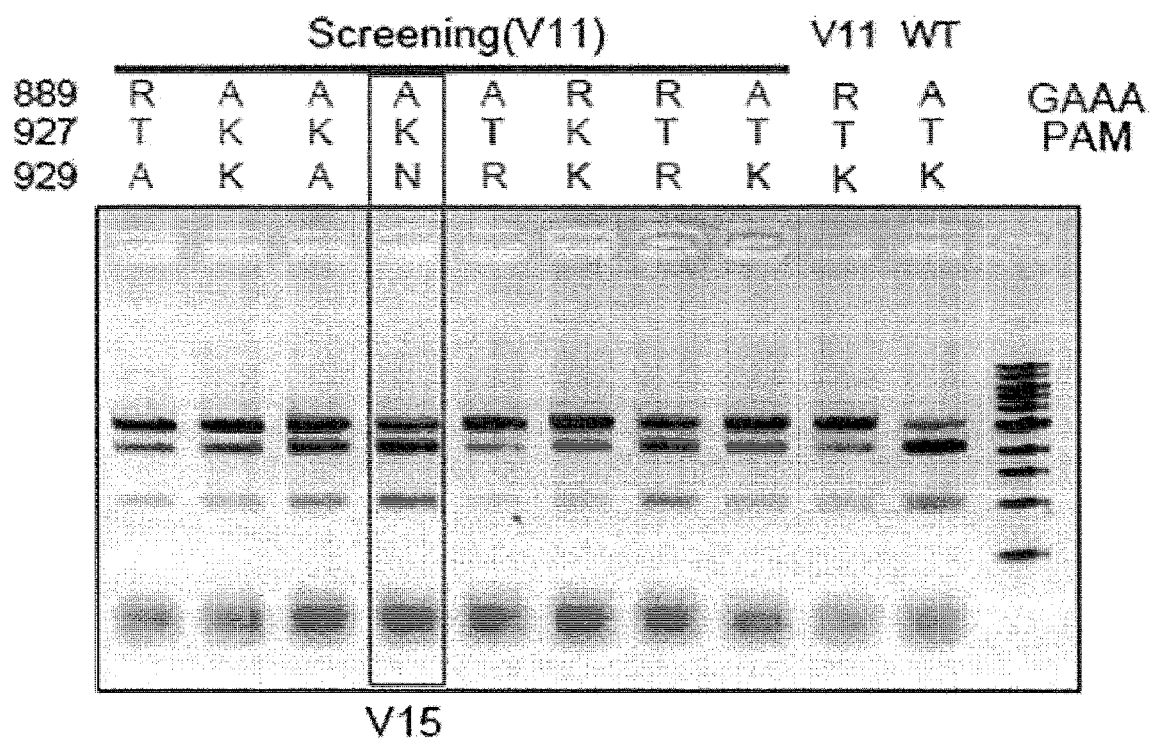
FIG. 2 shows an image representing the results of agarose gel electrophoresis in a DNA cleavage activity measurement test in Example 1. "(NN)GAAA" was used as the PAM sequence.
Figure 3:
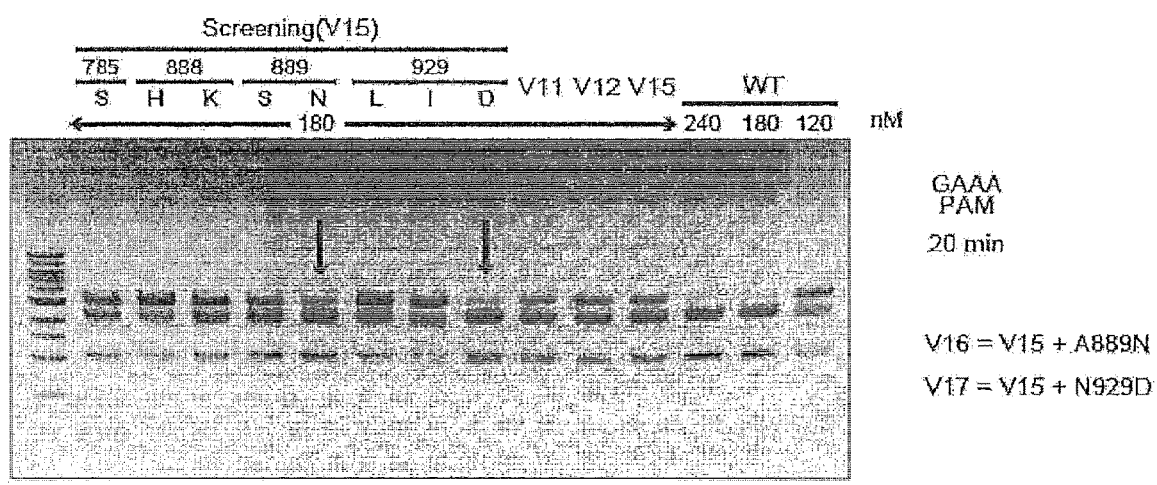
FIG. 3 shows an image representing the results of agarose gel electrophoresis in a DNA cleavage activity measurement test in Example 1. "(NN)GAAA" was used as the PAM sequence.

A cleavage experiment was carried out using the purified target plasmid DNA containing PAM sequence. The plasmid DNA was linearized into a single strand with restriction enzyme. When the wild-type or mutant SaCas9 was cleaved from the target DNA sequence in this linearized DNA, approximately 1000 bp and 2000 bp cleavage products were obtained. As the buffer for cleavage, cleavage buffer B with the following composition was used.

composition of cleavage buffer B (×10)
  200 mM HEPES 7.5
  1000 mM KCl
  50% glycerol
  10 mM DTT
  5 mM EDTA
  20 mM MgCl$_2$ The samples after reaction were electrophoresed using 1% concentration of agarose gel, and bands corresponding to the cleavage products were confirmed. The results are shown in FIGS. 1 to 3.

Example 2: Confirmation of Preference of Mutant SaCas9 for PAM Sequence

Using each mutant and wild-type SaCas9 prepared in Example 1 as mutant SaCas9, cleavage activity was examined in the same manner as in Example 1, and preference for various PAM sequences was confirmed. The PAM sequences 1-4 are shown in Table 1.

TABLE 1

|  | base sequence |
| --- | --- |
| PAM sequence 1 | 5'-NNGAAA-3' |
| PAM sequence 2 | 5'-NNGTTT-3' |
| PAM sequence 3 | 5'-NNGGGG-3' |
| PAM sequence 4 | 5'-NNGCCC-3' |

Figures 1, 4:
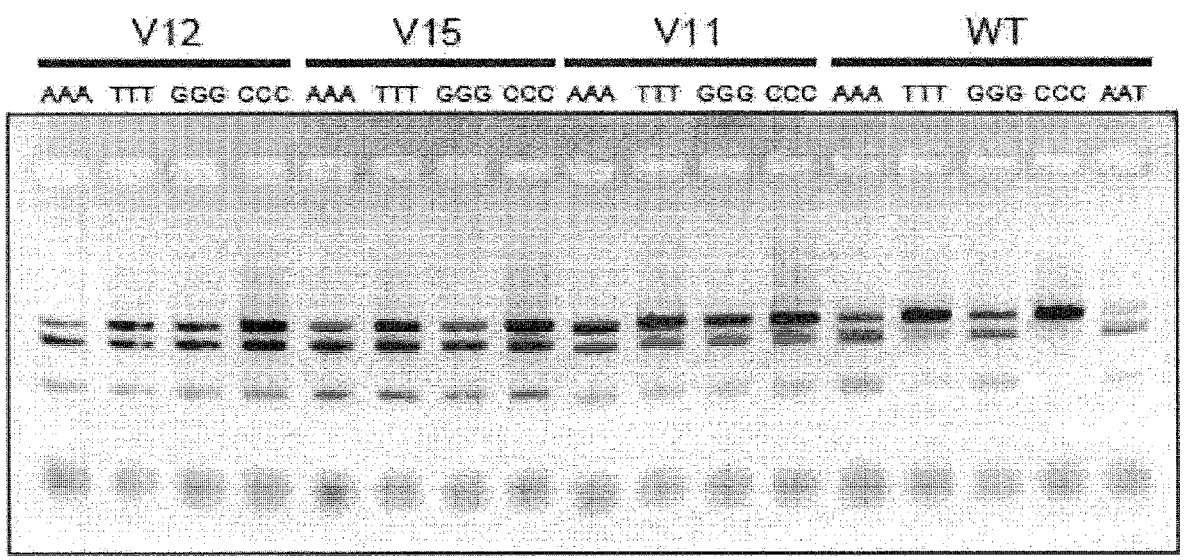
FIG. 4 shows images representing the results of agarose gel electrophoresis in a DNA cleavage activity measurement test in Example 2. PAM sequences of various mutant Cas9 proteins were examined.
Figures 2, 4:
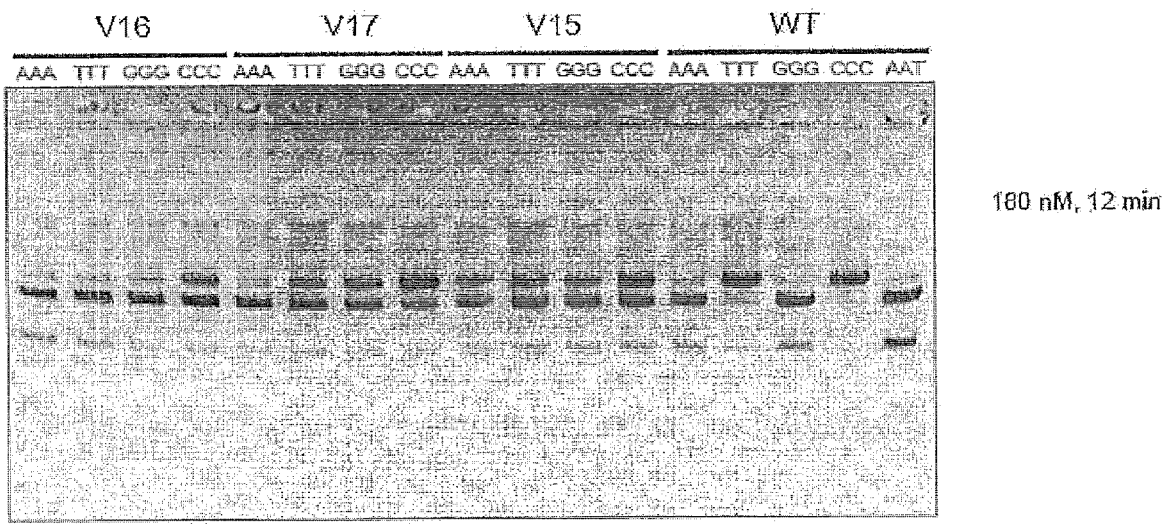
Figures 3, 4:
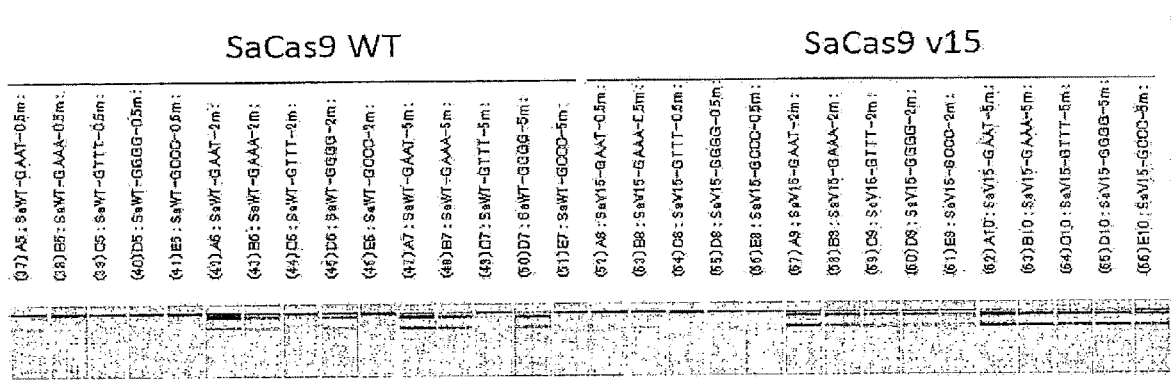
Figure 4:
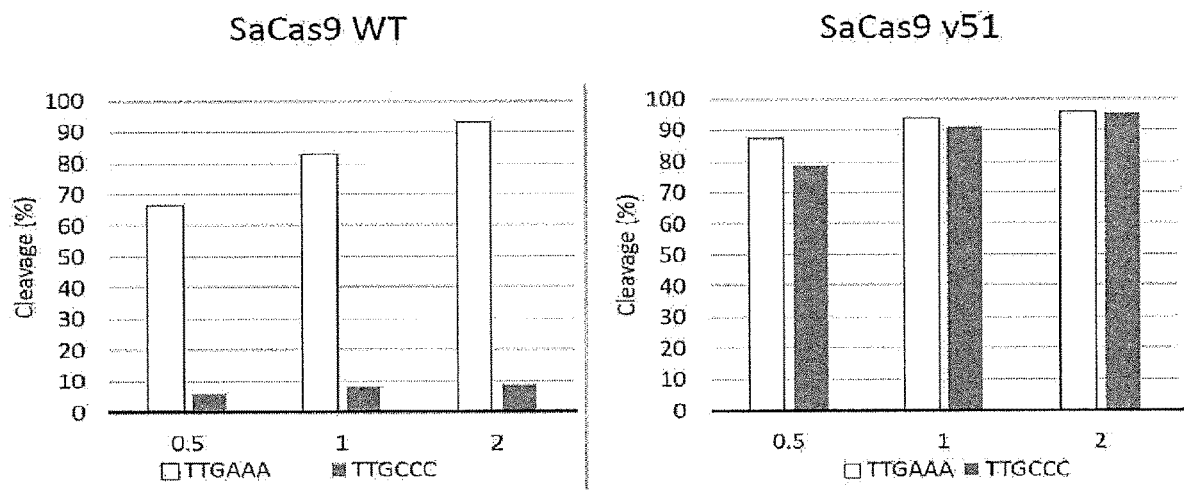

It has been confirmed that wild-type SaCas9 has a restricted cleavage activity on the target plasmid DNA, whereas restriction on the cleavage activity on the target plasmid DNA is improved in mutant SaCas9 (FIG. 4-1, FIG. 4-2).

Using wild-type SaCas9 (SaCas9 WT) and mutant SaCas9 (SaCas9 v15) and in the same manner as in Example 1, the cleavage activity on the target plasmid DNA was examined by changing the treatment time, and preference for various PAM sequences was confirmed. As the PAM sequence, 5'-NNGAAT-3' (PAM sequence 5) was also examined in addition to the PAM sequences 1-4 described in Table 1. The results are shown in FIG. 4-3. SaCas9 WT showed almost no cleavage activity on PAM sequence 4 at any treatment time, but SaCa9 v15 showed cleavage activity also on PAM sequence 4 after treatment for a given time or longer. In addition, SaCas9 v51, which is another mutant SaCas9, showed cleavage activity on PAM sequence 4 (5'-TTGCCC-3') even with a shorter treatment time (FIG. 4-4).

Example 3

1. Verification of Target Gene Cleavage Activity in Eukaryotic Cells (1) Construct Design Wild-type or mutant SaCas9 gene with codon optimized by gene synthesis was incorporated in the BglII/XhoI site of CP-LvC9NU-09 vector (Genocopia). In addition, to target a plurality of sequences in HPRT and EMX1 genes, various guide RNA expression plasmids were produced by incorporating guide RNAs into the BsmB1 site of the pCRISPR-LvSG03 (Genocopia) vector. The constitution of each guide RNA expression plasmid is shown in Table 2.

TABLE 2-1

| HPRT NNGAAA-PAM | | | |
| --- | --- | --- | --- |
| Position | Strand | Spacer Sequence | PAM |
| HPRT 134473270 A-1 | -1 | AAAAATAACCTTAGTCTATCA (SEQ ID NO: 5) | GAGAAA |
| HPRT 134473330 A-2 | 1 | TTGTATCCTGTAATGCTCTCA (SEQ ID NO: 6) | TTGAAA |
| HPRT 134473362 A-3 | -1 | ACCTGGTTCATCATCACTAAT (SEQ ID NO: 7) | CTGAAA |
| HPRT 134473423 A-4 | 1 | CTAATCATTATGCTGAGGATT (SEQ ID NO: 8) | TGGAAA |
| HPRT 134473508 A-5 | -1 | GCTGATGTTTGAAATTAACAC (SEQ ID NO: 9) | AAGAAA |

TABLE 2-2

| HPRT NNGTTT-PAM | | | |
| --- | --- | --- | --- |
| Position | Strand | Spacer Sequence | PAM |
| HPRT 134473305 T-1 | 1 | TTAACATCTTAATCCAATCAA (SEQ ID NO: 10) | ATGTTT |
| HPRT 134473345 T-2 | -1 | TAATCTGAAAAAGAAATATAG (SEQ ID NO: 11) | CTGTTT |
| HPRT 134473431 T-3 | 1 | TATGCTGAGGATTTGGAAAGG (SEQ ID NO: 12) | GTGTTT |
| HPRT 134473483 T-4 | 1 | GGTAAGTAAGATCTTAAAATG (SEQ ID NO: 13) | AGGTTT |
| HPRT 134473525 T-5 | -1 | AAGTACTCAGAACAGCTGCTG (SEQ ID NO: 14) | ATGTTT |

TABLE 2-3

| HPRT NNGRRT-PAM | | | |
| --- | --- | --- | --- |
| Position | Strand | Spacer Sequence | PAM |
| HPRT 134473416 R-1 | 1 | TGCATACCTAATCATTATGCT (SEQ ID NO: 15) | GAGGAT |
| HPRT 134473427 R-2 | 1 | TCATTATGCTGAGGATTTGGA (SEQ ID NO: 16) | AAGGGT |

TABLE 2-3-continued

HPRT NNGRRT-PAM

| Position | Strand | Spacer Sequence | PAM |
|---|---|---|---|
| HPRT R-3 | 134473443 | -1 | CCTGTCCATAATTAGTCCATG (SEQ ID NO: 17) | AGGAAT |

TABLE 2-4

EMX1 NNGCCC-PAM

| Position | Strand | Spacer Sequence | PAM |
|---|---|---|---|
| EMX1 C-1 | 72934106 | -1 | TGCTTGTCCCTCTGTCAATGG (SEQ ID NO: 18) | CGGCCC |
| EMX1 C-2 | 72934025 | -1 | GGAGTGGCCAGAGTCCAGCTT (SEQ ID NO: 19) | GGGCCC |
| EMX1 C-3 | 72931452 | 1 | GGCTTCTCAGGAATGACACCC (SEQ ID NO: 20) | CGGCCC |
| EMX1 C-4 | 72931442 | -1 | GGCCGGGTGTCATTCCTGAG (SEQ ID NO: 21) | AAGCCC |
| EMX1 C-5 | 72931600 | 1 | GAGAACCACCCAGGGTCCAGG (SEQ ID NO: 22) | TGGCCC |

TABLE 2-5

EMX1 NNGGGG-PAM

| Position | Strand | Spacer Sequence | PAM |
|---|---|---|---|
| EMX1 G-1 | 72931461 | -1 | GACTCAGGGCCAGATGCAGGG (SEQ ID NO: 23) | CCGGGG |
| EMX1 G-2 | 72934016 | -1 | AGAGTCCAGCTTGGGCCCACG (SEQ ID NO: 24) | CAGGGG |
| EMX1 G-3 | 72934051 | 1 | TGGCCACTCCCTGGCCAGGCT (SEQ ID NO: 25) | TTGGGG |
| EMX1 G-4 | 72934091 | 1 | TGGCCCCACAGGGCTTGAAGC (SEQ ID NO: 20) | CCGGGG |
| EMX1 G-5 | 72931539 | 1 | ACAGTCATAGCAGGCTCCAGG (SEQ ID NO: 27) | GTGGGG |

TABLE 2-6

EMX1 NNGRRT-PAM

| Position | Strand | Spacer Sequence | PAM |
|---|---|---|---|
| EMX1 R-1 | 72934047 | -1 | GGCCTCCCCAAAGCCTGGCCA (SEQ ID NO: 28) | GGGAGT |
| EMX1 R-2 | 72934062 | 1 | TGGCCAGGCTTTGGGGAGGCC (SEQ ID NO: 29) | TGGAGT |
| EMX1 R-3 | 72931439 | 1 | GCCAGCCCACTTGGGCTTCTC (SEQ ID NO: 30) | AGGAAT |

(2) Expression in HEK Cells

HEK strain was transformed with the produced two kinds of SaCas9 expression vectors LvNUC9-09SaCas9 (wildtype (WT), PAM-flexible variant (PF)) (250 ng) and guide RNA expression plasmid (LvSG03 sgRNA) in a 24 well plate by the use of lipofectamine (Lipofectamine 2000). After culturing for one day, 1 µg/ml puromycin was added to the medium and the cells were recovered on day 4.

(3) PCR

From the recovered cells, samples were prepared using Extraction Buffers 1 and 2 of Guide-it™ Mutation Detection Kit (631448) (Clontech). Then, PCR was performed using Q5 (registered trade mark) Hot Start High-Fidelity 2× Master Mix (M0494) (NEB). The detailed PCR conditions were as follows. HPRT PCR primer (Amplicon size: 468 bps)

HPRT PCR primer (Amplicon size: 468 bps)
(SEQ ID NO: 31)
Forward:    TACACGTGTGAACCAACCCG (SEQ ID NO: 32)
Reverse:    GTAAGGCCCTCCTCTTTTATTT EMX1 region A PCR primer (Amplicon size: 643 bps)
(SEQ ID NO: 33)
Forward:    AGTTTCTCATCTGTGCCCCTCC (SEQ ID NO: 34)
Reverse:    CTGAACGCGTTTGCTCTACCAG EMX1 region B PCR primer (Amplicon size: 732 bps)
(SEQ ID NO: 35)
Forward:    TTTCACTTGGGTGCCCTAGG (SEQ ID NO: 36)
Reverse:    CCCTCTTGCCAGAACTTCC Cycling Conditions
Initial Denaturation: 98° C., 30 sec
35 cycles: 98° C. (5 sec), 63° C. (20 sec), 72° C. (20 sec)
Final Extension: 72° C., 2 min
Hold: 4-10° C.

(4) T7 Endonuclease I Treatment

Figures 1, 5:
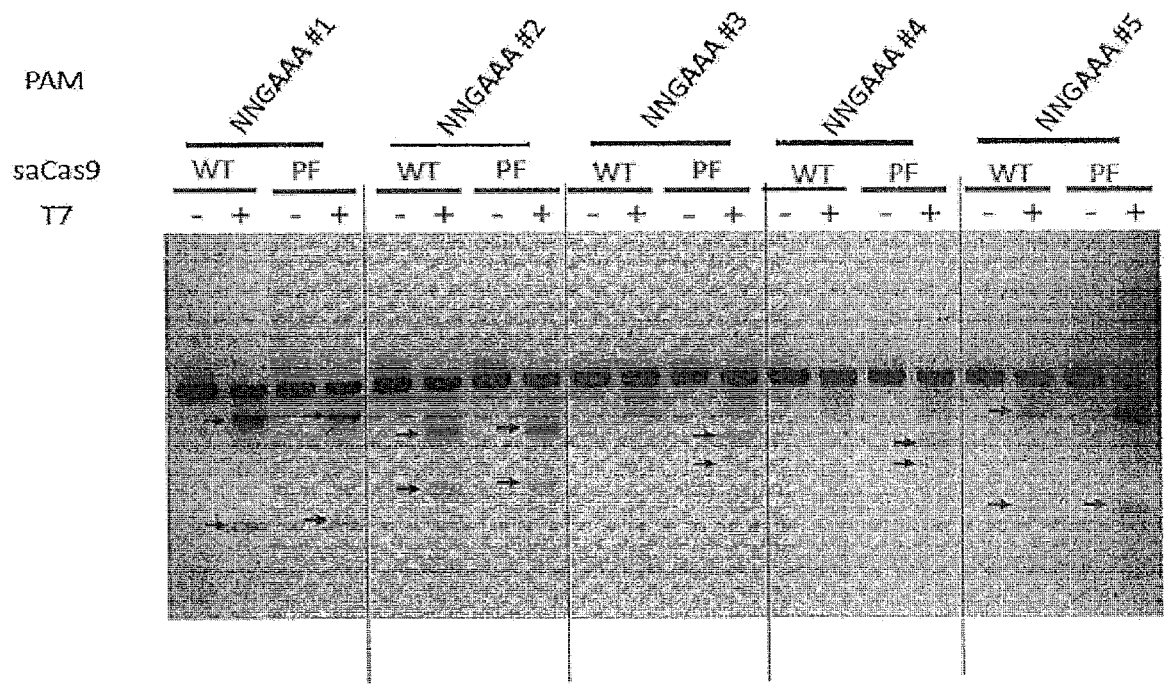
FIG. 5 shows the results verifying alteration of PAM sequence of variants in Example 3 using cleavage activity in an animal cell (HEK293 cell) as an index.
Figures 2, 5:
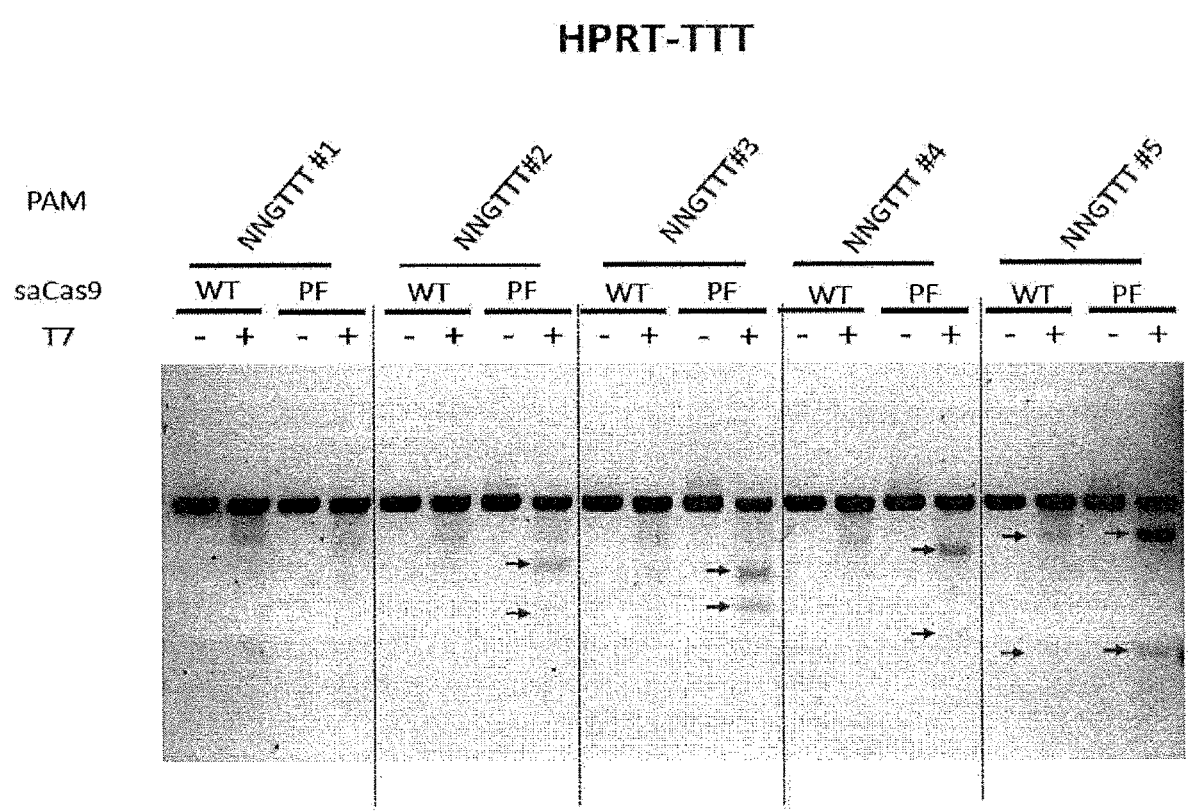
Figures 3, 5:
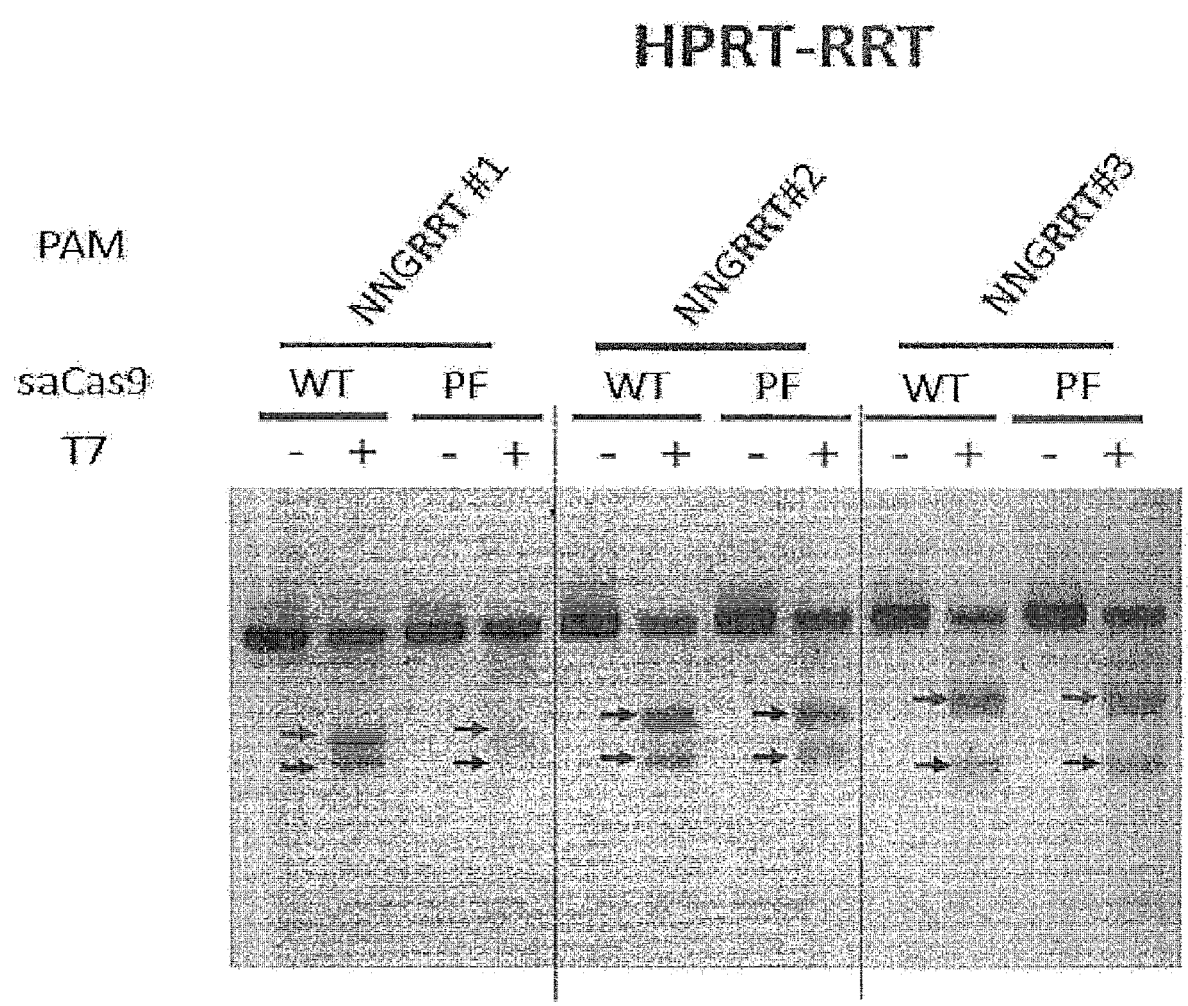
Figures 4, 5:
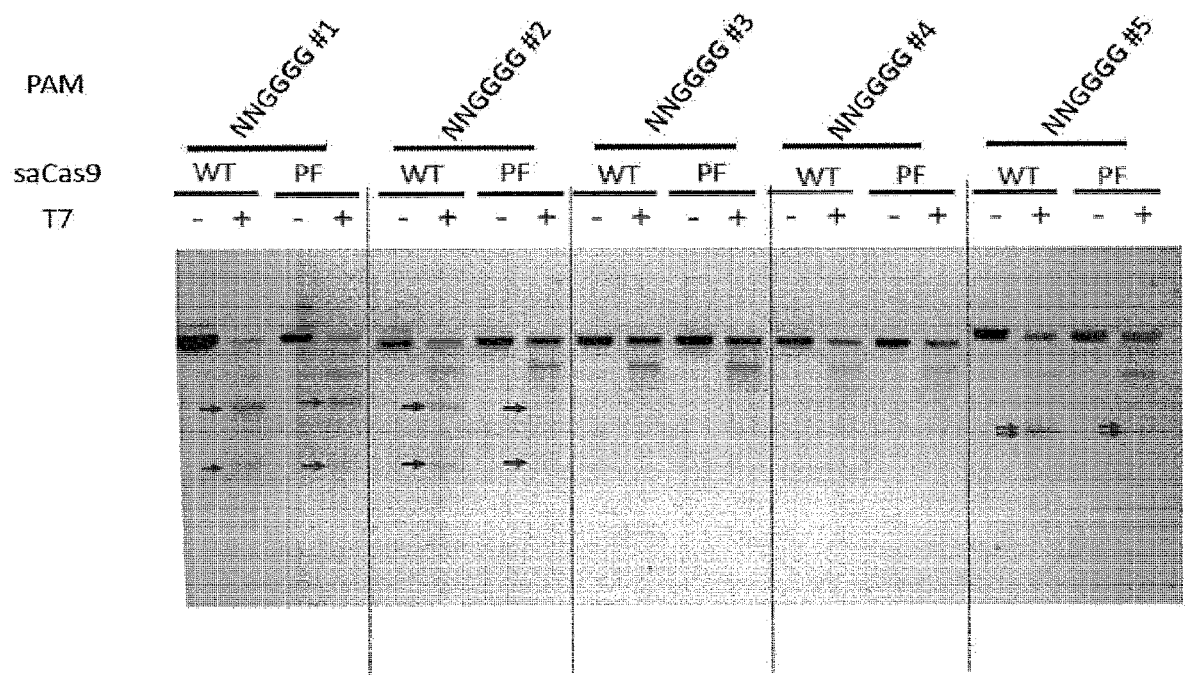
Figure 5:
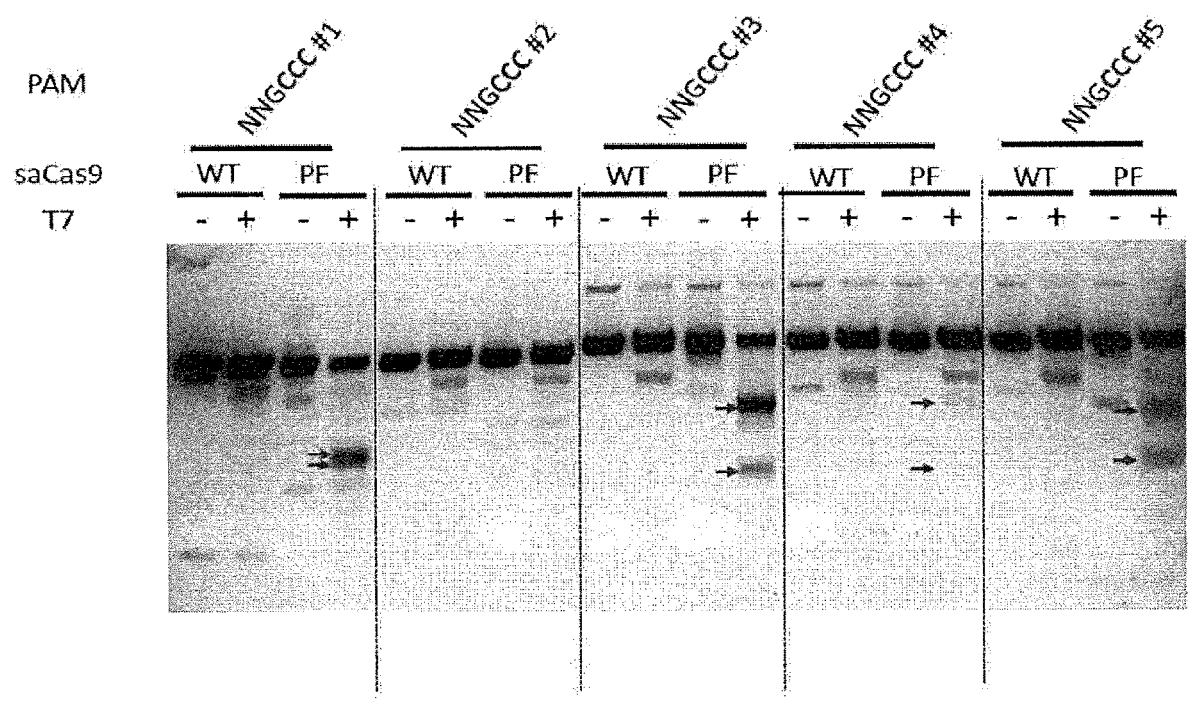
Figures 5, 6:
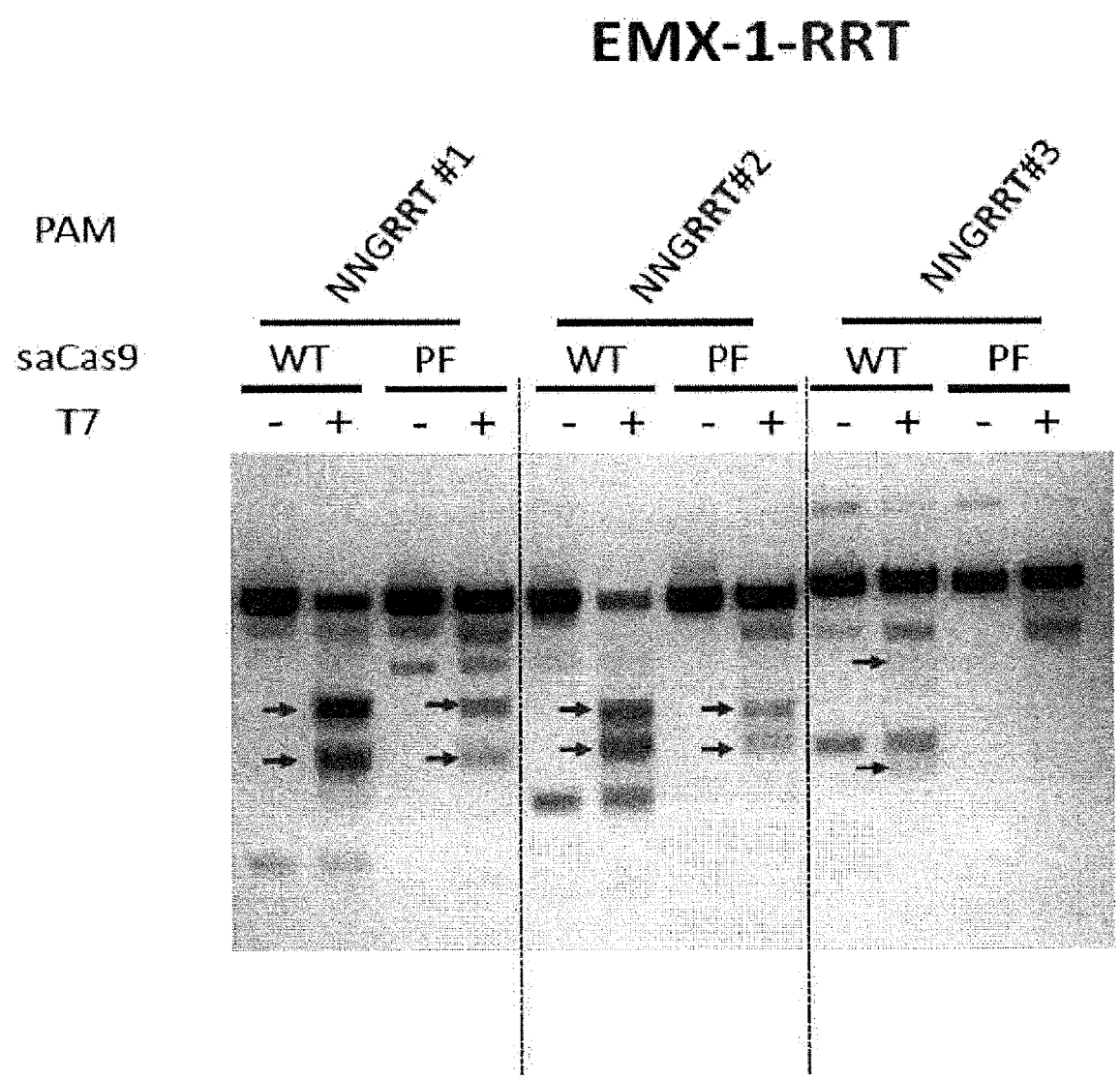
FIG. 6 shows the amino acid sequence (FIG. 6-1) (SEQ ID NO: 38) of NLS-WT-dSaCas(D10A,N580A)-NLS-KRAB-P2A-Puro fusion protein (sometimes to be abbreviated as WT-dSaCas9-KRAB) and a base sequence encoding same (FIG. 6-2) (SEQ ID NO: 37).

The obtained PCR product was heat denatured and annealed again. The obtained reaction product was treated with T7 Endonuclease I (T7 Enconuclease I (M0302)) and the obtained sample was electrophoresed using 1% concentration of agarose gel, and bands corresponding to the cleavage products were confirmed. The results are shown in FIG. 5 (FIGS. 5-1 to 5-6).

Example 4: Off-Target Analysis of Cas9 Variant (Method)
1. Cloning

Using dSaCas9 (protein in which, in the sequence shown in SEQ ID NO: 2, aspartic acid at the 10-position is substituted with alanine and asparagine at the 580-position is substituted with alanine: also referred to as dSaCas9 (D10A, N580A)) and mutant dSaCas9 obtained by introducing a mutation therein, off-target analysis was performed. dSaCas9 is one introduced a null mutation into a wild-type SaCas9.

A gene construct of mutant dSaCas9 in which KRAB-P2A-Puro is linked to the C-terminal of a dSaCas9 (D10A, N580A) protein having a nuclear localization signal (NLS) linked to both ends was incorporated into pX601 vector (F. Ann Ran et al., Nature 2015; 520(7546); pp. 186-191).

Mutant dSaCas9 was produced by introducing null mutation (D10A, N580A) by the use of mutant SaCas9 (v15) or mutant SaCas9 (v51) produced in Example 1 instead of wild-type SaCas9. WT-dSaCas9-KRAB (SEQ ID NO: 37 and SEQ ID NO: 38; FIG. 6) PF(v15)-dSaCas9 (D10A, N580A)-KRAB (SEQ ID NO: 39 and SEQ ID NO: 40; FIG. 7) PF(v51)-dSaCas9 (D10A, N580A)-KRAB (SEQ ID NO: 41 and SEQ ID NO: 42; FIG. 8)

2. Selection and Cloning of sgRNA (Single-Molecule Guide PNA) Sequence

Guide sequence targeting the KRAS gene was selected based on the predicted on-target and off-target scores obtained by Benchling software (www.benchling.com). The sequence is in the chr12:25, 249,500-25,253,000 region published by the UCSC genome browser (Human GRCh38/hg38 assembly). A guide RNA compatible with WT-dSaCas9 (#1, 2, 3) is different from a guide RNA compatible with PF(v15)-dSaCas9 (#4, 5, 6) since PAM sequence has been changed.

The three control RNA guides (C1, C2, C3) were selected from Human CRISPR Knockout Pooled Library (Sanjana N. et al, Nat Methods. 2014 August; 11(8):783-784.). The stuffer sequence is a nucleotide sequence present in advance in the effector plasmid before cloning the guide RNA and acts as another control guide RNA sequence.

All guide RNAs were fused to tracer RNA sequences to produce sgRNAs, which were cloned into effector vectors as follows:
px601-AIO-CMV-WT-dSaCas9-Puro; #1, 2, 3, C1, C2, C3, stuffer
px601-AIO-CMV-PF(v15)dSaCas9-Puro; #4, 5, 6, C1, C2, C3, stuffer
px601-AIO-CMV-PF(v51)dSaCas9-Puro; C1, C2, C3

SgRNA expression is driven by the U6 promoter and the vector is constructed to express puromycin gene under P2A promoter to facilitate tracking and selection of sgRNA expressing cells.

The sequence information of each sgRNA and stuffer sequence is as follows.

```
sgRNA-KRAS#1 (WT);
                              (SEQ ID NO: 43)
GGGAAGGCTGGACCGAGGCAG sgRNA-KRAS#2 (WT);
                              (SEQ ID NO: 44)
CAGTCCGAAATGGCGGGGCC sgRNA-KRAS#3 (WT);
                              (SEQ ID NO: 45)
AATCGAGCTCCGAGCACACCG sgRNA-KRAS#4 (PF-v15);
                              (SEQ ID NO: 46)
GTGCGGGAGAGAGGTACGGAG sgRNA-KRAS#5 (PF-v15);
                              (SEQ ID NO: 47)
GGAGCGAGCGCGGCGCAGGCA sgRNA-KRAS#6 (PF-v15);
                              (SEQ ID NO: 48)
CGGCCGCGGCGGCGGAGGCAG sgRNA-C1;
                              (SEQ ID NO: 49)
ACGGAGGCTAAGCGTCGCAA sgRNA-C2;
                              (SEQ ID NO: 50)
CGCTTCCGCGGCCCGTTCAA sgRNA-C3;
                              (SEQ ID NO: 51)
GTAGGCGCGCCGCTCTCTAC

Stuffer sequence;
                              (SEQ ID NO: 52)
GAAACACCGGAGACCACGGCAGGTCTCA
```

3. Cell Culture and Transfection

HEK293FT cells were seeded in a 24-well plate at a density of 75,000 cells per well 24 hr before transfection and cultured in DMEM medium supplemented with 10% FBS, 2 mM fresh L-glutamine, 1 mM sodium pyruvate and non-essential amino acid. The cells were transfected according to the manual and using 500 ng of px601-CMV-WT-dSaCas9-Puro, px601-CMV-PF(v15)dSaCas9-Puro or px601-CMV-PF(v51)dSaCas9-Puro, each containing one of sgRNAs, and 1.5 μl Lipofectamine 2000 (Life technologies). At 72 hr after transfection (48 hr after selection of 1 μg/ml puromycin), the cells were recovered and dissolved in RLT buffer (Qiagen), and the total RNA was extracted using RNeasy kit (Qiagen).

4. Submission of Samples for RNAseq Analysis

Samples were prepared in duplicate for each experiment and 2.5 μg of total RNA per sample was analyzed with GENEWIZ. The RNA library was prepared by poly-A selection followed by sequencing (Illumina HiSeq, 2× 150b.p., single index per lane sequencing configuration) as shown in GENEWIZ (www.genewiz.com). All RNAs met GENEWIZ QC criteria. The target untreated paired-end read was 25M per sample.

5. A raw fastq file obtained by standard paired-endo illumina sequencing was aligned to *H. sapiens* genome build, GRCh38.p12 (hypertext transfer protocol secure useast.ensembl.org/Homo_sapiens/Info/Index) using Spliced Transcripts Alignment to a Reference (STAR) (hypertext transfer protocol secure labshare.cshl.edu/shares/gingeraslab/www-data/dobin/STAR/STAR.posix/doc/STARmanual.pdf). Biological replicates were grouped, and differential analysis between samples was performed in advance using DESeq2 (hypertext transfer protocol secure bioconductor.org/packages/release/bioc/html/DESeq2.html) using processed alignment data.

FKPM data files were processed; a gene group having no read in any of the samples, genes with average expression of less than 1.0 read, and a gene group having small transcripts (microRNAs and SNORs) were excluded from the analysis.

All replicate samples showed a correlation coefficient>98%. The average expression from the two replicates was used to calculate a representative expression value for each gene of each class. MvA plots were produced using MultiplotStudio software. The X-axis shows mean 2-class expression and the Y-axis shows log 2 fold-change between the two classes.

(Results)

It was found that PF(v15)-dSaCas9 more strongly suppresses the expression of KRAS gene and shows lower off-target suppression than WT-dSaCas9 (FIG. 9).

MvA plots of the classes having KRAS-sgRNA and control-stuffer sgRNA are respectively shown for WT-dSaCas9 and PF(v15)-dSaCas9. The X-axis shows mean of 2-class expression and the Y-axis shows log 2 fold-change between two classes. The KRAS gene was suppressed by WTdSaCas9 having three different sgRNAs (sgRNA #1, #2 and #3), and PF(v15)-Cas9 having three different sgRNAs (sgRNA #4, #5, #6). The log 2 fold-change suppression for control-stuffer sgPNA was as follows; −2.261 (sgRNA #1), −1.888 (sgRNA #2) and −2.934 (sgRNA #3), −5.041 (sgRNA #4), −2.538 (sgRNA #5) and −2.642 (sgRNA #6).

PF(v15)-dSaCas9 showed less off-target suppression. The number of genes suppressed not less than twice compared to control-stuffer sgRNA was 71 (sgRNA #1), 93 (sgRNA #2) or 57 (sgRNA #3) for WT-dSaCas9, whereas it was 38 (#4), 23 (#5) or 35 (#6) for PF(v15)-dSaCas9.

Figure 10:
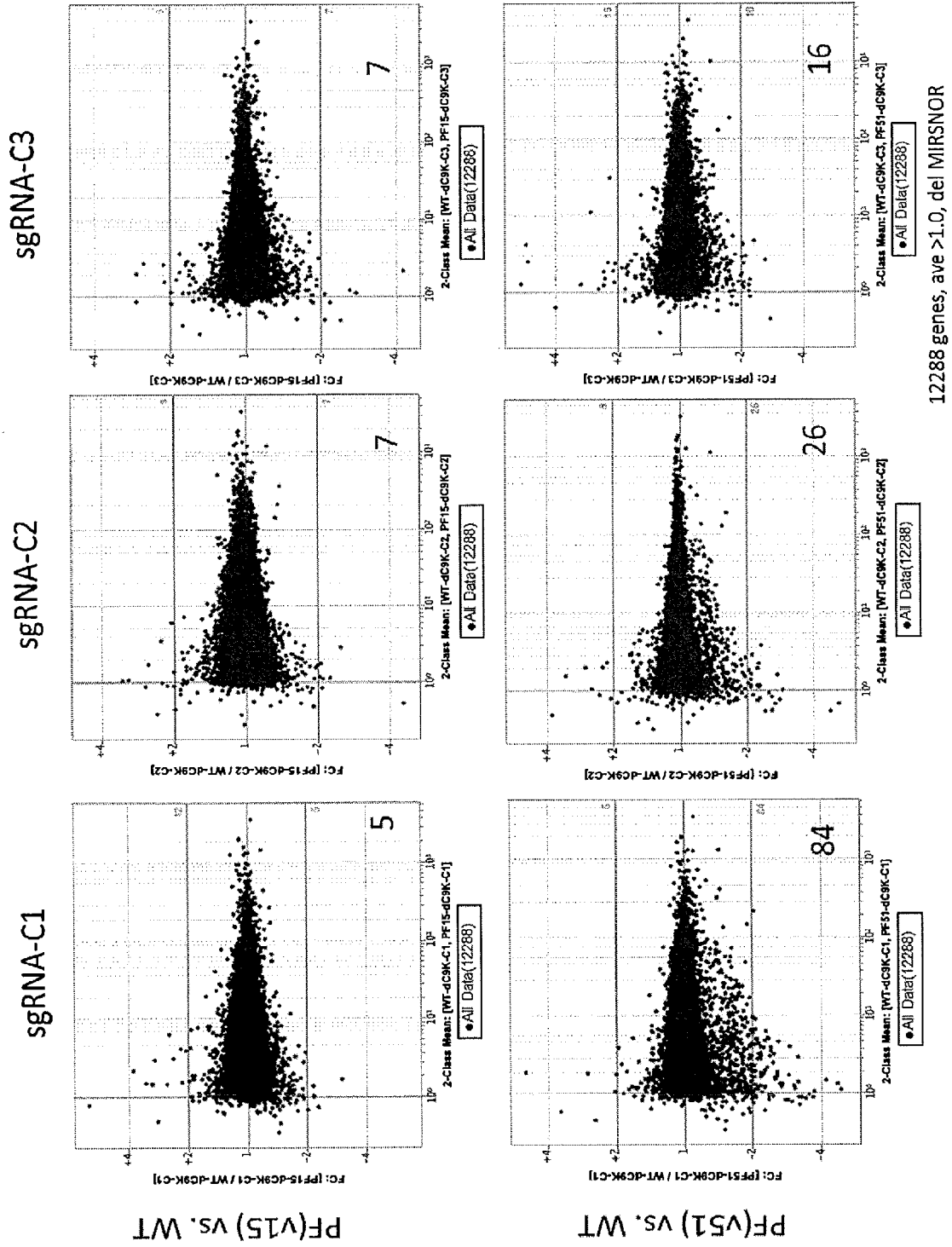
FIG. 10 shows an off-target suppressive effect on WT-dSaCas9 of PF(v15) and PF(v51).

The off-target suppressive effect of PF(v15) and PF(v51) on WT-dSaCas9 was examined (FIG. 10).

The MVA plot shows the number of genes that showed suppression of not less than twice on WT-dSaCas9 by PF(v15) and PF(v51). The comparison was performed using three control sgRNAs; C1, C2 and C3 and by PF(v15) vs. WT and PF(v51) vs. WT. PF(v15) showed extremely low numbers of off-target suppression (more than 2-fold suppression) of 5, 7 and 7 genes respectively for C1, C2 and C3. PF(v51) showed greater numbers of off-target suppression (more than 2-fold suppression) of 84, 26 and 16 genes respectively for C1, C2 and C3. The X-axis shows mean of 2-class expression and the Y-axis shows log 2 fold-change between two classes.

INDUSTRIAL APPLICABILITY

According to the present invention, a Cas9 protein can be obtained that recognizes a wide range of PAM sequences while retaining binding strength with a guide RNA. This Cas9 protein has a strong target DNA binding ability as compared to that of WT Cas9 protein, and also shows low off-target binding ability. In addition, a simple and rapid site-specific genome editing technology for a target sequence can be provided that uses the aforementioned Cas9 protein.

This application is based on U.S. provisional patent application No. 62/554,227 (filing date: Sep. 5, 2017), US provisional patent application No. 62/668,968 (filing date: May 9, 2018), and U.S. provisional patent application No. 62/724,981 (filing date: Aug. 30, 2018), each filed in US, the contents of which are incorporated in full herein.

The invention claimed is:

1. A protein having at least 80% sequence identity to SEQ ID NO: 2 with mutations at the 985-position and the 991-position, and optionally at the 986-position,
    wherein said protein further comprises:
    mutations at at least five sites selected from the group consisting of the 782-position, the 800-position, the 888-position, the 968-position, the 988-position, the 1017-position and the 1021-position; and
    (i) mutations at the 927-position and the 929-position,
    (ii) a mutation at the 889-position, or
    (iii) mutations at the 927-position, the 929-position and the 889-position,
    and has a binding ability to guide RNA.

2. The protein according to claim 1, wherein the protein comprises mutation at at least 6 sites selected from the group consisting of the 782-position, the 800-position, the 888-position, the 968-position, the 988-position, the 1017-position and the 1021-position.

3. The protein according to claim 1, wherein:
    the mutation at the 782-position is substitution with lysine;
    the mutation at the 800-position is substitution with arginine;
    the mutation at the 888-position is substitution with lysine;
    the mutation at the 968-position is substitution with arginine;
    the mutation at the 985-position is substitution with alanine;
    the mutation at the 986-position is substitution with alanine;

the mutation at the 991-position is substitution with alanine;

the mutation at the 988-position is substitution with histidine;

the mutation at the 1017-position is substitution with phenylalanine;

the mutation at the 1021-position is substitution with serine;

the mutation of (i) is substitution of the 927-position with lysine, and substitution of the 929-position with asparagine or aspartic acid;

the mutation of (ii) is substitution of the 889-position with arginine; and the mutation of (iii) is substitution of the 927-position with lysine, substitution of the 929-position with asparagine, and substitution of the 889-position with asparagine.

4. The protein according to claim 1, consisting of a sequence comprising an amino acid sequence resulting from substitutions of:

glutamic acid at the 782-position with lysine,
leucine at the 800-position with arginine;
asparagine at the 968-position with arginine;
asparagine at the 985-position with alanine;
asparagine at the 986-position with alanine;
arginine at the 991-position with alanine;
leucine at the 988-position with histidine;
alanine at the 1021-position with serine;
threonine at the 927-position with lysine; and
lysine at the 929-position with asparagine; in the amino acid sequence shown in SEQ ID NO: 2;
and having a binding ability to guide RNA.

5. The protein according to claim 1, consisting of a sequence comprising an amino acid sequence resulting from substitutions of:

glutamic acid at the 782-position with lysine;
leucine at the 800-position with arginine;
asparagine at the 968-position with arginine;
asparagine at the 985-position with alanine;
asparagine at the 986-position with alanine;
arginine at the 991-position with alanine;
leucine at the 988-position with histidine;
alanine at the 1021-position with serine;
alanine at the 889-position with asparagine;
threonine at the 927-position with lysine; and
lysine at the 929-position with asparagine; in the amino acid sequence shown in SEQ ID NO: 2;
and having a binding ability to guide RNA.

6. The protein according to claim 1, consisting of a sequence comprising an amino acid sequence resulting from substitutions of:

glutamic acid at the 782-position with lysine,
leucine at the 800-position with arginine;
asparagine at the 968-position with arginine;
asparagine at the 985-position with alanine;
arginine at the 991-position with alanine;
alanine at the 1021-position with serine;
threonine at the 927-position with lysine;
lysine at the 929-position with asparagine; and
isoleucine at the 1017-position with phenylalanine; in the amino acid sequence shown in SEQ ID NO: 2;
and having a binding ability to guide RNA.

7. The protein according to claim 1, having identity of 90% or more at a site other than the mutated positions in the SEQ ID NO: 2.

8. The protein according to claim 1, wherein one to several amino acids are substituted, deleted, inserted and/or added at a site other than the mutated positions in the SEQ ID NO: 2 while having at least 80% sequence identity to SEQ ID NO: 2.

9. The protein according to claim 1, which has RNA-guided DNA endonuclease activity.

10. The protein according to claim 1, further having a mutation that deletes nuclease activity in the amino acid sequence as set forth in SEQ ID NO: 2.

11. The protein according to claim 1, further having a mutation that deletes nuclease activity in the amino acid sequence as set forth in SEQ ID NO: 2 and having mutation at sites corresponding to the 10-position, the 556-position, the 557-position and/or the 580-position in the amino acid sequence as set forth in SEQ ID NO: 2.

12. The protein according to claim 11, wherein:

the mutation at the 10-position is substitution of aspartic acid with alanine;

the mutation at the 556-position is substitution of aspartic acid with alanine;

the mutation at the 557-position is substitution of histidine with alanine; and the mutation at the 580-position is substitution of asparagine with alanine.

13. The protein according to claim 10, wherein a transcriptional regulator protein or domain is linked to the N-terminal or C-terminal of the mutant Cas9 protein.

14. The protein according to claim 13, wherein the transcriptional regulator protein is a transcription activator.

15. The protein according to claim 14, wherein the transcriptional regulator protein is a transcription silencer or a transcription inhibitor.

16. A protein-RNA complex provided with the protein according to claim 1 and a guide RNA comprising a polynucleotide composed of a base sequence complementary to a base sequence located 1 to 24 bases upstream from a proto-spacer adjacent motif (PAM) sequence in a target double-stranded polynucleotide.

17. A method for site-specifically modifying a target double-stranded polynucleotide, the method comprising:

mixing and incubating a target double-stranded polynucleotide, a protein and a guide RNA, such that the protein modifies the target double-stranded polynucleotide at a binding site located upstream of a PAM sequence; wherein:

the target double-stranded polynucleotide comprises a PAM sequence composed of NNGNNN, wherein, N is any base and G is guanine;

the protein is the protein according to claim 1, and the guide RNA comprises a polynucleotide composed of a base sequence complementary to a base sequence located 1 to 24 bases upstream from the PAM sequence in the target double-stranded polynucleotide.

18. The method according to claim 17, wherein the modification is site specific cleavage in the target double-stranded polynucleotide.

19. The method according to claim 17, wherein the modification is site specific substitution, deletion and/or addition of one or more nucleotides in the target double-stranded polynucleotide.

20. A method for increasing expression of a target gene in a cell, the method comprising expressing the protein according to claim 14 and one or plural guide RNAs for the target gene in the cell.

21. A method for decreasing expression of a target gene in a cell, the method comprising expressing the protein according to claim 15 and one or plural guide RNAs for the target gene in the cell.

22. The method according to claim 20, wherein the cell is a eukaryotic cell.

23. The method according to claim 20, wherein the cell is a yeast cell, a plant cell or an animal cell.

24. The method according to claim 21, wherein the cell is a eukaryotic cell.

25. The method according to claim 21, wherein the cell is a yeast cell, a plant cell or an animal cell.

* * * * *